(12) United States Patent
Chana et al.

(10) Patent No.: US 10,485,554 B2
(45) Date of Patent: Nov. 26, 2019

(54) SYSTEM FOR POSITIONING A CUTTING GUIDE IN KNEE SURGERY

(71) Applicant: Synvasive Technology, Inc., El Dorado Hills, CA (US)

(72) Inventors: Barjinder S. Chana, Reno, NV (US); Michael G. Fisher, Reno, NV (US); Michael Haight, Sacramento, CA (US); Leo Beckers, Grimbergen (BE); Kenneth D. Johannaber, Reno, NV (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 566 days.

(21) Appl. No.: 15/239,029

(22) Filed: Aug. 17, 2016

(65) Prior Publication Data
US 2017/0042554 A1   Feb. 16, 2017

Related U.S. Application Data

(63) Continuation of application No. 13/524,405, filed on Jun. 15, 2012, now Pat. No. 9,439,656, which is a
(Continued)

(51) Int. Cl.
*A61F 2/46* (2006.01)
*A61B 17/15* (2006.01)
(Continued)

(52) U.S. Cl.
CPC .......... *A61B 17/155* (2013.01); *A61B 17/025* (2013.01); *A61F 2/4657* (2013.01);
(Continued)

(58) Field of Classification Search
CPC .......... A61B 17/025; A61B 2017/0268; A61F 2/4657
See application file for complete search history.

(56) References Cited

U.S. PATENT DOCUMENTS

| 4,501,266 A | 2/1985 | McDaniel |
| 5,116,338 A | 5/1992 | Poggie et al. |

(Continued)

FOREIGN PATENT DOCUMENTS

| WO | WO-2005037121 A1 | 4/2005 |
| WO | WO-2005089681 A2 | 9/2005 |
| WO | WO-2006047005 A2 | 5/2006 |

OTHER PUBLICATIONS

"U.S. Appl. No. 14/692,117, Final Office Action dated Oct. 31, 2017", 6 pgs.
(Continued)

*Primary Examiner* — Si Ming Ku
(74) *Attorney, Agent, or Firm* — Schwegman Lundberg & Woessner, P.A.

(57) ABSTRACT

A system is provided for positioning a cutting guide on a femur of a knee to make a cut along a distal end of the femur during knee surgery. The system may generally include an adjustable femoral attachment member configured to attach to a cut distal end of the femur, a cutting guide removably attachable to the femoral attachment member and configured to guide a surgical saw to make an additional cut on the distal end of the femur, and a force sensor for positioning between the femoral attachment member and a proximal end of a tibia of the knee. The force sensor may include a medial portion for sensing a medial force in the knee and a lateral portion for sensing a lateral force in the knee.

20 Claims, 53 Drawing Sheets

Related U.S. Application Data continuation-in-part of application No. 12/609,666, filed on Oct. 30, 2009, now abandoned.

(60) Provisional application No. 61/109,770, filed on Oct. 30, 2008.

(51) Int. Cl.
*A61B 17/02* (2006.01)
*A61B 90/00* (2016.01)

(52) U.S. Cl.
CPC . *A61B 2017/0268* (2013.01); *A61B 2090/064* (2016.02); *A61F 2002/4666* (2013.01)

(56) References Cited

U.S. PATENT DOCUMENTS

| | | | |
|---|---|---|---|
| 5,213,112 | A | 5/1993 | Niwa et al. |
| 5,470,354 | A | 11/1995 | Hershberger et al. |
| 5,540,696 | A | 7/1996 | Booth, Jr. et al. |
| 5,597,379 | A | 1/1997 | Haines et al. |
| 5,656,785 | A | 8/1997 | Trainor et al. |
| 5,669,914 | A | 9/1997 | Eckhoff |
| 5,733,292 | A | 3/1998 | Gustilo et al. |
| 5,800,438 | A | 9/1998 | Tuke et al. |
| 5,860,980 | A | 1/1999 | Axelson, Jr. et al. |
| 5,911,723 | A | 6/1999 | Ashby et al. |
| 6,022,377 | A | 2/2000 | Nuelle et al. |
| 6,575,980 | B1 | 6/2003 | Robie et al. |
| 6,758,850 | B2 | 7/2004 | Smith et al. |
| 7,104,996 | B2 | 9/2006 | Bonutti |
| 7,442,196 | B2 | 10/2008 | Fisher et al. |
| 7,578,821 | B2 | 8/2009 | Fisher et al. |
| 8,323,290 | B2 | 12/2012 | Metzger et al. |
| 9,439,656 | B2 | 9/2016 | Chana et al. |
| 9,980,735 | B2 | 5/2018 | Chana et al. |
| 2005/0209605 | A1 | 9/2005 | Grimm et al. |
| 2005/0240196 | A1 | 10/2005 | Davis et al. |
| 2005/0267485 | A1* | 12/2005 | Cordes ............... A61B 17/02 606/88 |
| 2006/0241569 | A1 | 10/2006 | Disilvestro |
| 2007/0219559 | A1 | 9/2007 | Heavener et al. |
| 2007/0232959 | A1 | 10/2007 | Couture et al. |
| 2007/0244488 | A1 | 10/2007 | Metzger et al. |
| 2010/0063508 | A1 | 3/2010 | Borja et al. |
| 2010/0198275 | A1 | 8/2010 | Chana et al. |
| 2012/0259342 | A1 | 10/2012 | Chana et al. |
| 2015/0230804 | A1 | 8/2015 | Chana et al. |

OTHER PUBLICATIONS

"U.S. Appl. No. 14/692,117, Non Final Office Action dated Jun. 9, 2017", 6 pgs.

"U.S. Appl. No. 14/692,117, Response filed Sep. 6, 2017 to Non Final Office Action dated Jun. 9, 2017", 10 pgs.

"U.S. Appl. No. 12/609,666, Advisory Action dated Dec. 19, 2013", 3 pgs.

"U.S. Appl. No. 12/609,666, Examiner Interview Summary dated May 23, 2013", 3 pgs.

"U.S. Appl. No. 12/609,666, Final Office Action dated Feb. 26, 2015", 10 pgs.

"U.S. Appl. No. 12/609,666, Final Office Action dated Oct. 4, 2013", 10 pgs.

"U.S. Appl. No. 12/609,666, Non Final Office Action dated Feb. 14, 2013", 12 pgs.

"U.S. Appl. No. 12/609,666, Non Final Office Action dated Jun. 26, 2014", 9 pgs.

"U.S. Appl. No. 12/609,666, Non Final Office Action dated Oct. 11, 2012", 10 pgs.

"U.S. Appl. No. 12/609,666, Response filed Jan. 6, 2014 to Advisory Action dated Dec. 19, 2013", 10 pgs.

"U.S. Appl. No. 12/609,666, Response filed Jan. 11, 2013 to Non Final Office Action dated Oct. 11, 2012", 14 pgs.

"U.S. Appl. No. 12/609,666, Response filed May 14, 2013 to Non Final Office Action dated Feb. 14, 2013", 12 pgs.

"U.S. Appl. No. 12/609,666, Response filed May 22, 2012 to Restriction Requirement dated May 11, 2012", 2 pgs.

"U.S. Appl. No. 12/609,666, Response filed Oct. 27, 2014 to Non-Final Office Action dated Jun. 26, 2014", 11 pgs.

"U.S. Appl. No. 12/609,666, Response filed Dec. 4, 2013 to Final Office Action dated Oct. 4, 2013", 10 pgs.

"U.S. Appl. No. 12/609,666, Restriction Requirement dated May 11, 2012", 8 pgs.

"U.S. Appl. No. 13/524,405, Advisory Action dated Oct. 7, 2015", 3 pgs.

"U.S. Appl. No. 13/524,405, Examiner Interview Summary dated Sep. 24, 2015", 3 pgs.

"U.S. Appl. No. 13/524,405, Final Office Action dated Jul. 30, 2015", 8 pgs.

"U.S. Appl. No. 13/524,405, Non Final Office Action dated Dec. 31, 2014", 8 pgs.

"U.S. Appl. No. 13/524,405, Notice of Allowance dated May 17, 2016", 7 pgs.

"U.S. Appl. No. 13/524,405, Response filed Mar. 31, 2015 to Non-Final Office Action dated Dec. 31, 2014", 14 pgs.

"U.S. Appl. No. 13/524,405, Response filed Aug. 4, 2014 to Restriction Requirement dated Jun. 4, 2014", 12 pgs.

"U.S. Appl. No. 13/524,405, Response filed Sep. 24, 2015 to Final Office Action dated Jul. 30, 2015", 9 pgs.

"U.S. Appl. No. 13/524,405, Restriction Requirement dated Jun. 4, 2014", 9 pgs.

"U.S. Appl. No. 14/692,117, Preliminary Amendment filed Apr. 22, 2015", 8 pgs.

"European Application Serial No. 09824192.0, Extended European Search Report dated Mar. 21, 2014", 7 pgs.

"European Application Serial No. 09824192.0, Response filed Oct. 20, 2014 to Extended European Search Report dated Mar. 21, 2014", 18 pgs.

"International Application Serial No. PCT/US2009/062846, International Preliminary Report on Patentability dated May 3, 2011", 9 pgs.

"International Application Serial No. PCT/US2009/062846, International Search Report dated Jan. 31, 2010", 4 pgs.

"International Application Serial No. PCT/US2009/062846, Written Opinion dated Jan. 13, 2010", 8 pgs.

"International Application Serial No. PCT/US20091061941, International Search Report dated Dec. 18, 2009", 1 pg.

Albee, Fred H, "Bone Surgery With Machine Tools", Scientific American vol. 154.4, (Apr. 1936), 178-181.

Eckhoff, D. G, et al., "Three-Dimensional Morphology and Kinematics of the Distal Part of the Femur Viewed in Virtual Reality", Journal of Bone & Joint Surgery, vol. 85-A, Supplement 4, (2003), 97-104.

Mihalko, W. H, et al., "Comparison of Ligament-Balancing Techniques During Total Knee Arthroplasty", Journal of Bone & Joint Surgery, vol. 85-A, Supplement 4,, (2003), 132-135.

Murray, D. G, et al., "Variable Axis Total Knee Surgical Technique", Howmedica Surgical Techniques, Howmedica, Inc., (1977), 2-7.

Ries, M. D, et al., "Soft-Tissue Balance in Revision Total Knee Arthroplasty", Journal of Bone & Joint Surgery, vol. 85-A, Supplement 4,, (2003), 38-42.

"U.S. Appl. No. 14/692,117, Response filed Feb. 1, 2017 to Restriction Requirement dated Dec. 1, 2016", 8 pgs.

"U.S. Appl. No. 14/692,117, Restriction Requirement dated Dec. 1, 2016", 6 pgs.

"U.S. Appl. No. 14/692,117, Notice of Allowance dated Jan. 30, 2018", 6 pgs.

"U.S. Appl. No. 14/692,117, Response filed Dec. 28, 2017 to Final Office Action dated Oct. 31, 2017", 11 pgs.

* cited by examiner

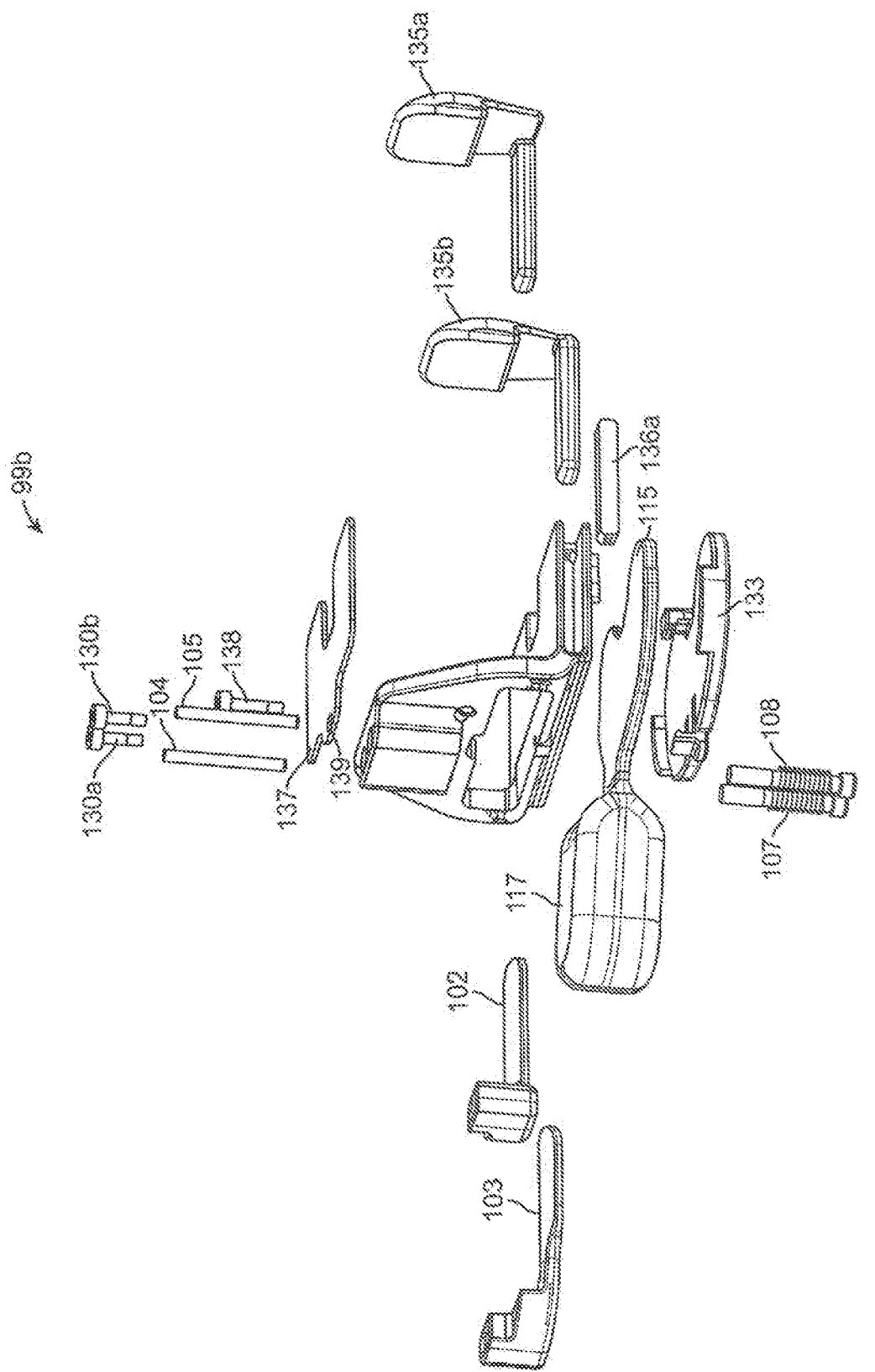

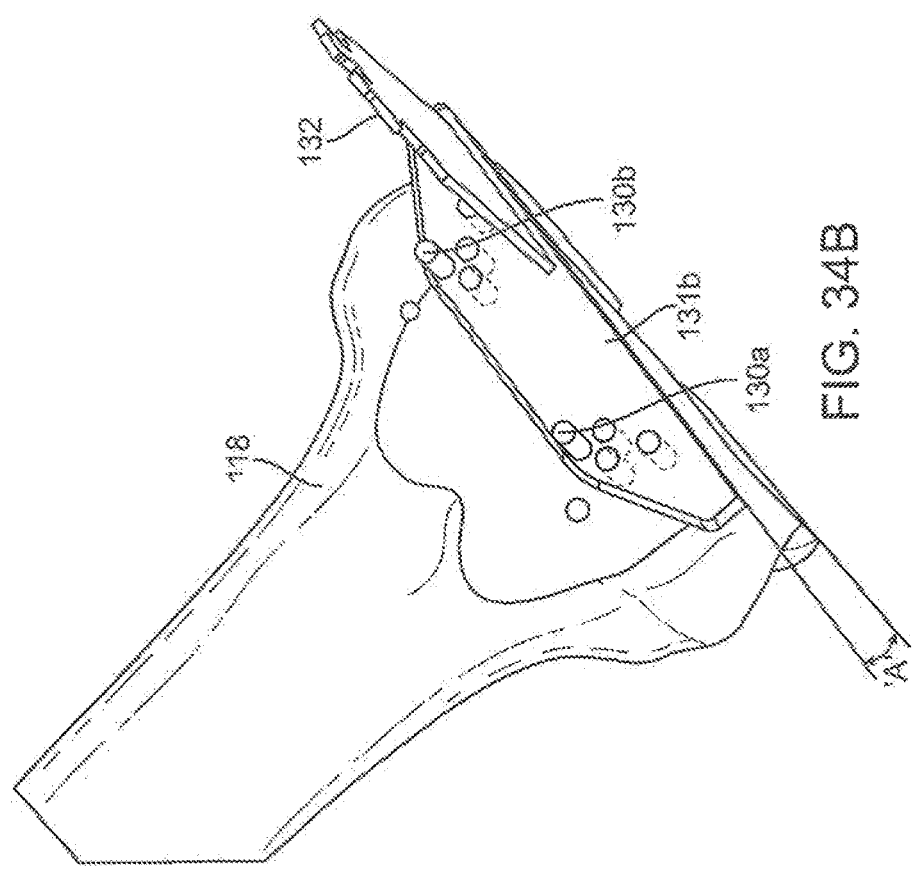
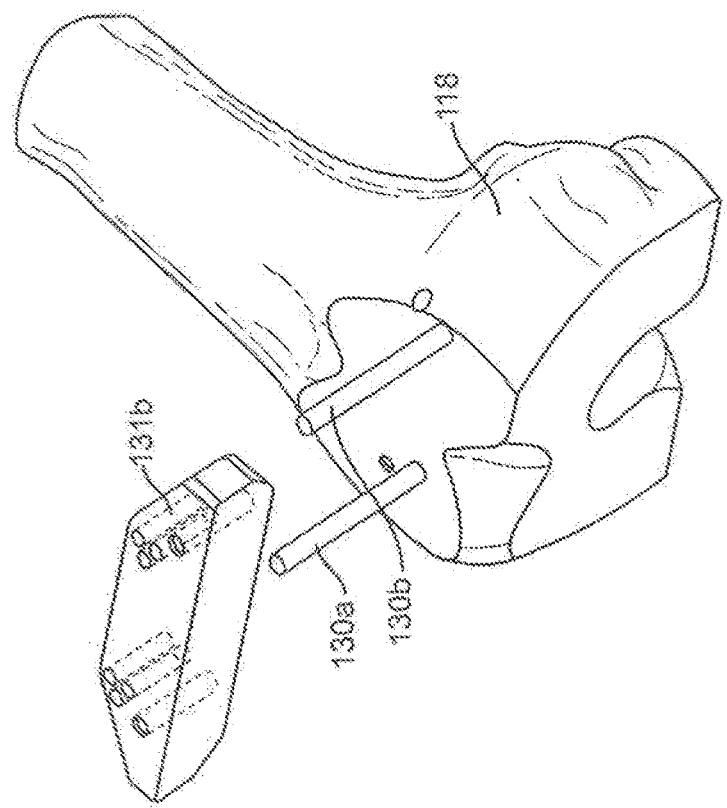

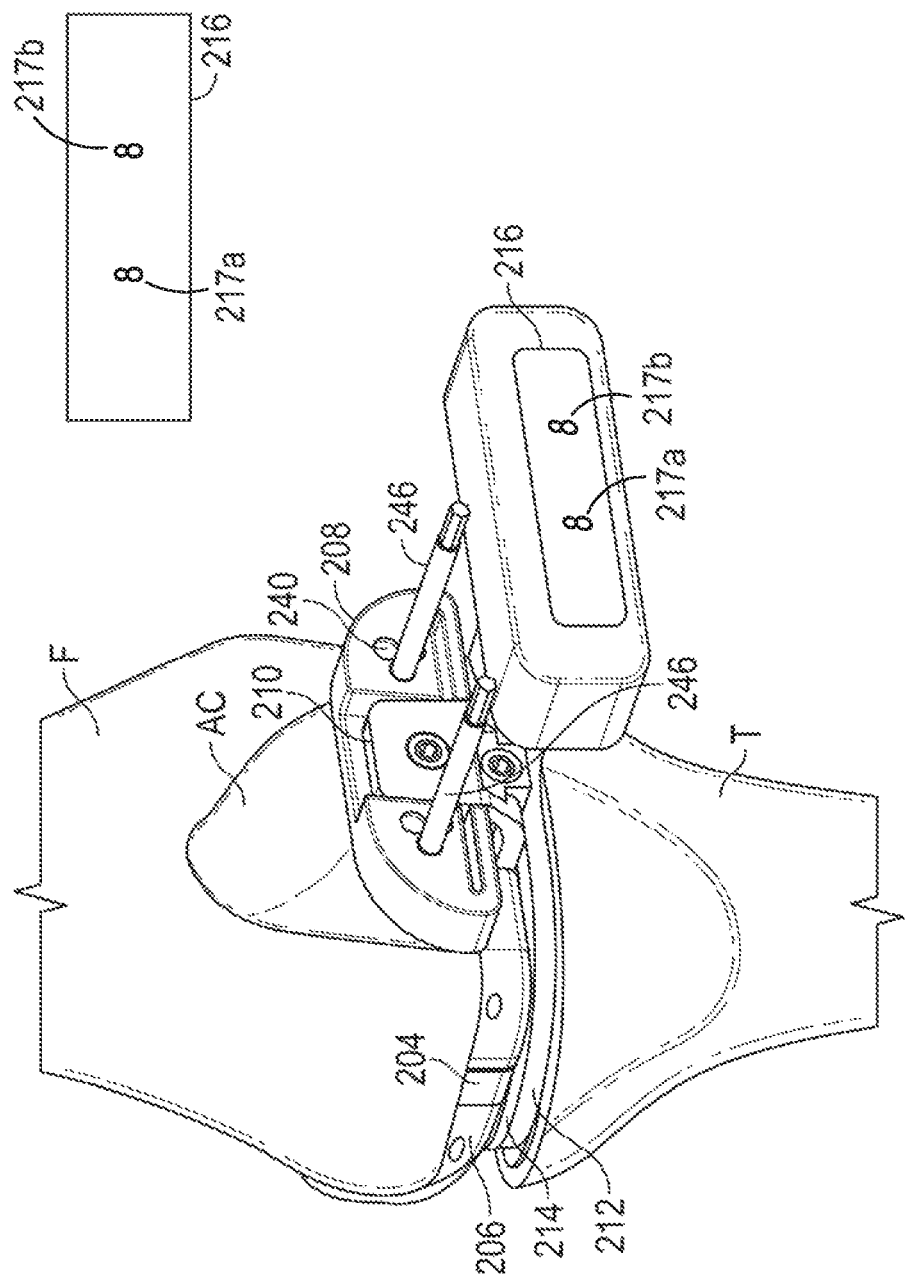

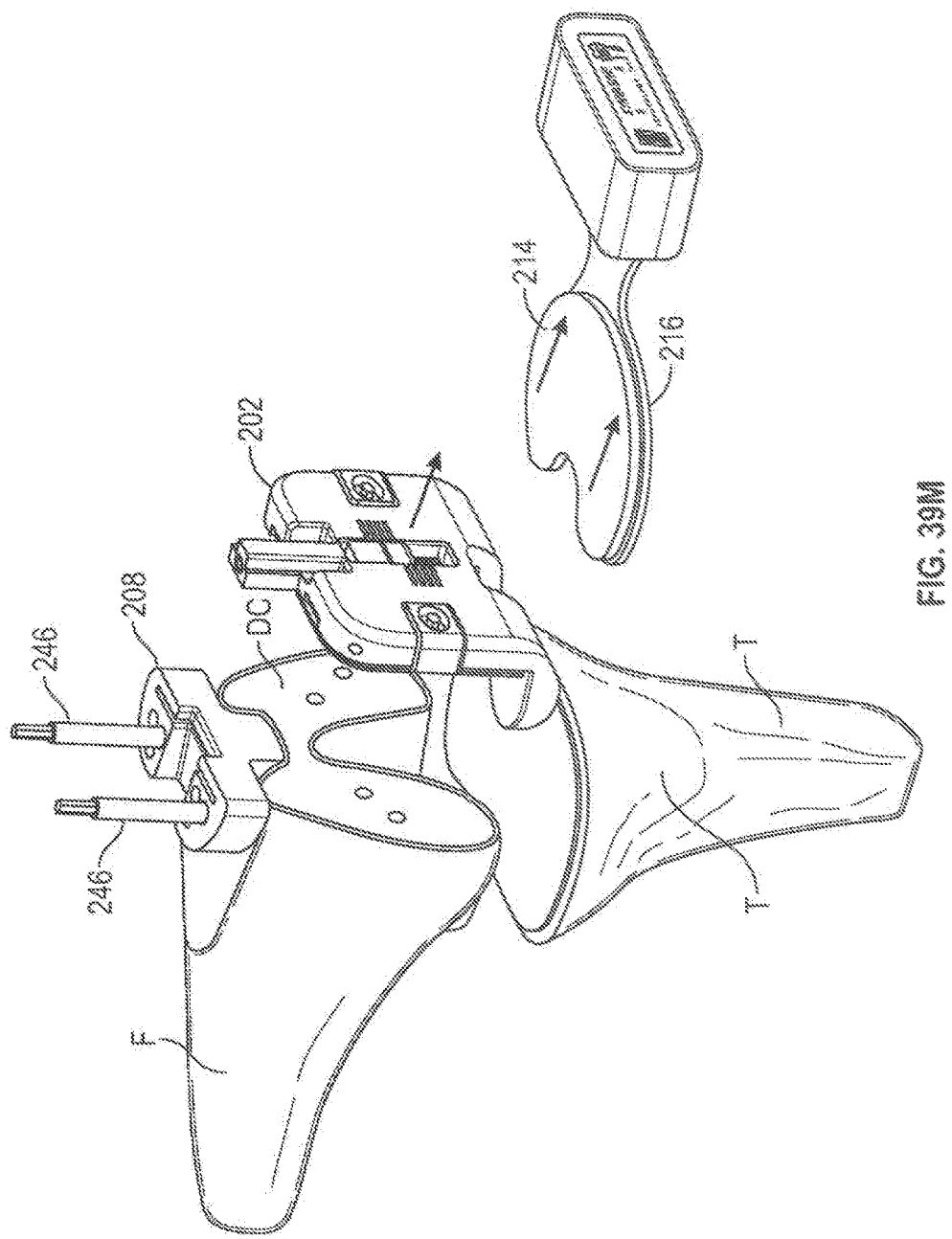

SYSTEM FOR POSITIONING A CUTTING GUIDE IN KNEE SURGERY

CROSS-REFERENCE TO RELATED APPLICATIONS

The present application is a continuation of U.S. patent application Ser. No. 13/524,405, filed Jun. 15, 2012, now issued as U.S. Pat. No. 9,439,656, which is a continuation in part of U.S. patent application Ser. No. 12/609,666, filed Oct. 30, 2009, which claims priority to U.S. Provisional Patent Application Ser. No. 61/109,770, filed Oct. 30, 2008. The full disclosures of these two applications are incorporated herein by reference.

BACKGROUND OF THE INVENTION

Field of the Invention

The present invention relates generally to medical surgical devices, systems, and methods. More specifically, the invention relates to devices, systems and methods for facilitating knee surgery procedures, in particular, knee replacement procedures.

Description of the Related Art

The knee is generally defined as the point of articulation of the femur with the tibia. Structures that make up the knee include the distal femur, the proximal tibia, the patella, and the soft tissues within and surrounding the knee joint, the soft tissues including the ligaments of the knee. The knee is generally divided into three compartments: medial (the inside part of the knee), lateral (the outside part of the knee), and patello-femoral (the joint between the kneecap and the femur). The medial compartment comprises the medial joint surfaces of the femur, tibia, and the meniscus wedged therebetween. The lateral compartment comprises the lateral joint surfaces of the femur, tibia, and the meniscus wedged therebetween. The patellofemoral compartment comprises the joint between the undersurface of the kneecap or patella and the femur. Four ligaments are especially important in the stability, alignment and functioning of the knee—the anterior cruciate ligament, the posterior cruciate ligament, the medial collateral ligament, and the lateral collateral ligament. In an arthritic knee, protective cartilage at the point of articulation of the femur with the tibia is often worn away, allowing the femur to directly contact the tibia. This bone-on-bone contact can cause significant pain, discomfort, and disability for a patient and will often necessitate knee replacement or knee arthroplasty.

Knee arthroplasty involves replacing the diseased and painful joint surface of the knee with metal and plastic components shaped to allow natural motion of the knee. Knee replacement may be total or partial. Total knee replacement surgery, also referred to as total knee arthroplasty ("TKA"), involves a total replacement of the distal end of the femur, the proximal end of the tibia, and often the inner surface of the patella with prosthetic parts. Cuts are made on the distal end of the femur and the proximal end of the tibia. Prosthetic parts are then attached. The prosthetic parts create a stable knee joint that moves through a wide range of motion. The replacement of knee structures with prosthetic parts allows the knee to avoid bone-on-bone contact and provides smooth, well-aligned surfaces for joint movement.

In knee replacement surgeries, it is often vital to restore the mechanical alignment of the knee, i.e., the proper alignment of the mechanical axes of the femur and tibia with each other. Many methods and devices currently are used to restore the mechanical alignment of the leg. These methods and devices are typically used during Total Knee Replacement surgery and include alignment rods, e.g., intramedullary and extramedullary rods, surgical navigation systems, and CT and or MRI based "bone morphing" or "shape-fitting" technologies. Generally, empirical anatomical landmarks are used in these methods. These anatomical landmarks are either directly/mechanically observed intraoperatively, or indirectly relied upon, serving as the foundation of a computer generated reference method. Reference geometry and physical or virtual measurements are often used to ultimately align bone-cutting guides or templates which facilitate bone resections (made with a surgical saw blade). These bone resections will typically properly orient a knee prosthesis in the correct location/alignment. Generally, none of these methods directly take the condition or tendencies of the soft-tissue structures, such as the lateral collateral and medial collateral ligaments, about the knee into consideration.

Historically, surgeons performing total knee replacement surgery in the late 1970s and early 1980s would typically first resect the proximal tibia, creating a flat surface perpendicular to the shaft of the tibia. The leg was then brought to extension. Spacer blocks were shoved between the resected tibia and the uncut distal femur. The spacer blocks were selected from various thicknesses in order to distract the knee joint space to the extent the ligaments about the knee were somewhat taut. Once the knee joint was distracted to that taut condition, a distal femoral cutting guide was positioned in a way to yield a distal femoral bone cut parallel to the tibial cut. It was believed that a distal femoral bone cut, using this method of distracting the joint space between the tibia and femur, would yield proper alignment of the mechanical axis of the leg. This method would often prove successful as practiced by a skilled surgeon and in the case of "passive deformities" of the knee. However, the distraction method would typically not have any accurate means of determining ligament forces between the medial side of the knee and/or the lateral side of the knee. As such, proper alignment would often not be restored. Additionally, the method of first making a proximal tibial bone resection and then making a distal femoral bone resection parallel to the tibial bone resection did not restore proper alignment of the leg in the case of "fixed deformities" of the knee. The case of "fixed deformities" of the knee would otherwise require ligament releases to restore proper alignment of the knee. Accordingly, many early knee replacement surgeons determined that the tibial bone resection and the distal femoral bone resections should be made independent of each other.

As technology has advanced, including the introduction of CT scanners and MRI technology, the thought of computerized bone morphing has gained popularity as a means to accurately place cutting guides. The cutting guides, in turn, are be used in efforts to place prosthetic knee implants in a position in which the knee is properly aligned. Early studies have not found these bone morphing technologies always accurate, reporting proper alignment of the leg was not restored. However, a proper patient selection, e.g., patients with mild, passive deformities of the knee, might be viable candidates for bone morphing technology, assuming those patients/deformities could be property corrected by simple anatomical referencing, as determined by a CT or MRI scan.

However, bone morphing technology is often costly, requiring a CT or MRI scan to determine any given patient's anatomy. Electronic images from such scans must be "filtered" by a computer technician. The "filtered" scan data must be electronically conveyed to some type of fabrication machine, such as a CNC Machining Center or a Rapid Prototype Machine. Ultimately, "shape-matching" and "patient specific" cutting guides must be produced and delivered into surgery.

As such, there is a clear need for systems, devices, and methods of knee surgery that can help surgeons quickly, accurately, and cost-effectively position the distal femoral cutting guide, thus restoring proper alignment and soft-tissue balance of the leg during total knee replacement surgery.

Non-patent literature which may be of interest may include: Murray, David G., "Variable Axis™, Total Knee Surgical Technique," Howmedica Surgical Techniques, Howmedica Inc. 1977; Mihalko, W H et al., "Comparison of Ligament-Balancing Techniques During Total Knee Arthroplasty," Jnl. Bone & Jt. Surg., Vol. 85-A Supplement 4, 2003, 132-135; Eckhoff, D G et al., "Three-Dimensional Morphology and Kinematics of the Distal Part of the Femur Viewed in Virtual Reality, Jnl. Bone & Jt. Surg., Vol. 85-A Supplement 4, 2003, 97-104; and Ries, M D, et al., "Soft-Tissue Balance in Revision Total Knee Arthroplasty," Jnl. Bone & Jt. Surg., Vol. 85-A Supplement 4, 2003, 38-42. Patents of interest may include U.S. Pat. Nos. 4,501,266; 4,646,729; 4,703,751; 4,841,975; 5,116,338; 5,417,694; 5,540,696; 5,597,379; 5,720,752; 5,733,292; 5,800,438; 5,860,980; 5,911,723; 6,022,377 and 6,758,850. Patents applications of interest may include co-assigned U.S. patent application Ser. No. 10/773,608, now U.S. Pat. No. 7,442,196, entitled "Dynamic Knee Balancer"; Ser. No. 10/973,936, now U.S. Pat. No. 7,578,821 entitled "Dynamic Knee Balancer with Pressure Sensing"; Ser. No. 11/149,944 now U.S. Patent Publication Application No. 2005/0267485 A1 entitled "Dynamic Knee Balancer with Opposing Adjustment Mechanism"; 61/090,535 entitled "Sensing Force During Partial and Total Knee Replacement Surgery"; and 61/107, 973 entitled "Dynamic Knee Balancing for Revision Procedures", the entire contents of each of which are incorporated herein by reference.

SUMMARY OF THE INVENTION

The present invention provides devices, systems, and methods for facilitating a surgery performed on a knee, particularly by facilitating the aligning of the knee during a total knee replacement surgery. A femoral assembly is engaged with a distal femur and placed in the gap between the distal femur and proximal tibia. The femoral assembly comprises a stationary portion, an adjustable medial portion, and an adjustable lateral femoral portion. The positions of the medial and lateral femoral portions relative to the stationary portion can be separately adjusted to adjust the varus-valgus alignment of the knee, e.g., the angle between the femur and tibia, as well as the tension in the soft tissues adjacent the knee. Additionally, the femoral assembly comprises adjustable posterior members that fill the posterior capsule of the knee with a thickness similar to the prosthetic femoral implant. Typically, a force sensor will be provided to sense the forces in the medial portion of the knee and the lateral portion of the knee, and the medial and lateral femoral portions will be adjusted so that the sensed forces are balanced. A visual display may be provided to show the surgeon the sensed forces. In addition, a thickness adapter may be provided to removable attach to the force sensor to fill the space between the femur and tibia to the point force readings are obtained. The alignment of the knee can be visually verified using a knee alignment verification member coupled to the femoral assembly, and further verified by angular graduation markings placed upon the femoral stationary portion. The knee alignment verification member may emit laser beams along the mechanical axes of the femur and tibia. Or, alignment rods which align along the mechanical axes of the femur and tibia may be coupled to the knee alignment verification member. The alignment of the knee can be verified using with the laser beams and/or the alignment rods. When the knee is properly aligned, placement pins may be positioned in the distal femur guided by the femoral assembly. The femoral assembly can then be removed and a cutting guide can be positioned on the distal femur based on the position of the placement pins. A cut parallel to a previously made cut on the tibia can then be made on the distal femur. A prosthetic knee placed on these cuts will maintain the proper alignment of the knee.

In a first aspect, the invention provides a system for aligning the knee during a surgical procedure on the knee. The system comprises a femoral assembly that is removably engaged with a distal femur. The femoral assembly includes a stationary femoral portion, an adjustable medial femoral portion (which is coupled to the stationary femoral portion), and an adjustable lateral femoral portion (which is coupled to the stationary femoral portion. A knee alignment verification member is coupled with the stationary femoral portion of the femoral assembly and provides visual confirmation of a femoral and tibial mechanical axes of the knee. A force sensor is coupled with the stationary femoral portion of the femoral assembly. The force sensor comprises a medial portion for sensing a first force in a medial portion of the knee and a lateral portion for sensing a second force in a lateral portion of the knee.

In one embodiment, the knee alignment verification member means includes a laser knee alignment verification member is coupled to the stationary femoral portion. The laser knee alignment provides a first laser beam oriented along the femoral axis of the knee and a second laser beam oriented along the tibial axis of the knee.

In some embodiments, the knee alignment verification member includes a mechanical knee alignment verification assembly. The mechanical knee alignment verification assembly includes a knee alignment hub. A first rod is coupled with the knee alignment hub to be oriented along the femoral axis of the knee and a second rod is coupled with the knee alignment hub to be oriented along the tibial axis of the knee.

In an embodiment, the adjustable medial portion includes a medial paddle and the adjustable femoral portion includes a lateral paddle.

In still other embodiments, the position of the adjustable medial femoral portion relative to the stationary femoral portion is adjustable. The position of the adjustable lateral femoral portion relative to the stationary femoral portion is adjustable.

In other embodiments, the adjustable medial femoral portion and the adjustable lateral femoral portion are separately adjustable.

In some embodiments, a medial rotatable screw couples the adjustable medial femoral portion with the stationary femoral portion. A lateral rotatable screw couples the adjustable lateral femoral portion with the stationary femoral portion.

In some embodiments, rotating the medial rotatable screw adjusts the position of the adjustable medial femoral portion relative to the stationary femoral portion. Rotating the lateral rotatable screw adjusts the position of the adjustable lateral femoral portion relative to the stationary femoral portion.

In some embodiments, the force sensor comprises a force sensing element selected from the group consisting of piezoelectric sensors, force sensing resistors, force sensing capacitors, strain gages, load cells, and pressure sensors.

In still other embodiments, a processor is coupled with the force sensor for processing sensed force data into usable data and for providing the data to a user. A visual display is coupled with the processor and adapted to display the usable data.

In some embodiments, the visual display displays usable data representing a first force sensed in the medial portion of the knee and a second force sensed in the lateral portion of the knee.

In some embodiments, the system for aligning a knee during knee surgery includes a plurality of locating pins. The stationary femoral portion defines at least one medial aperture for positioning at least one locating pin on the distal femur and at least one lateral aperture for positioning at least a second locating pin on the distal femur.

In some embodiments of the invention, a cutting guide is removably engaged with the distal femur. The cutting guide is positioned relative to the distal femur based on the position of at least one first locating pin and the at least a second locating pin.

In some embodiments, the force sensor is removably coupled to a thickness adapter. The adapter fills the space between the femur and tibia.

In some embodiments, the adjustable medial femoral portion and the adjustable lateral femoral portion include a medial fulcrum and lateral fulcrum. The fulcrums are positioned against the provisionally cut distal femur when the distal femoral alignment assembly is mounted against the distal femur. In other embodiments, a bone interface plate is disposed between the fulcrums and the distal femur.

In a second aspect, the invention provides a method for aligning the knee during a surgical procedure on the knee including engaging a femoral assembly with a distal femur. The femoral assembly includes a stationary femoral portion, an adjustable medial femoral portion (coupled to the stationary femoral portion), and an adjustable lateral femoral portion (coupled to the stationary femoral portion). A force sensor is coupled with the stationary femoral portion of the femoral assembly. A first force is sensed in a medial portion of the knee and a second force is sensed in the lateral portion of the knee using the coupled force sensor. The position of the adjustable medial femoral portion can be adjusted separately relative to the stationary femoral portion and the position of the adjustable lateral femoral portion is separately adjustable relative to the stationary femoral portion based on the sensed first and second forces to align a femoral and tibial mechanical axes of the knee. The alignment of the femoral and tibial mechanical axes of the knee are visually confirmed using a knee alignment verification assembly coupled with the stationary femoral portion of the femoral assembly.

In one embodiment, a method for aligning the knee during a surgical procedure on the knee comprises coupling a mechanical knee alignment verification assembly with the stationary femoral member of the femoral assembly. A first alignment rod of the mechanical knee alignment verification assembly is aligned along the femoral axis of the knee and a second alignment rod of the mechanical knee alignment verification assembly is aligned along the tibial axis of the knee. The femoral and tibial mechanical axes of the knee is visually confirmed by the alignment of the first alignment rod and the second alignment rod relative to each other.

In another embodiment, a laser knee alignment verification member is coupled with the stationary femoral member of the femoral assembly. A first laser beam from the laser knee alignment verification member is aligned along the femoral mechanical axis of the knee and a second laser beam from the laser knee alignment verification member is aligned along the tibial mechanical axis of the knee along the tibial axis of the knee, The alignment of the femoral and tibial mechanical axes of the knee is visually confirmed by the alignment of the first laser beam and the alignment of the second laser beam relative to each other.

In some embodiments, the positions of the adjustable medial femoral portion relative to the stationary femoral portion and of the adjustable lateral femoral portion relative to the stationary femoral portion are adjusted based on the sensed first force and the sensed second force so that the first and second forces are balanced.

In some embodiments, the first force in a medial portion of the knee is sensed and a second force in a lateral portion of the knee is sensed using the coupled force sensor. This includes transmitting a voltage to a sensor element of a thin force sensing portion of the force sensor and measuring the voltage after it has passed through the sensor element. The percentage of the voltage that passed through the sensor element is determined relative to the voltage transmitted to the sensor element. The measured force is derived from the percentage.

In yet another embodiment, the sensed first force and the sensed second force is visually displayed by a display coupled to the force sensor.

In some embodiments, separately adjusting the position of the adjustable medial femoral portion relative to the stationary femoral portion and the position of the adjustable lateral femoral portion relative to the stationary femoral portion comprises rotating at least one of a lateral rotatable screw coupling the adjustable lateral femoral portion to the stationary femoral portion and a medial rotatable screw coupling the adjustable medial femoral portion to the stationary femoral portion.

In some embodiments, the stationary femoral portion defines at least one medial aperture and at least one lateral aperture. The method further includes positioning at least one locating pin on the distal femur based on at least one medial aperture and positioning at least a second locating pin on the distal femur based on the at least one lateral aperture.

In an embodiment, the femoral assembly is disengaged with the distal femur and engages a distal femoral cutting guide with the distal femur. The distal femoral cutting guide is positioned relative to the distal femur based on the position of at least one first and at least one second locating pins.

In some embodiments, cuts are made on the distal femur based on the position of the distal femoral cutting guide.

In another aspect, the invention provides a method for aligning a leg during knee surgery. The leg has a femur and a tibia. The femur has a mechanical axis, a distal end and a proximal end. The tibia has a mechanical axis, a distal end and a proximal end. The method of aligning the leg includes engaging a femoral assembly with the provisionally cut distal end of the femur. The femoral assembly includes a stationary femoral portion, an adjustable medial femoral portion that has a medial pivot fulcrum coupled to the stationary femoral portion, and an adjustable lateral femoral portion that has a lateral pivot fulcrum coupled to the stationary femoral portion. A force sensor is coupled with the stationary femoral portion of the femoral assembly. A medial posterior member is reversibly coupled to the medial side of the stationary femoral portion. A lateral posterior member is reversibly coupled to the lateral side of the stationary femoral portion. The medial member abuts the medial posterior femur and the lateral member abuts the lateral posterior femur. A first force is sensed in a medial portion of the knee and a second force is sensed in the lateral portion of the knee using the force sensor. The position of the adjustable medial femoral portion is adjusted relative to the stationary femoral portion and the position of the adjustable lateral femoral portion is (separately) adjusted relative to the stationary femoral portion based on the sensed first and second forces to align the femoral and tibial mechanical axes of the knee. The alignment of the femoral and tibial mechanical axes of the knee is visually confirmed using a knee alignment verification assembly which is coupled with the stationary femoral portion of the femoral assembly.

In one embodiment, the medial member abuts the medial posterior femur and the lateral member abuts the lateral posterior femur when the leg is fully extended.

In some embodiments, the medial and lateral fulcrums determine fixed distance points to adjust an angle.

In some embodiments, a bone interface plate is disposed between the adjustable medial and lateral femoral portions and the distal femur.

In another aspect, a system for positioning a cutting guide on a femur of a knee to make a cut along a distal end of the femur during a surgical procedure on the knee may include: an adjustable femoral attachment member configured to attach to a cut distal end of the femur a cutting guide removably attachable to the femoral attachment member and configured to guide a surgical saw to make an additional cut on the distal end of the femur; and a force sensor for positioning between the femoral attachment member and a proximal end of a tibia of the knee, wherein the force sensor comprises a medial portion for sensing a medial force in the knee and a lateral portion for sensing a lateral force in the knee. The femoral attachment member may include: a medial elevator for increasing an amount of space between a medial portion of the femoral attachment member and the cut distal end of the femur; a lateral elevator for creating space between a lateral portion of the femoral attachment member and the cut distal end of the femur; and a single adjustment member configured to adjust both the medial and lateral elevators;

In some embodiments, the system may also include one or more inserts for positioning between the force sensor and the femoral attachment member in the knee. The system may also optionally include multiple pins for attaching the cutting guide to the femur and/or multiple screws for attaching the femoral attachment member to the femur. In one embodiment, the femoral attachment member may include at least two screw holes on a distal-facing surface for accepting the screws. Optionally, the system may also include an indicator on the distal-facing surface for indicating an angle of resection to which the cutting guide has been adjusted.

The system may further include an adjustment device for adjusting the femoral attachment member. For example, the adjustment device in one embodiment may be a wrench configured to turn the adjustment member in one direction to adjust the medial elevator and in an opposite direction to adjust the lateral elevator. In some embodiments, the system may also include a slide member removably coupled with the cutting guide so that the cutting guide and slide member can slide onto the femoral attachment member to contact an anterior side of the femur.

In some embodiments, the femoral attachment member may be configured to be attached to the cut distal end of the femur while the knee is in flexion. In such embodiments, the femoral attachment member may also be configured to remain attached to the cut distal end of the femur while the knee is moved from flexion to extension. In some embodiments, the system may further include a display coupled with the sensor, configured to display a first indicator representing the medial force and a second indicator representing the lateral force.

In another aspect, a method for positioning a cutting guide on a femur of a knee to make a cut along a distal end of the femur during a surgical procedure on the knee may involve: attaching an adjustable femoral attachment member with a cut distal end of the femur; positioning a force sensor on a cut proximal end of a tibia of the knee; attaching the cutting guide to the femoral attachment member; adjusting the femoral attachment member, using a single adjustment member of the femoral attachment member, to elevate at least one of a medial side and a lateral side of the femoral attachment member relative to the cut distal end of the femur to approximately balance medial and lateral forces displayed on a display coupled with the sensor, wherein adjusting the femoral attachment member changes a position of the cutting guide relative to the femur; and attaching the cutting guide to the femur.

In some embodiments, attaching the femoral attachment member may involve advancing two screws through holes in the attachment member and into the cut distal end of the femur while the knee is in flexion. Optionally, the method may also include positioning an insert between the force sensor and the femoral attachment member. The method may further involve moving the knee into extension while the femoral attachment member remains attached to the femur and before adjusting the femoral attachment member. In such an embodiment, the cutting guide may remain attached to the femur while the knee is in extension. In some embodiments, attaching the cutting guide involves pinning the cutting guide to the femur using multiple pins.

The method may further involve moving the knee back into flexion after the cutting guide is attached. In one embodiment, the method may further include viewing a resection angle indicator on a distal surface of the femoral attachment member while the knee is in flexion, where the resection angle indicator indicates approximately an angle of resection of the distal femur based on a position of the cutting guide. In some embodiments, attaching the cutting guide to the femoral attachment member may involve sliding the cutting guide, attached to a slide member, onto the femoral attachment member until the cutting guide contacts a cut anterior surface of the femur. Optionally, the method may further involve, before attaching the cutting guide to the femoral attachment member, attaching the slide member to the cutting guide. For example, attaching the slide member to the cutting guide may involve tightening a first screw using an adjustment device, and adjusting the femoral adjustment member may involve turning a second screw using the same adjustment device.

Optionally, the method may further involve, before attaching the femoral adjustment member, making initial cuts on the distal end of the femur, an anterior side of the femur and a posterior side of the femur. In some embodiment, the single adjustment member may be a screw, and adjusting the femoral adjustment member may involve using an adjustment device to turn the screw in a first direction to adjust the medial side of the adjustment member and in a second direction to adjust the lateral side of the adjustment member. In some embodiments, the method may also optionally involve removing the femoral attachment member from the femur and the sensor from the tibia and cutting the distal end of the femur, using the attached cutting guide. In some embodiments, the method may further include removing a slide member attached to the cutting guide before cutting the distal end of the femur.

In another aspect, a method for making a cut on a distal end of a femur during a surgical procedure on a knee may include: attaching an adjustable femoral attachment member with the distal end of the femur on which initial distal, anterior and posterior cuts have previously been made, while the knee is in flexion; positioning a force sensor coupled with an insert on a cut proximal end of a tibia of the knee; sliding a cutting guide onto the femoral attachment member until it contacts a cut anterior side of the femur; tightening the cutting guide onto the femoral attachment member; moving the knee into extension; adjusting the femoral attachment member, using a single adjustment member of the femoral attachment member, to balance medial and lateral forces displayed on a display coupled with the sensor, wherein adjusting the femoral attachment member changes a position of the cutting guide relative to the femur; attaching the cutting guide to the femur; moving the knee into flexion; removing the femoral attachment member from the femur; and making the cut on the distal end of the femur, using the cutting guide.

In some embodiments, adjusting the femoral attachment member may involve turning the single adjustment member using an adjustment device in at least one of a first direction, to adjust the medial force, and a second direction, to adjust the lateral force. In some embodiments, tightening the cutting guide may involve using the adjustment device to tighten a screw attaching the cutting guide to the femoral attachment member. In some embodiments, sliding the cutting guide onto the femoral attachment member may involve sliding a slide member attached to the cutting guide along the femoral attachment member. In these embodiments, the method may optionally further involve removing the slide member from the cutting guide before making the cut on the distal end of the femur. The method may also further involve viewing a resection angle indicator on the femoral attachment member after moving the knee into flexion to approximate a resection angle before making the cut. In some embodiments, the method may also involve removing the sensor and the insert from the tibia before making the cut on the distal end of the femur.

In another aspect, a device for positioning a cutting guide on a femur of a knee during a surgical procedure on the knee, may include: a stationary femoral member that attaches to a cut distal end of the femur; an adjustable femoral member moveably attached to the stationary femoral member; a medial elevator for creating space between the stationary and adjustable femoral members closer to a medial edge of the device than a lateral edge of the device; a lateral elevator for creating space between the stationary and adjustable femoral members closer to the lateral edge of the device than the medial edge of the device; and a single adjustment member configured to adjust both the medial and lateral elevators.

In some embodiments, the device may further include a cutting guide removably attachable to the adjustable femoral member and configured to guide a surgical saw to make an additional cut on the distal end of the femur. In some embodiments, the device may include a force sensor for positioning between the adjustable femoral member and a proximal end of a tibia of the knee. The force sensor may include a medial portion for sensing a medial force in the knee and a lateral portion for sensing a lateral force in the knee. Some embodiments may further include a display coupled with the sensor and configured to display a first indicator representing the medial force and a second indicator representing the lateral force. Some embodiments may also further include an insert for positioning between the force sensor and the femoral attachment member in the knee. In some embodiments, the device may include multiple screws for attaching the stationary femoral member to the femur.

In some embodiments, the device may include an indicator on a distal-facing surface of the adjustable femoral member fir indicating an angle of resection to which the cutting guide has been adjusted. The device may also include an adjustment device for adjusting the medial and lateral elevators via the single adjustment member. In some embodiments, the adjustment device may include a wrench configured to turn the adjustment member in one direction to adjust the medial elevator and in an opposite direction to adjust the lateral elevator. In some embodiments, the single adjustment member may include a sliding portion that slides in a first direction to elevate the medial elevator and in a second, opposite direction to elevate the lateral elevator, in many embodiments, the device may be configured to be attached to the cut distal end of the femur while the knee is in flexion. In some embodiments, the femoral attachment member may be configured to remain attached to the cut distal end of the femur while the knee is moved from flexion to extension.

These and other aspects and embodiments are described in greater detail below, in reference to the drawings.

BRIEF DESCRIPTION OF THE DRAWINGS

FIG. 24A-B shows exploded views of a knee alignment system according to embodiments of the invention.

FIGS. 27-35 show an alternative method of aligning a knee surgery according to embodiments of the invention.

DETAILED DESCRIPTION

Embodiments of the present invention provide systems, devices, and methods for facilitating the alignment and balancing of the knee during knee replacement surgery and verifying such balance and alignment. Once the knee is properly aligned, a cut parallel to a previously made cut on the tibia can be made on the distal femur. A prosthetic knee placed on these cuts will maintain the proper alignment of the knee.

Figure 1:
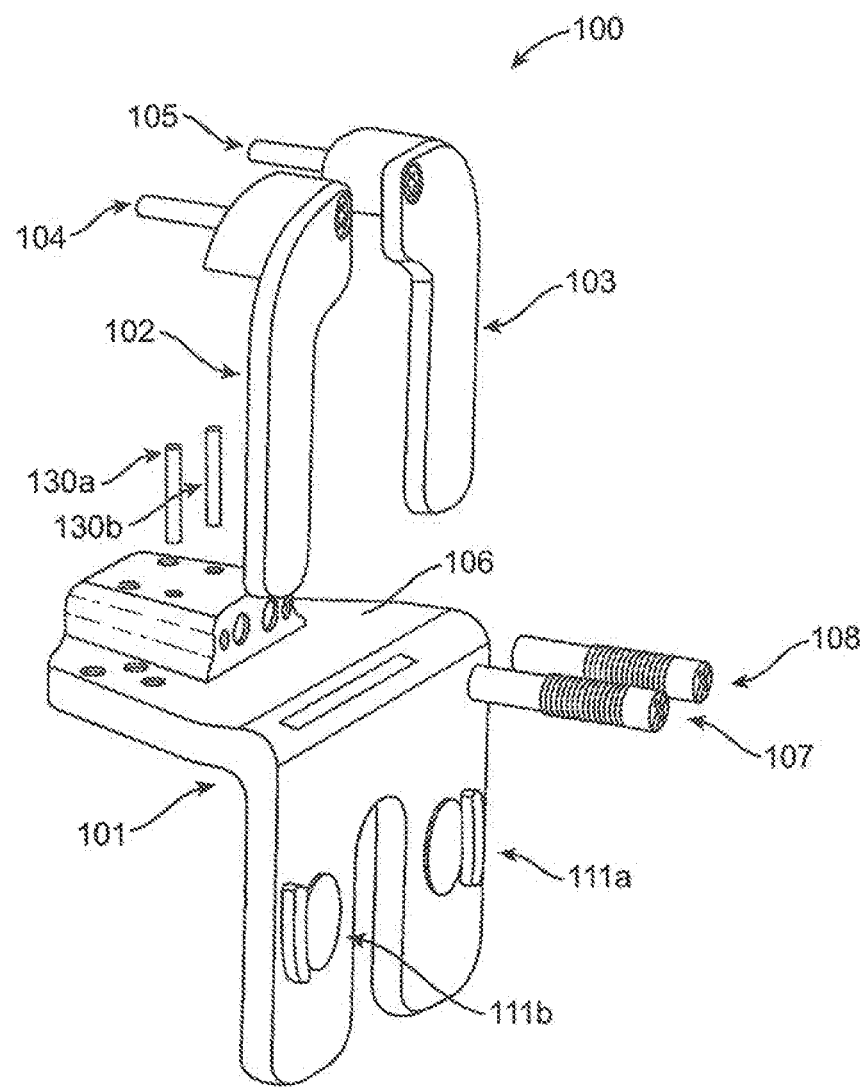
FIG. 1 shows an exploded view of a distal femoral alignment component assembly according to embodiments of the invention.

Referring now to FIG. 1, a distal femoral alignment assembly or component 100 according to embodiments of the invention is shown in an exploded view. As shown in FIG. 1, distal femoral alignment assembly 100 can be used for either the left or right knee, i.e., one side of the distal femoral alignment assembly may be the medial side while the other is the lateral side and vice versa. Distal femoral alignment assembly 100 comprises a main body 101, an adjustable medial femoral portion coupled to the main body, and an adjustable lateral femoral portion coupled to the main body. When the distal femoral alignment assembly 100 is coupled to a distal femur, the main body or stationary portion of the distal femoral alignment assembly is generally stationary with respect to the adjustable medial and lateral femoral portions. The adjustable medial and lateral femoral portions are adjusted with respect to the main body. Adjustable medial and lateral femoral portions respectively comprise medial and lateral paddles 102, 103. The medial and lateral paddles each comprise anti-rotation shafts 104, 105 which fit into slots 106 of the main body. Medial and lateral distraction screws 107, 108 respectively couple the medial and lateral paddles 102, 103 with the main body 101. Distraction screw capture pegs 109, 110 fix the axial position of the distraction screws 107, 108 relative to the main body 101 such that rotation of the medial and lateral distraction screws only adjusts the positions of the adjustable medial and lateral femoral portions with respect to the main body 101. The main body comprises mounts for attachment of a force sensor 111.

Figure 2:
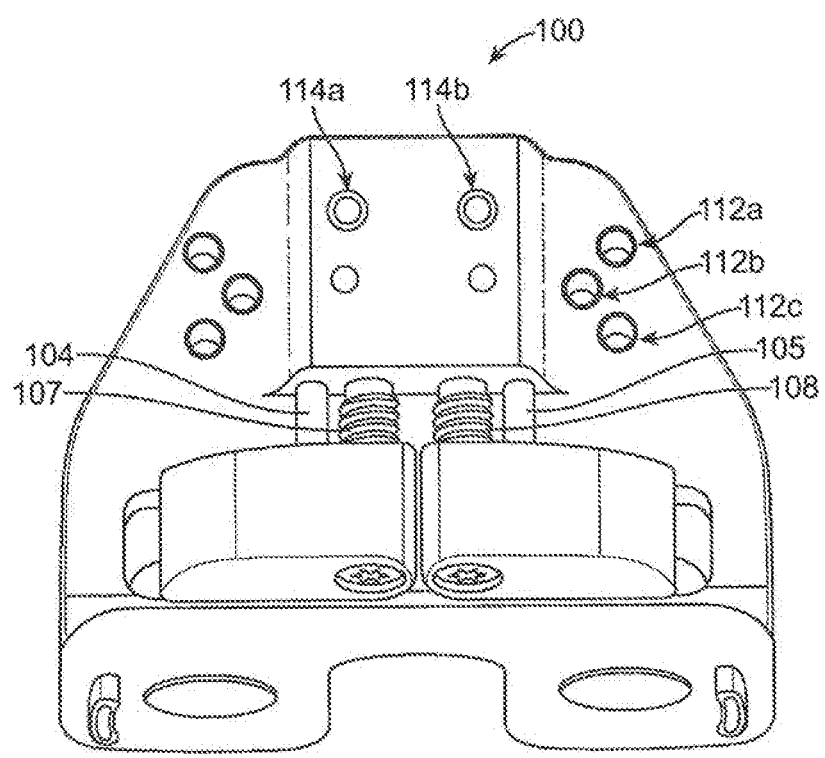
FIG. 2 shows a top view of the unadjusted distal femoral alignment assembly of FIG. 1.

Referring now to FIG. 2, the main body 101 of the distal femoral adjustment assembly 100 further defines cutting guide locating apertures on its medial 113a-c and lateral 112a-c sides. These apertures are cutting guide locating means, e.g., by facilitating the placement of placement pins from which provide points of reference for the placement of a cutting guide. The main body further defines slots or verification attachment slots or apertures 114a, 114b for attaching a knee alignment verification means as described below.

Figure 3:
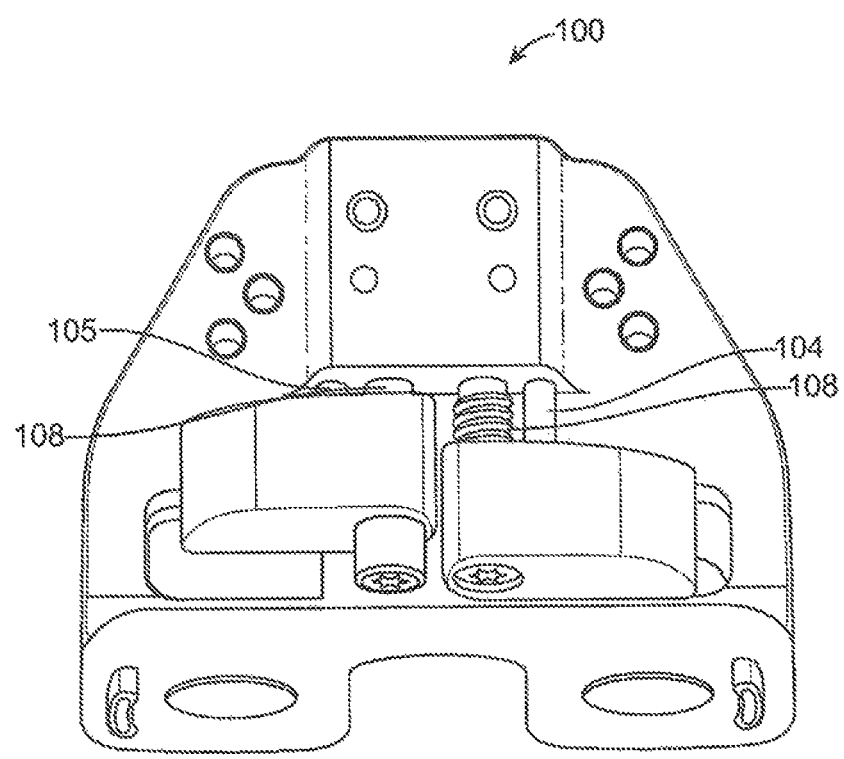
FIG. 3 shows a top view of the adjusted distal femoral alignment assembly of FIG. 1.
Figure 4:
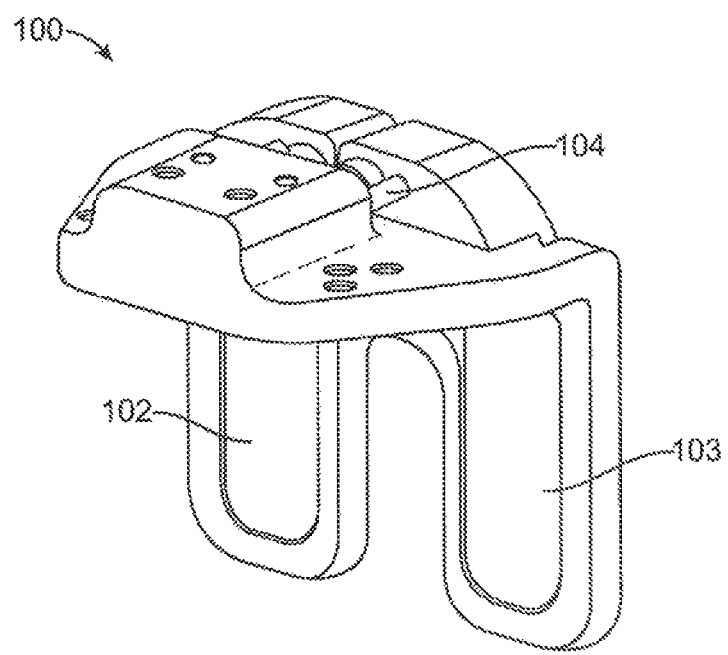
FIG. 4 shows a perspective view of the unadjusted distal femoral alignment assembly of FIG. 1.
Figure 5:
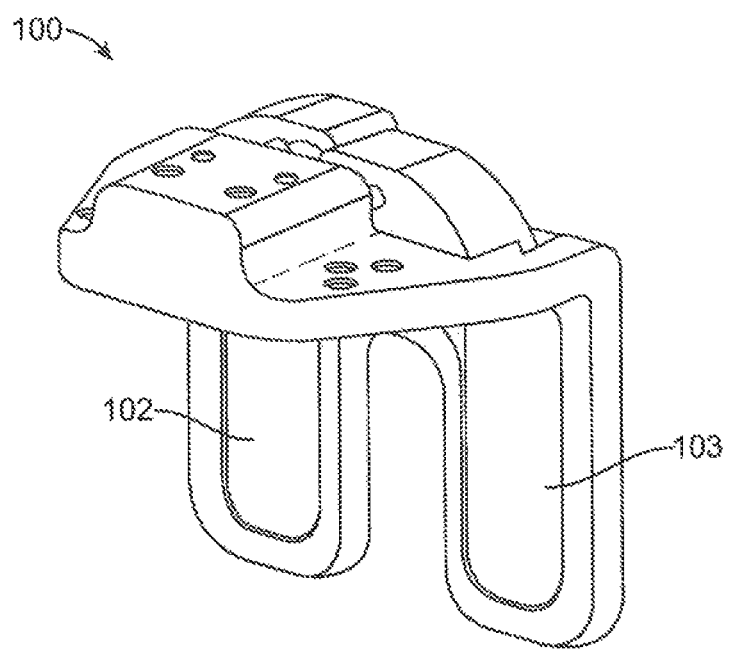
FIG. 5 shows a perspective view of the adjusted distal femoral alignment assembly of FIG. 1.

FIGS. 2 and 4 show the distal femoral adjustment assembly 100 unadjusted. FIGS. 3 and 5 show the distal femoral adjustment assembly 100 adjusted, i.e., the position of one paddle of the distal femoral adjustment assembly has been moved relative to the other.

Figure 6:
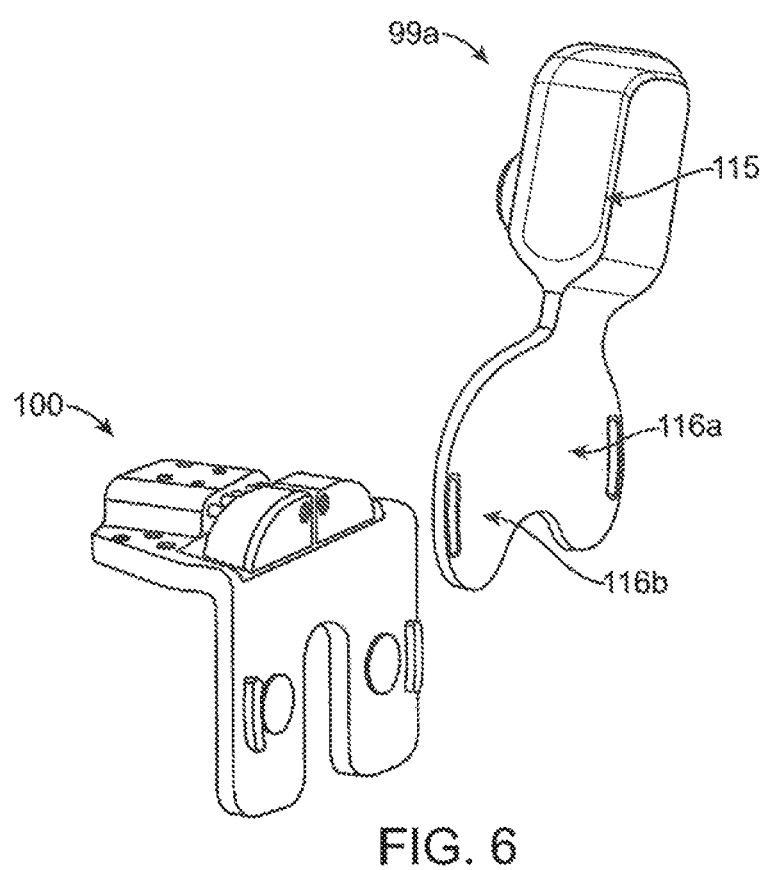
FIGS. 6 and 7 shows perspective views of a knee alignment system according to embodiments of the invention.
Figure 7:
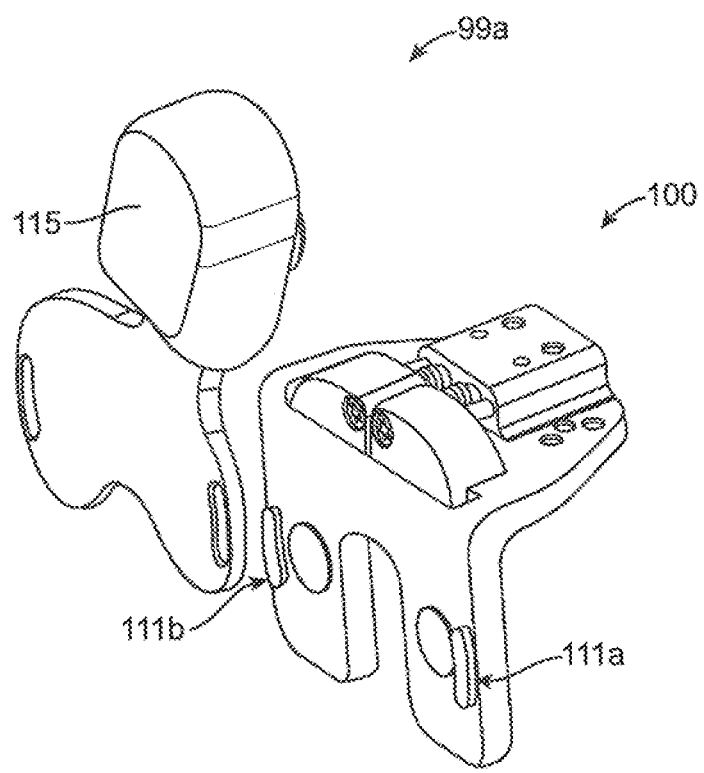

FIGS. 6 and 7 show a perspective view of a knee alignment system 99a according to embodiments of the invention. The system comprises the distal femoral adjustment assembly 100 as described above. The system further comprises a electronic force-sensing means or force sensor 115 coupleable with the distal femoral adjustment assembly 100. As shown, the force sensor 115 comprises a handheld tool but may alternatively be a smaller device coupleable with the main body of the distal femoral adjustment assembly 100. The force sensor 115 senses the force between the medial portion of the distal femur and the medial portion of the tibial plateau as well as the force between the lateral portion of the distal femur and the lateral portion of the tibial plateau, for example, by comprising first and second force sensing portions 116a, 116b, the first force sensing portion 116a being a lateral force sensing portion while the second 116b is a medial force sensing portion and vice versa. The distal femur and tibial plateau are not shown in FIGS. 6-7. The force sensor 115 may be similar to those described U.S. Patent Applications No. 61/090,535 entitled "Sensing Force During Partial and Total Knee Replacement Surgery" and 61/107,973 entitled "Dynamic Knee Balancing for Revision Procedures", the entireties of which had been previously incorporated herein by reference.

Figure 8:
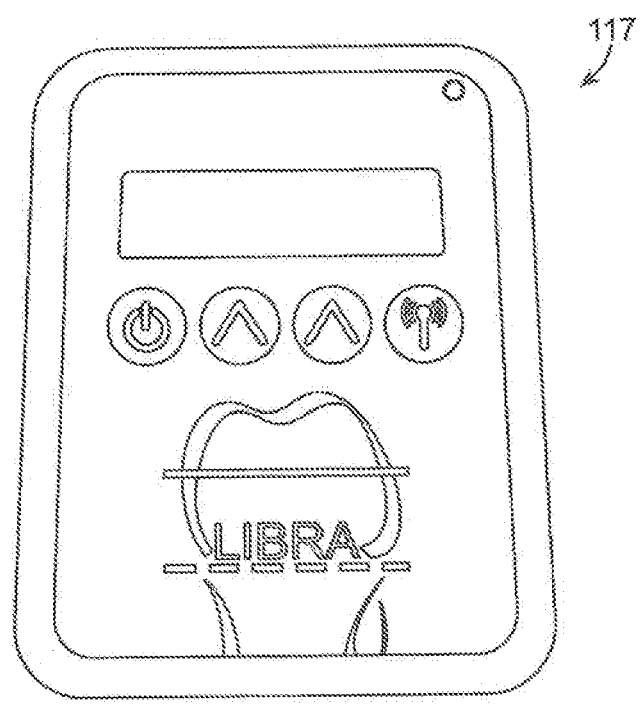
FIG. 8 shows a visual display of a knee alignment system according embodiments of the invention.

FIG. 8 shows a visual display 117 coupleable with the force sensor 115. The visual display displays data representative of the force sensed by the force sensor and may be similar to those described in U.S. patent application Ser. No. 10/973,936, now U.S. Pat. No. 7,578,821, entitled "Dynamic Knee Balancer with Pressure Sensing"; 61/090,535 entitled "Sensing Force During Partial and Total Knee Replacement Surgery"; and 61/107,973 entitled "Dynamic Knee Balancing for Revision Procedures", the entireties of which had been previously incorporated herein by reference.

Figure 9:
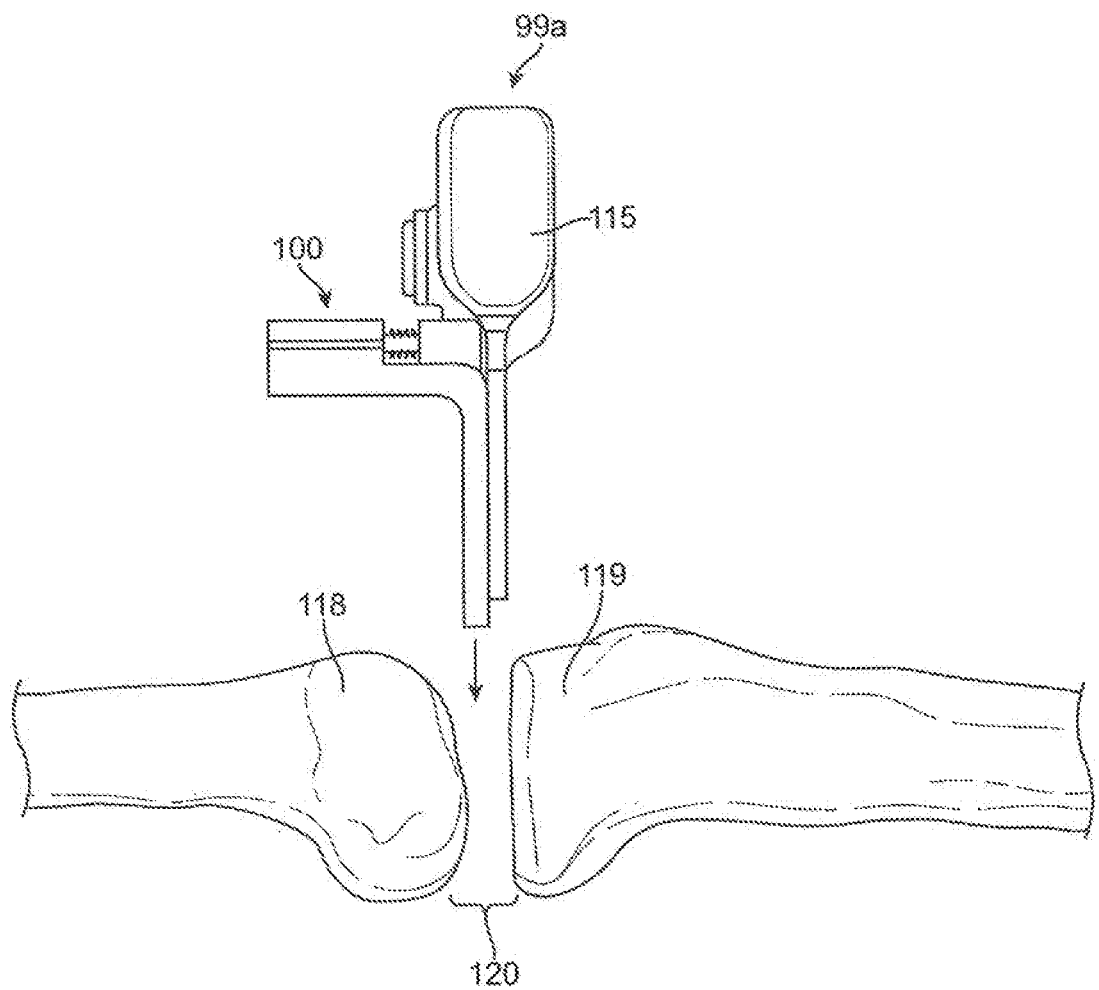
FIGS. 9-10 show a side view of a knee alignment system, including the distal femoral alignment component and the force sensor coupled together, being placed in the gap.
Figure 10:
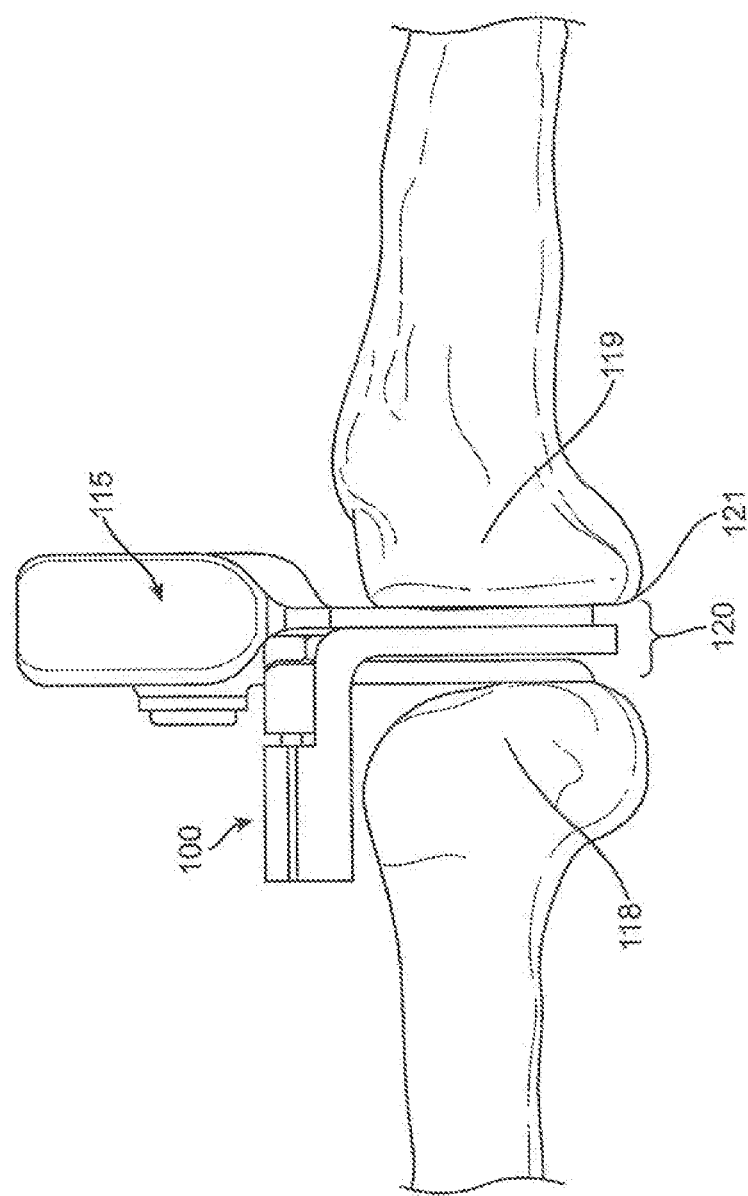
Figure 11:
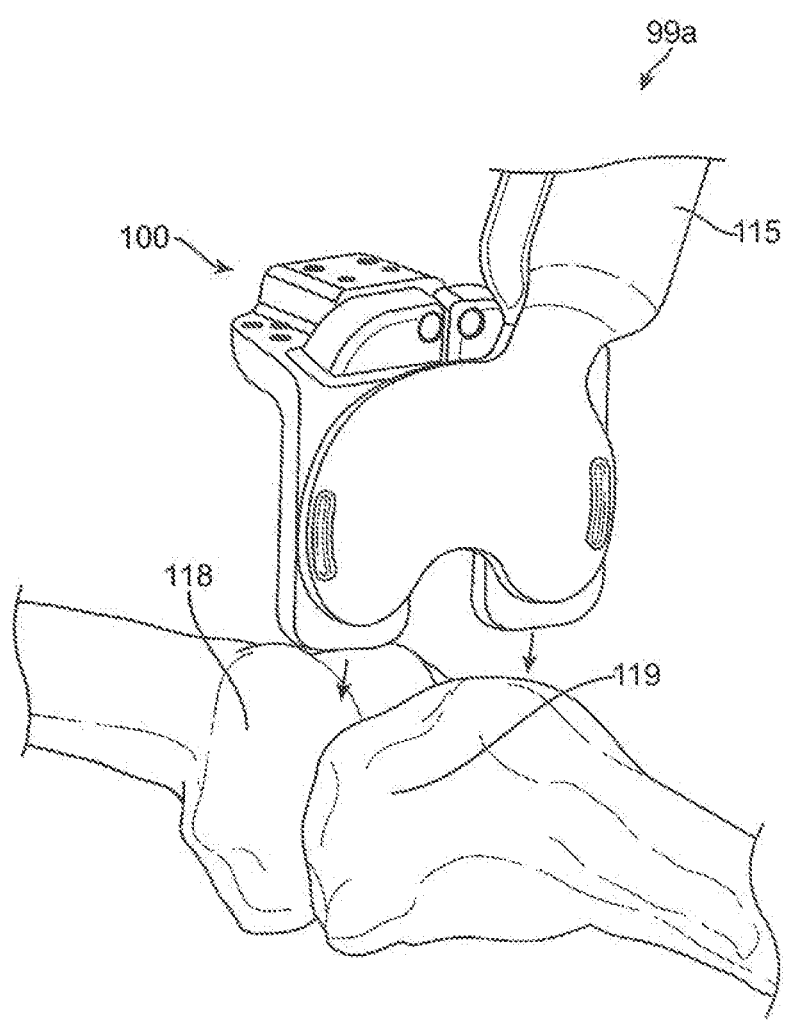
FIGS. 11-12 show a perspective view of a knee alignment system, including the distal femoral alignment component and the force sensor coupled together, being placed in the gap.
Figure 12:
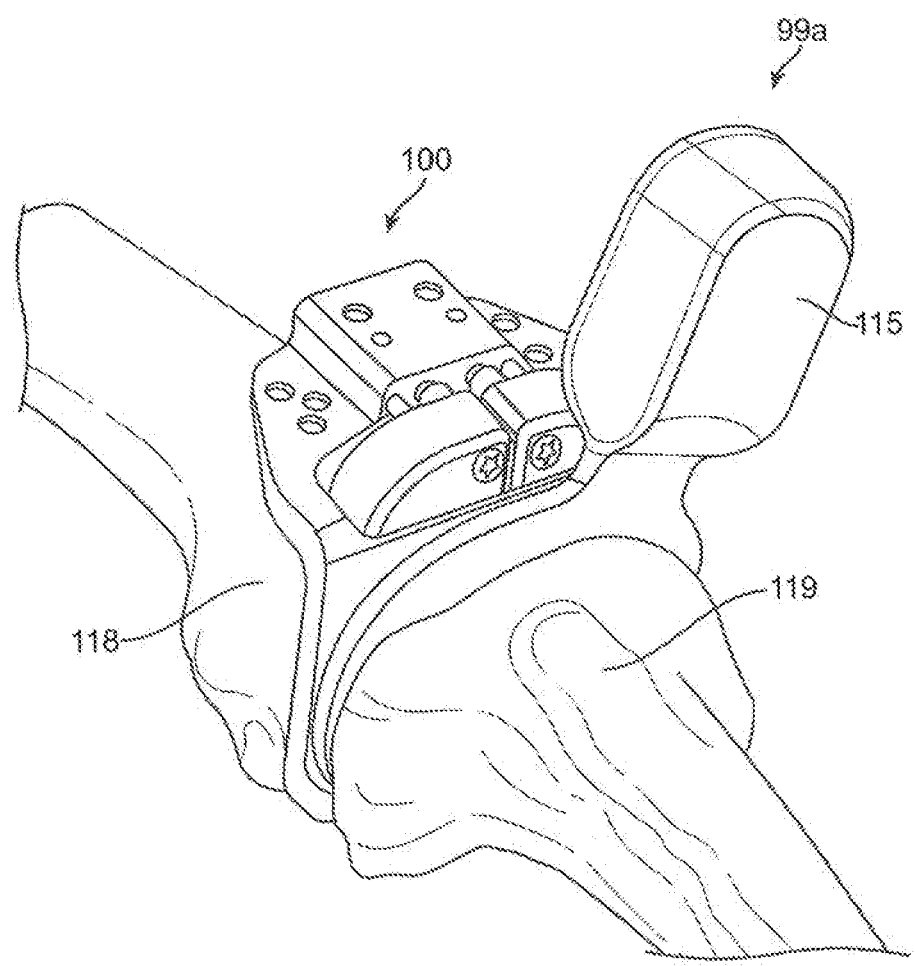
Figure 13:
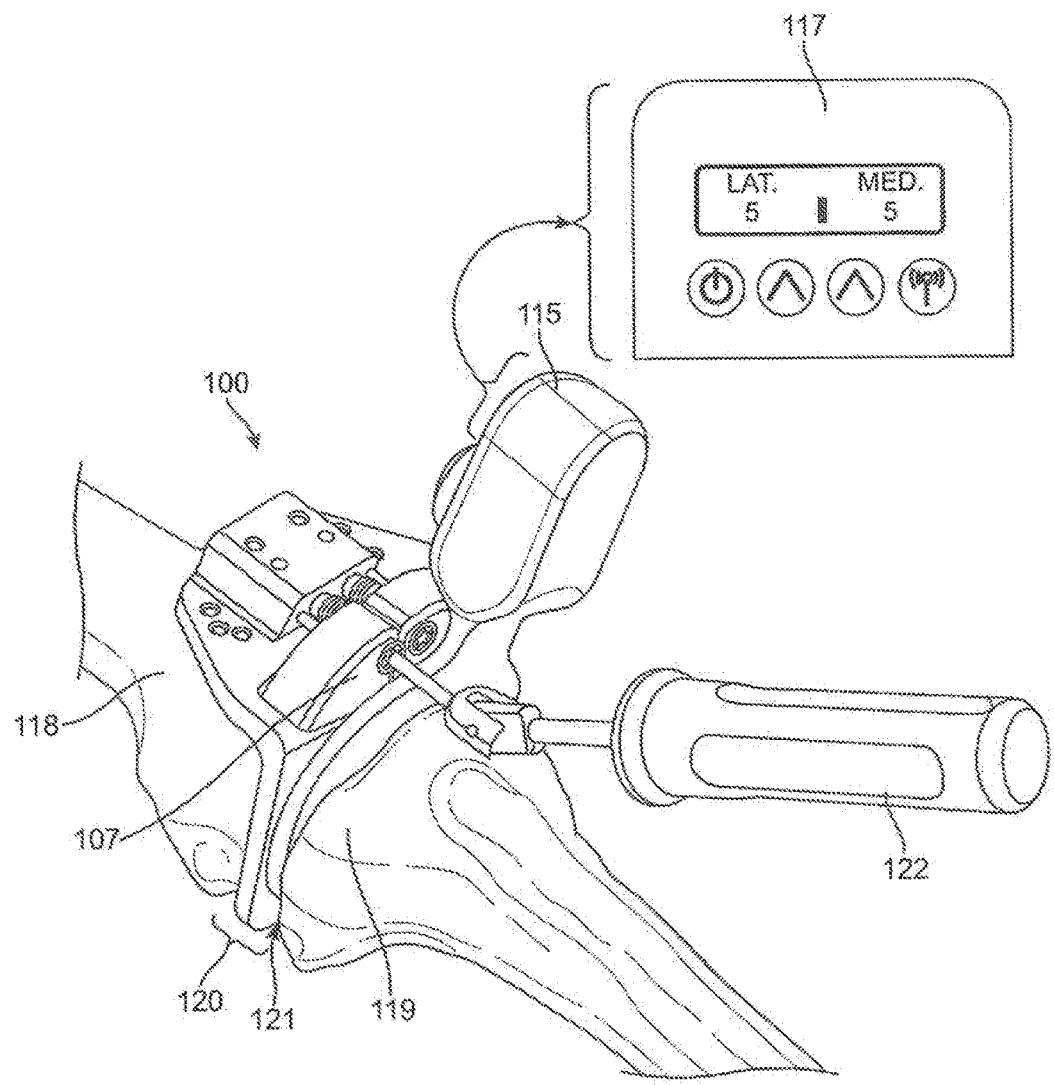
FIGS. 13-23 show a method of aligning a knee during surgery according to embodiments of the invention.
Figure 14:
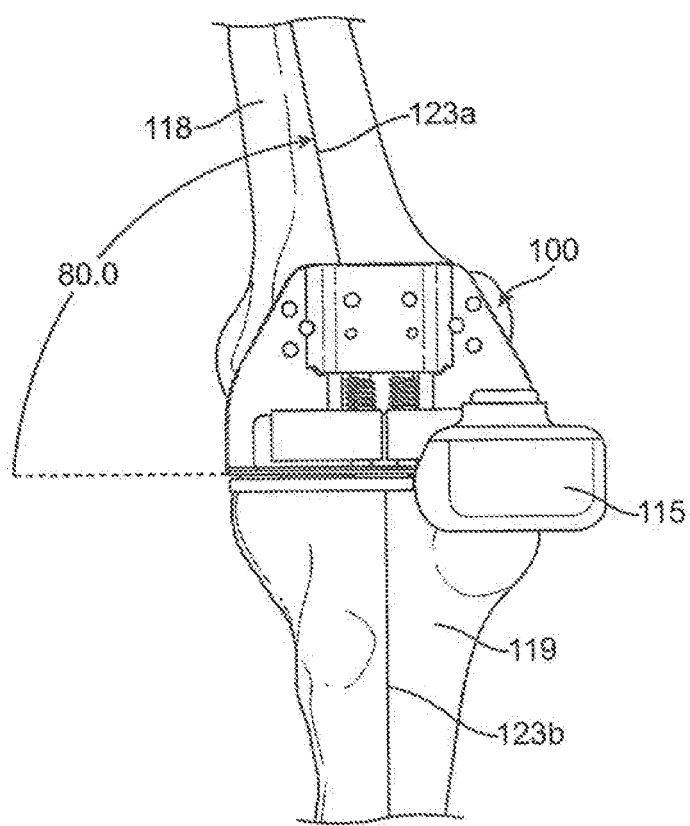
Figure 15:
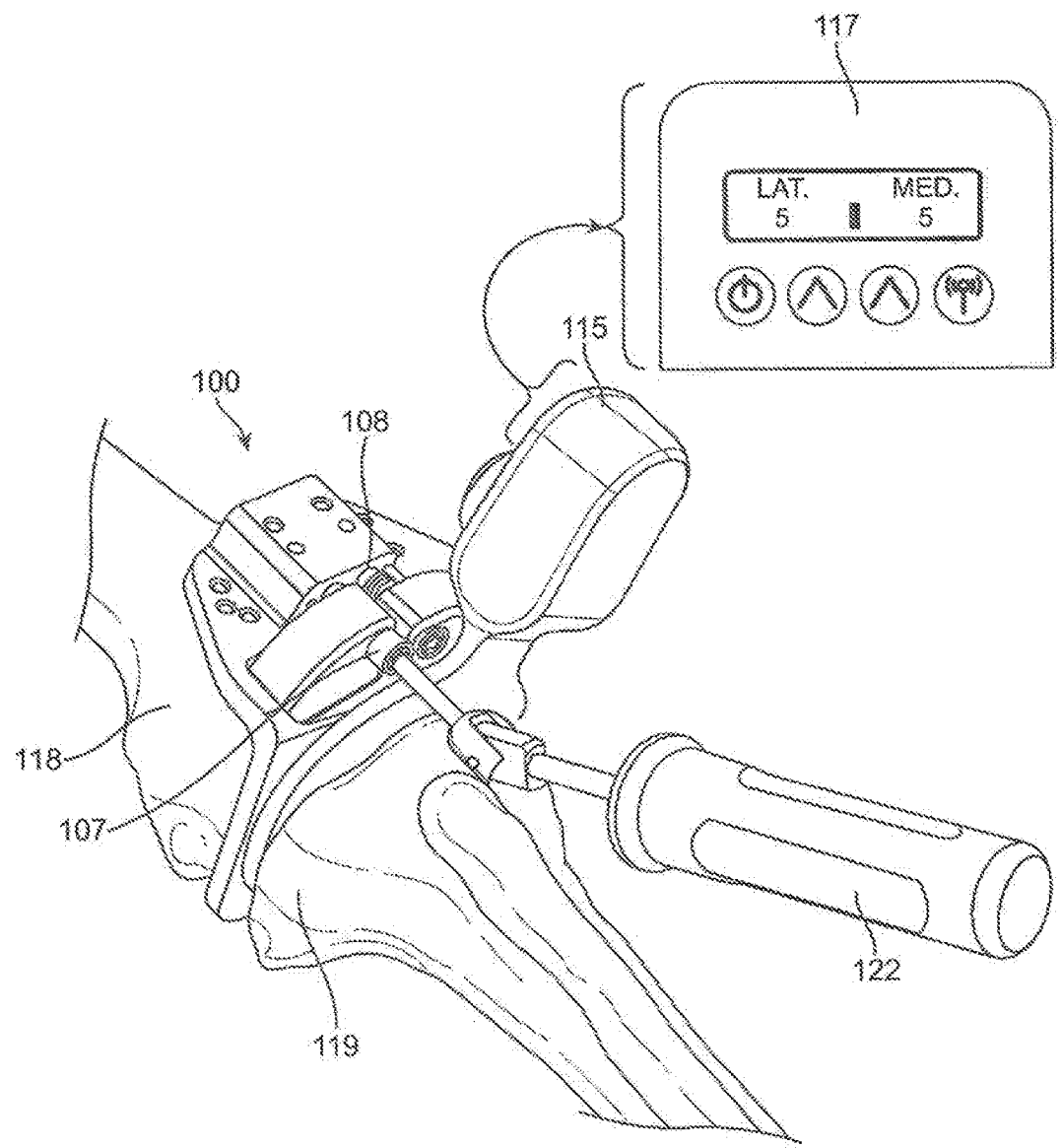
Figure 16:
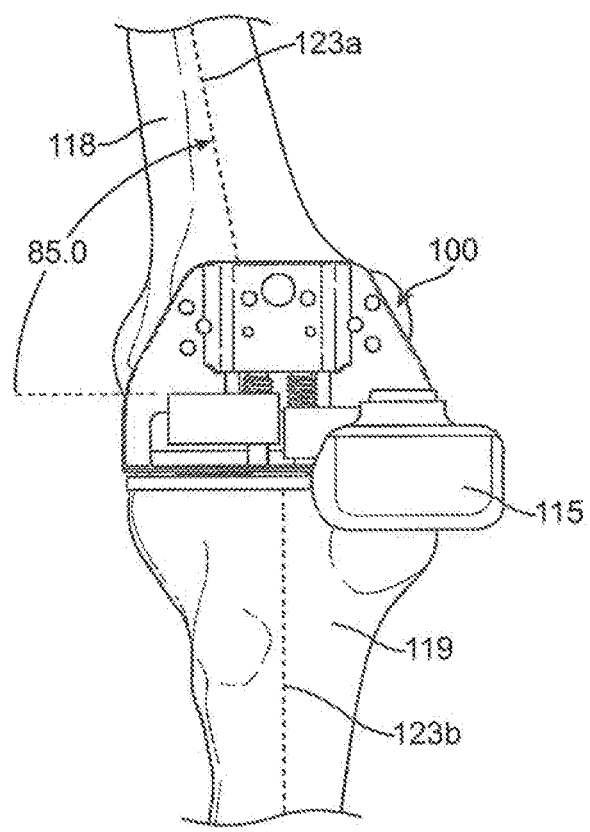

FIGS. 9-23 show a method of using an exemplary knee alignment system during knee replacement surgery according to embodiments of the invention. As shown in FIGS. 9 and 11, the force sensor 115 is coupled to the distal femoral alignment assembly 100. As shown in FIGS. 10 and 12, the distal femoral alignment assembly 100 and the coupled force sensor 115 are placed in the gap 120 between the distal femur 118 and the tibial plateau 121 of the knee. As shown in FIG. 13, the force sensor 115 senses the forces between the lateral and medial portions of the distal femur and the tibial plateau. The visual display 117 shows the sensed forces (as an example, the display shows the forces unbalanced). An adjustment wrench 122 is coupled to a rotatable distraction screw 107 of the distal femoral alignment assembly 100. As shown in FIG. 14, when the unadjusted distal femoral alignment assembly 100 and the coupled force sensor 115 are first placed in the gap 120 between the distal femur 118 and the tibial plateau 121, the knee may be misaligned, i.e., the femoral axis and the tibial axis are not aligned with each other as in a normal knee. As shown in FIG. 14, the bottom surface of the distal femoral alignment assembly is 80.degree. relative to the mechanical axis 123 of the femur 118. As shown in FIG. 15, at least one of the rotatable screws 107, 108 is rotated with the adjustment wrench 122 to adjust the relative position of the adjustable medial and/or femoral portions and to correct the alignment of the knee. Generally, by balancing the sensed forces in the medial and lateral portions of the knee, correct alignment of the knee can be achieved (as shown in the visual display). For example, as shown in FIG. 16, the distal femoral alignment assembly 100 has been adjusted so that the bottom surface of the distal femoral alignment assembly is 85 degree relative to the mechanical axis 123 of the femur 118.

Figure 17:
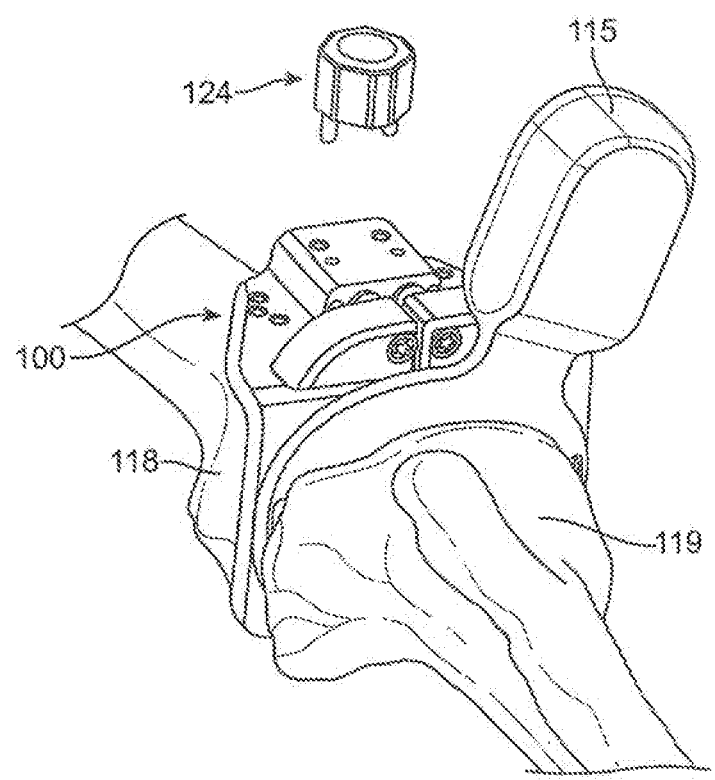
Figure 18:
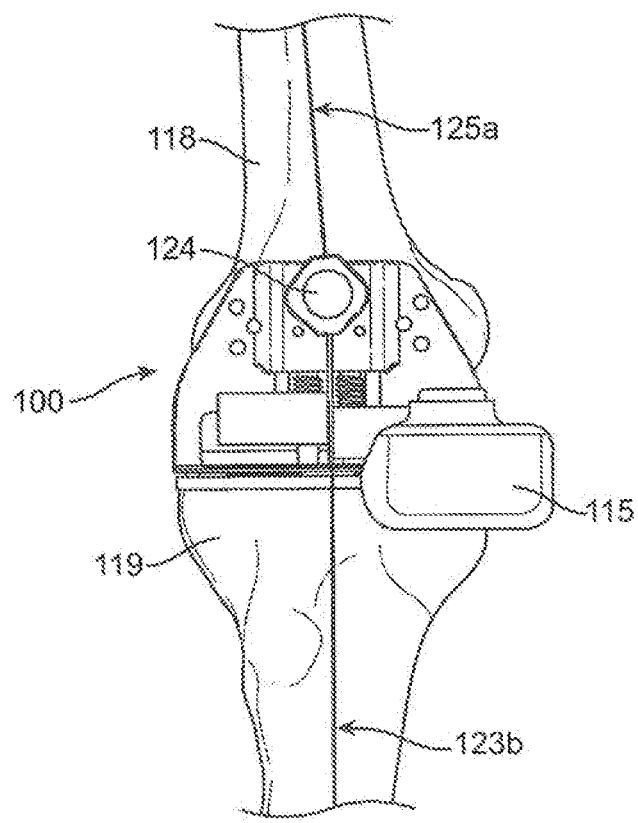
Figure 19:
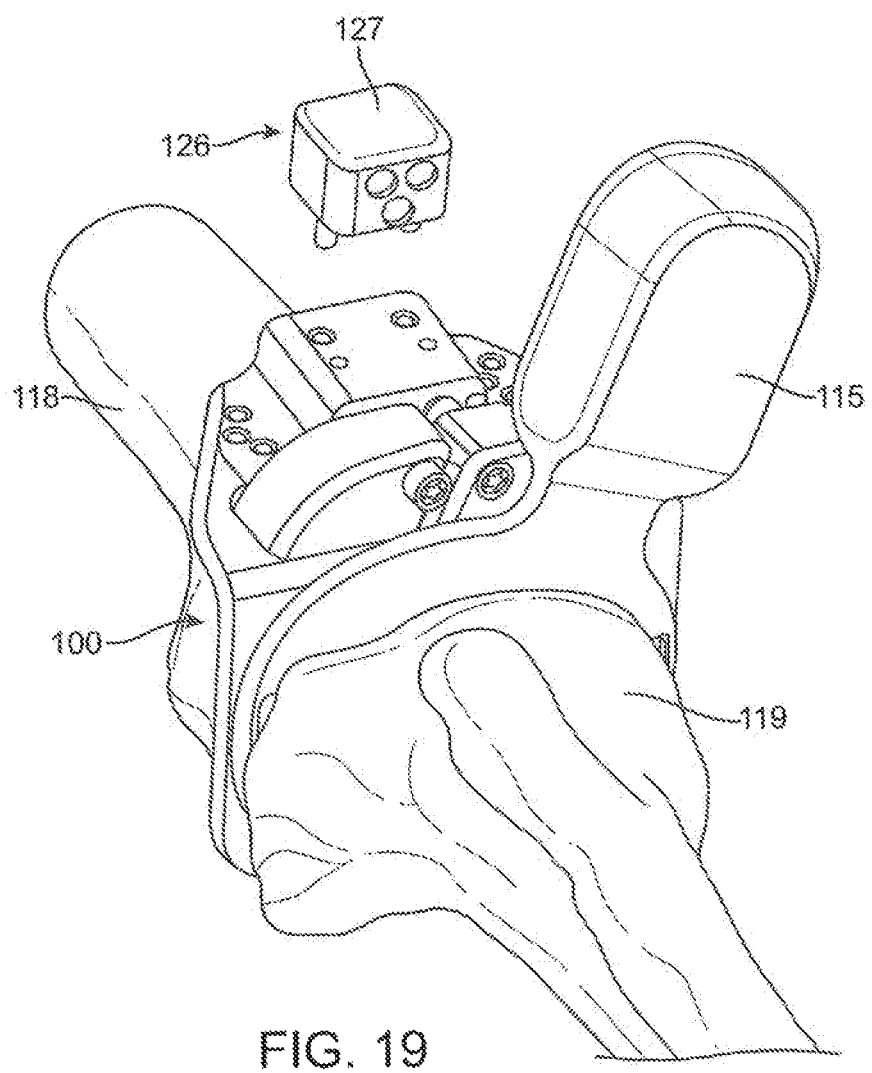
Figure 20:
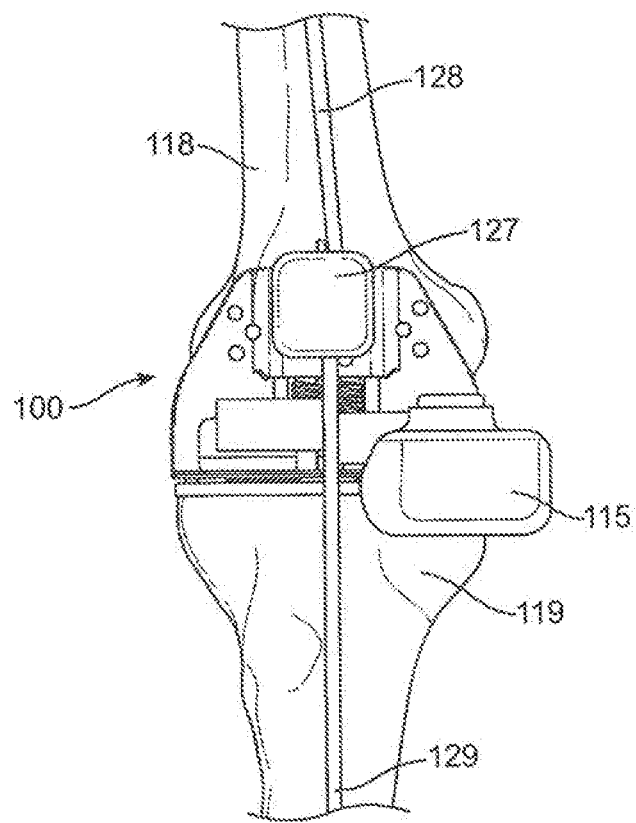

The system will typically further comprise a knee alignment verification means to verify the alignment of the knee by verifying the angle formed by the mechanical axes of the femur and tibia. As shown in FIGS. 17 and 18, the knee alignment verification means may be a laser knee alignment verification member 124 coupleable to the main body of the distal femoral alignment member 100. As shown in FIG. 18, the laser knee alignment verification member 124 emits a femoral laser beam. 125a to be aligned along the mechanical axis 123a of the femur and a tibial laser beam 125b to be aligned along the mechanical axis 123b of the tibia. The angle of the femoral laser beam and the tibial laser beam relative to each other can be used by the surgeon to verify the proper anatomical alignment of the knee, i.e., the angle between the mechanical axes 123a, 123b of the femur and tibia. Alternatively, as shown in FIGS. 19 and 20, the knee alignment verification means may be a mechanical knee alignment verification assembly 126. The mechanical knee alignment verification assembly 126 comprises a mechanical knee alignment verification hub 127, a femoral alignment rod 128 coupleable with the hub 127, and a tibial alignment rod 129 coupleable with the hub 127. The coupled femoral alignment rod 127 can be aligned along the mechanical axis 123a of the femur 118. The coupled tibial alignment rod 129 can be aligned along the mechanical axis 123b of the tibia 119. The angle of the femoral alignment rod 148 and the tibial alignment rod 129 relative to each other can be used by the surgeon to verify proper alignment of the knee.

Figure 21:
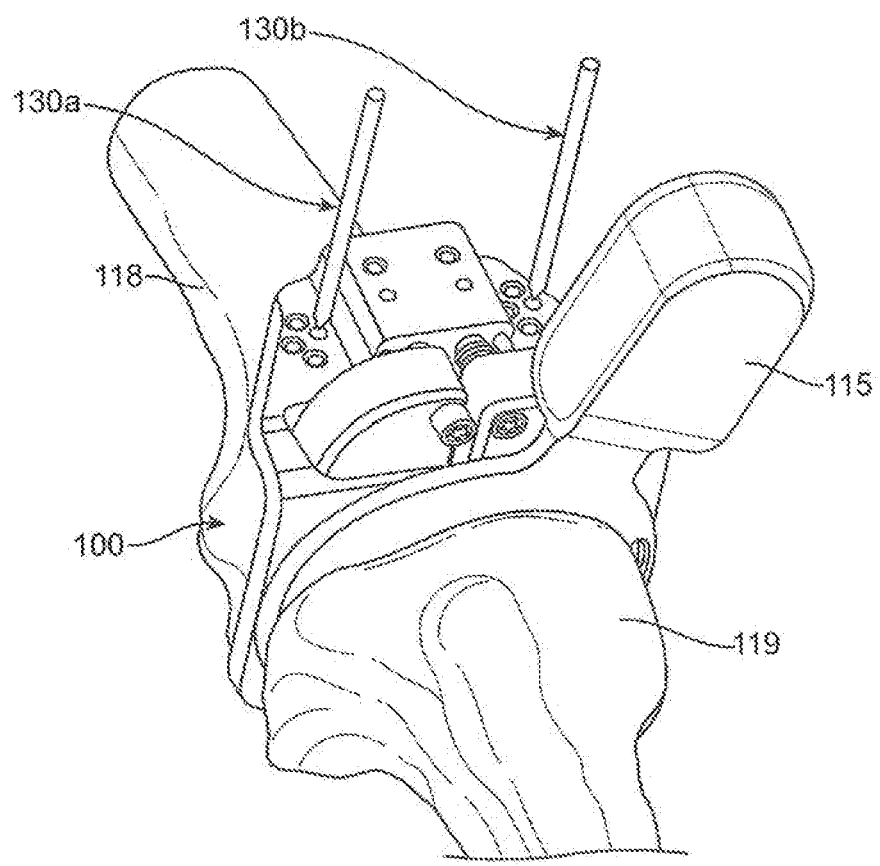
Figure 22:
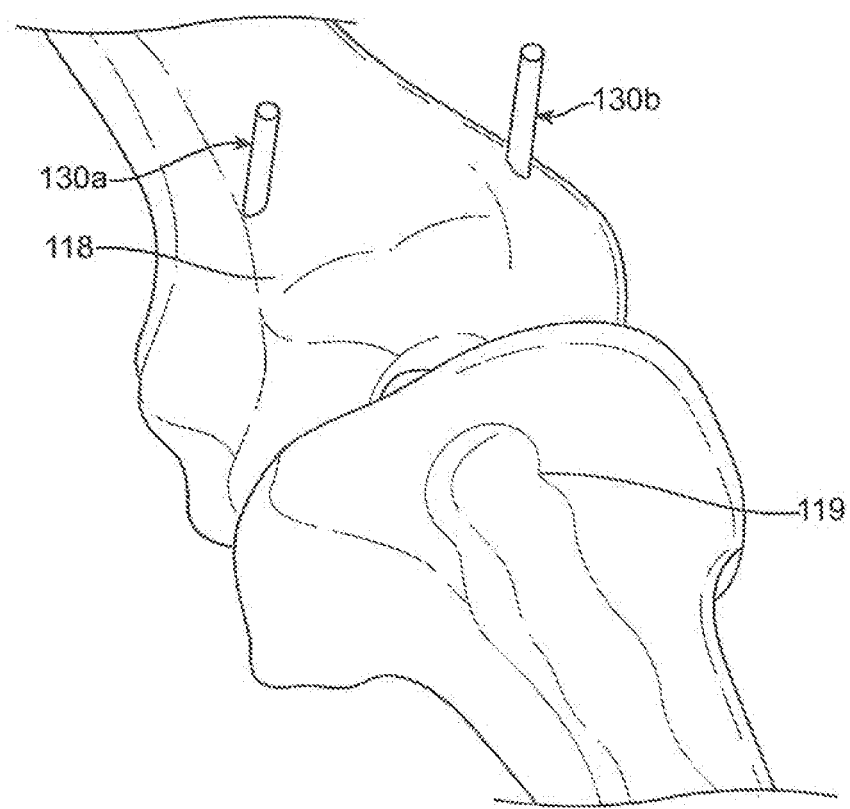

As shown in FIG. 21, the system may further comprise a plurality of locating pins 130a, 130b. When the knee is properly aligned, at least one locating pin (130a and/or 130b) may be placed on the medial side of the distal femur 118 and at least one locating pin may be placed on the lateral side of the distal femur as guided by the apertures of the distal femoral alignment assembly. As shown in FIG. 22, once the locating pins 130a, 130b are placed on the distal femur 118, the distal femoral alignment assembly 100 may be disengaged from the distal femur.

Figure 23:
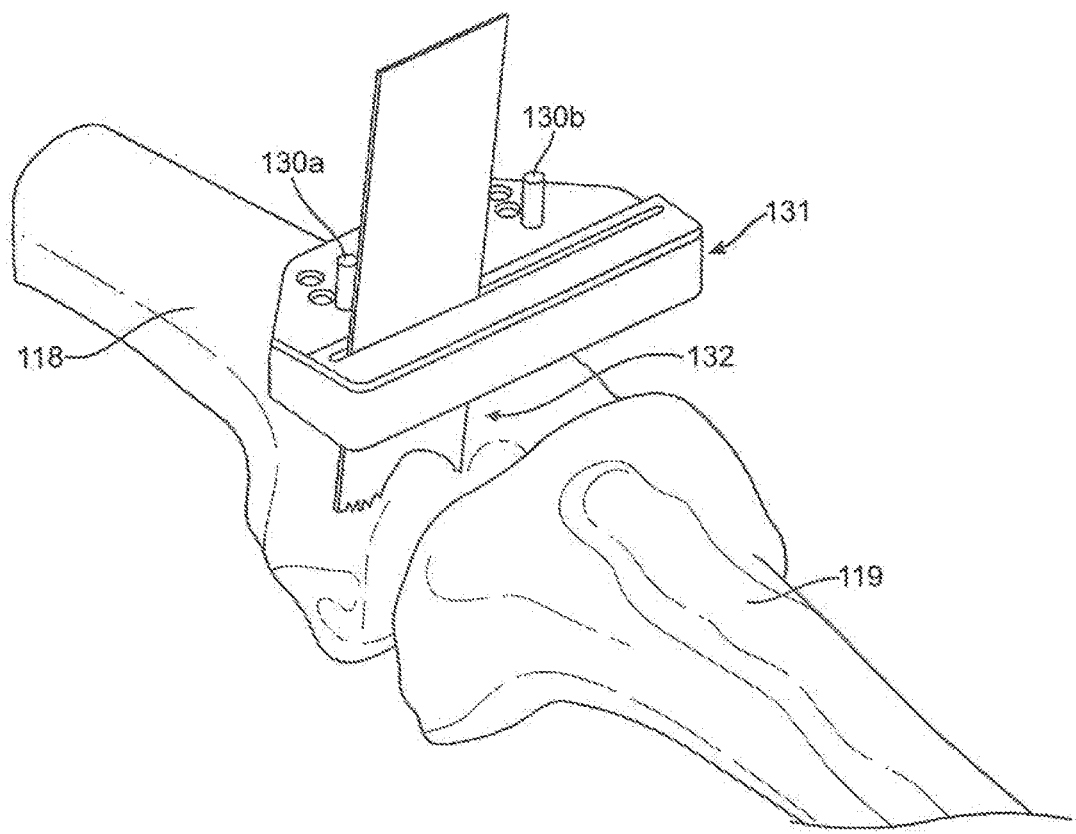

As shown in FIG. 23, the system may further comprise a distal femoral cutting guide 131 which can be coupled to the distal femur 118 and positioned based on the position of the locating pins 130a, 130b. Cuts are made on the distal femur 118, for example, with a surgical saw blades 132. Typically, these cuts will form the basis for positioning of the femoral portion of an artificial knee. Exemplary surgical saw blades which may be used to make these cuts on the distal femur are described co-assigned U.S. Pat. Nos. 6,022,353; 6,503,253; and 6,723,101, the entire contents of which are incorporated herein by reference.

Figure 24A:
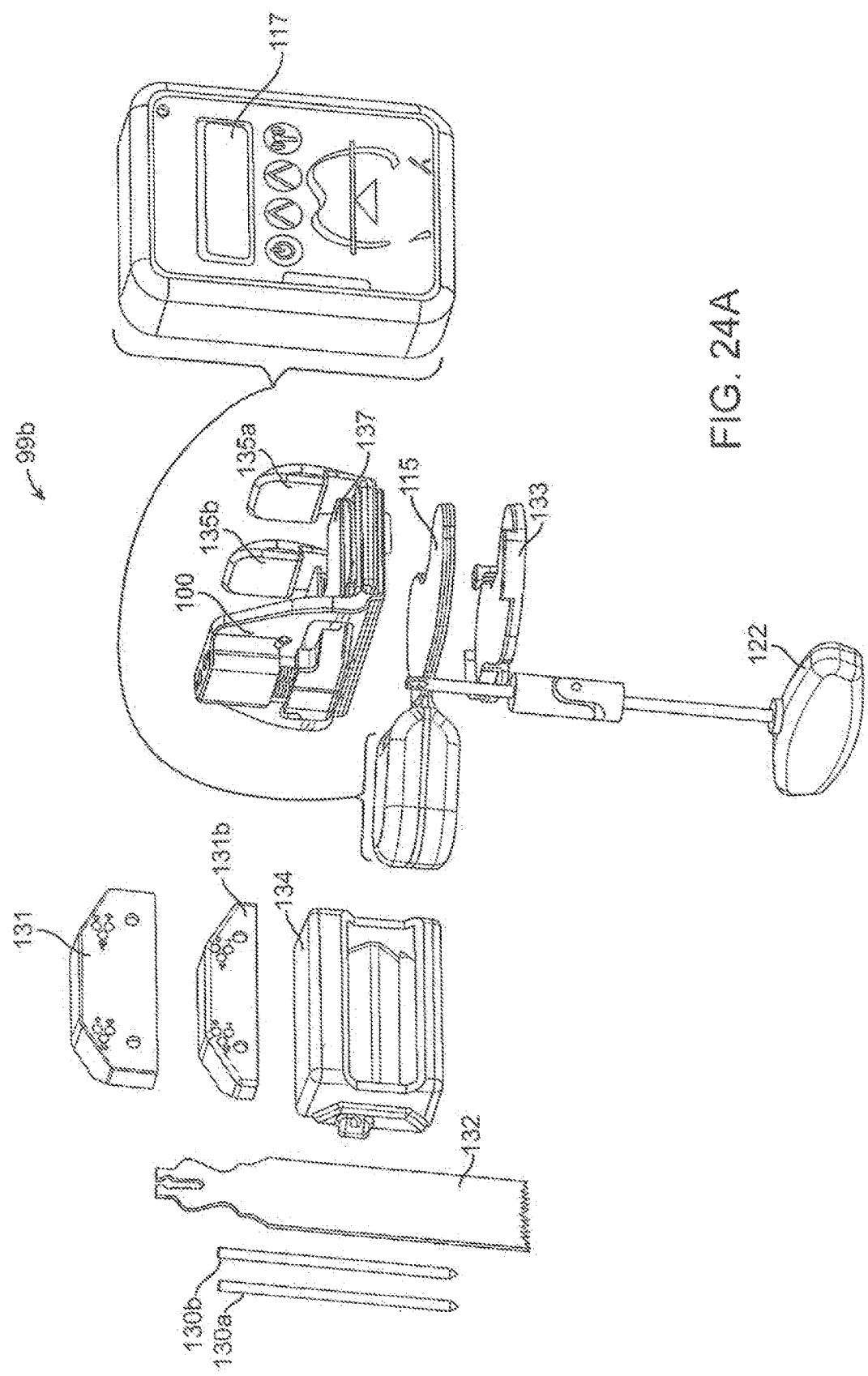
Figure 25:
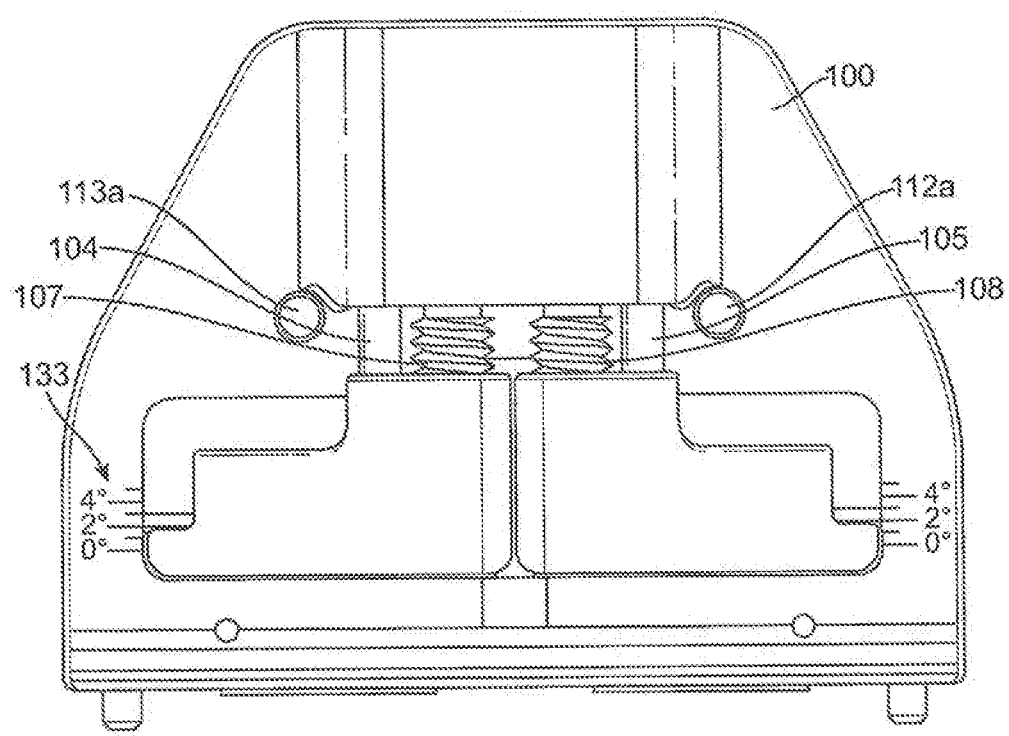
FIG. 25 shows a top view of the unadjusted distal femoral alignment assembly.
Figure 26:
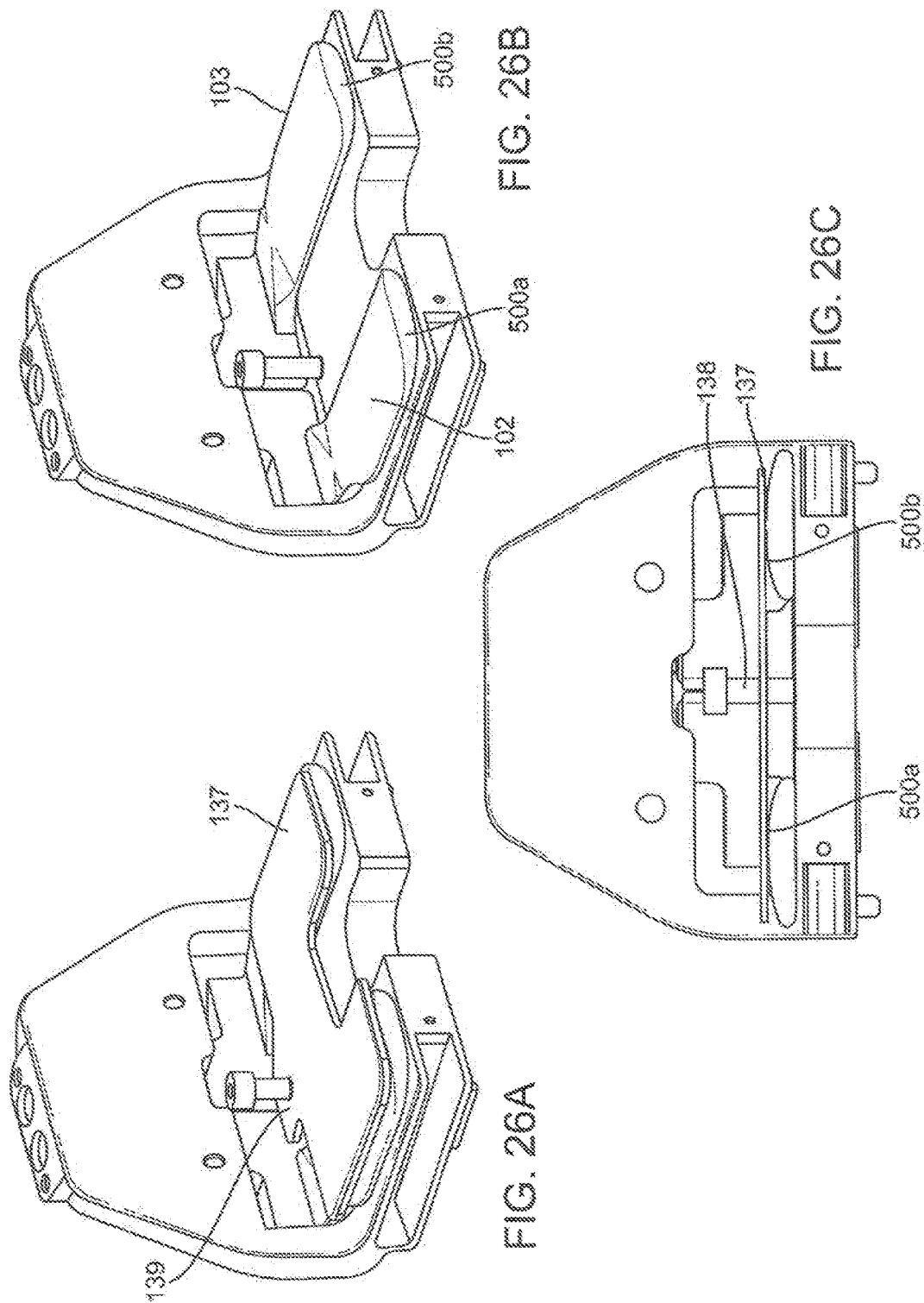
FIGS. 26A and 26C show perspective posterior views of the unadjusted distal femoral alignment assembly shown in FIG. 25.
FIG. 26B shows a posterior perspective of the unadjusted distal femoral alignment assemblies shown in FIGS. 26A and 26C with the bone interface plate removed.

Referring now to FIGS. 24A-B, an alternative distal femoral alignment system 99b is shown including cutting guide 131 for making a provisional cut on the distal femur in order to mount the distal femoral alignment assembly 100 flush against the provisionally cut distal femur. As shown in FIG. 25, angular graduation marks 133 are provided. The graduation marks correspond to movement created by adjusting either the medial or lateral distraction paddles 102, 103 as shown in FIG. 26B. For clarity purposes, a right distal femur is shown in FIGS. 27-28 and 34-35 and a right knee joint with femur and tibia is shown in FIGS. 29-33. The medial side of components or assemblies of the distal femoral alignment system shown in FIG. 24 are hereby described either medial or lateral based on their position when used on a right knee. Of course, the invention can be used on the left and/or right knees. Convex shaped pivot fulcrums 500a, 500b are provided on the surfaces of the distraction paddles 102, 103 which directly contact the provisionally cut distal femur when the distal femoral alignment assembly 100 is mounted against the distal femur 118. The curved surface of the distraction paddles 102, 103 creates fixed distance fulcrum points to determine how much angle is being adjusted. FIGS. 26A and 26C show another embodiment of the distal femoral alignment assembly 100 of the alternative distal femoral alignment system 99b shown in FIG. 24, which includes bone interface plate 137. This plate 137 provides protection from convex shaped distraction paddles 102 and 103 from indenting the softer cancellous bone exposed as a result of a provisional cut being made on the distal femur 118 (not shown in FIG. 26). FIG. 26C shows the bone interface plate 137 sitting on top of convex shaped distraction paddles 102 and 103 in their unadjusted position. Shoulder screw 138 is shown, which slips through a loosely fitted hole 139 in bone interface plate 137 to allow for tilting of bone interface plate 137 when convex shaped distraction paddles 102 and 103 are adjusted from their unadjusted position to an adjusted position. Spacing between convex shaped adjustment paddles 102 and 103 is maintained in the medial-lateral direction to provide for a known pivot fulcrum between the two convex shaped adjustment paddles, which corresponds to angular graduations 133 shown in FIG. 25. The angular gradations provide an indication of the angle between the femur and tibia.

Figure 27:
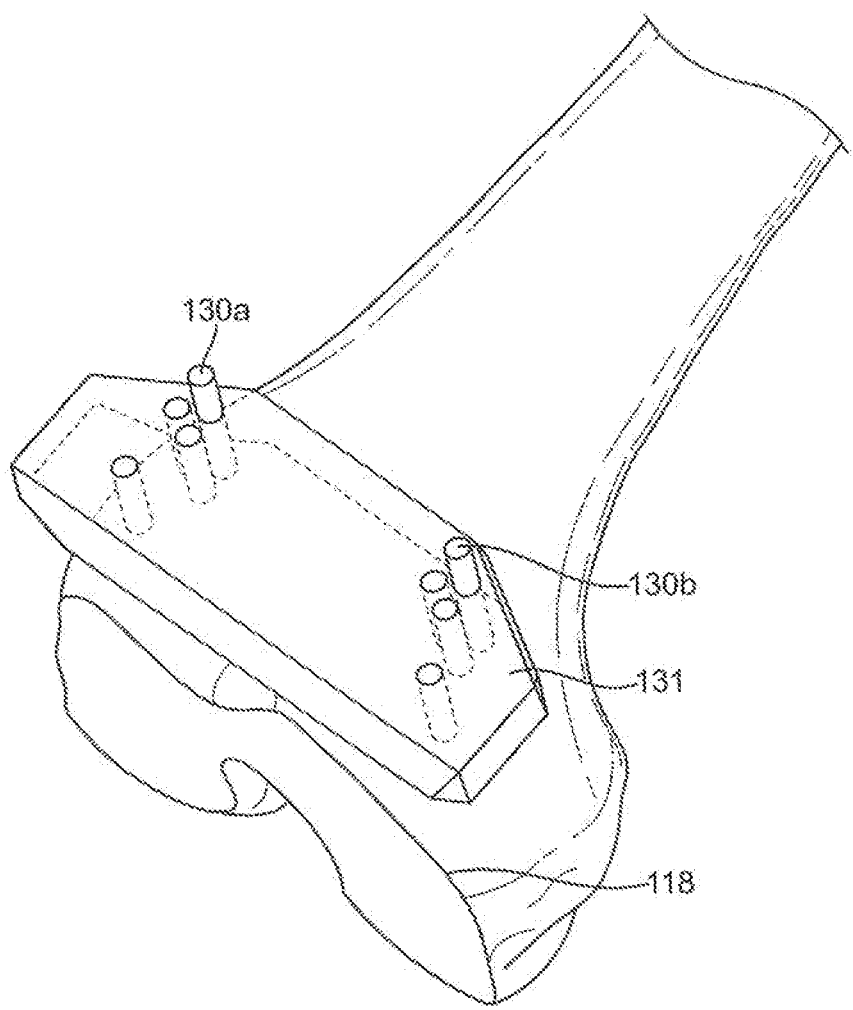
Figure 28:
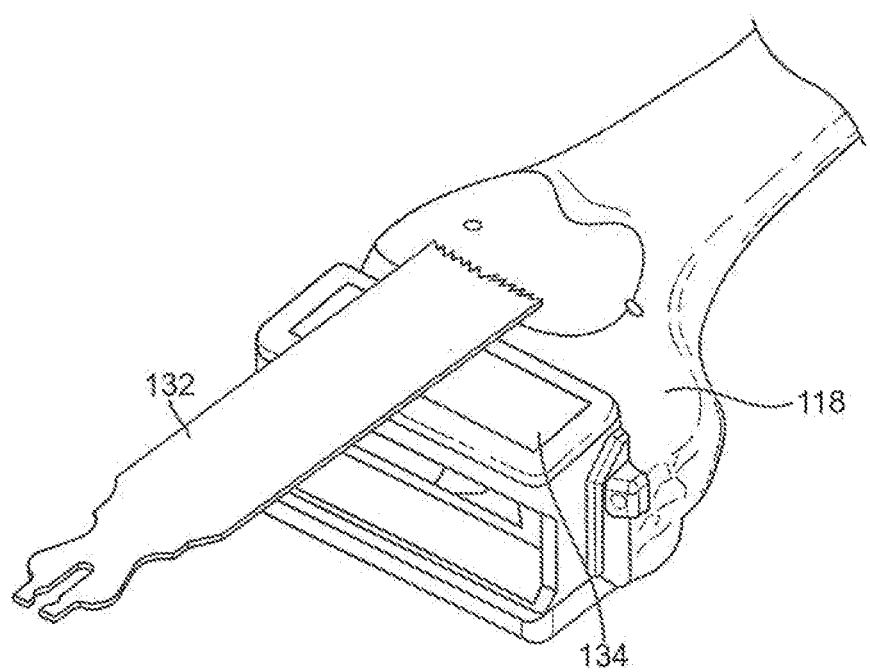
Figure 29:
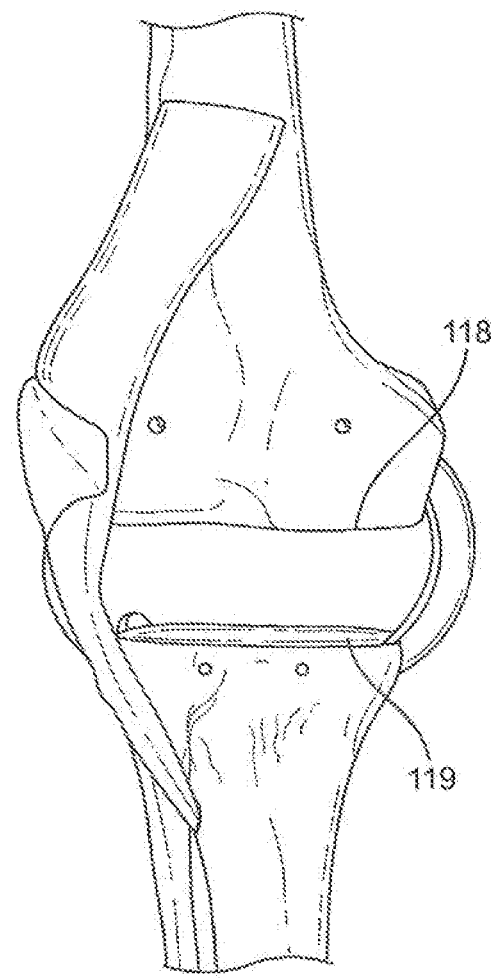

Referring now to FIGS. 27-35, a method of using an exemplary knee alignment system used during knee replacement surgery is shown according to embodiments of the invention. For purposes of clarity, a bone cut has already been made on the proximal tibia 119 prior to the methods described in FIGS. 27-35. FIG. 27 shows provisional distal femoral cutting guide 131 moveably attached to the provisionally cut distal femur 118 via two pins 130a and 130b. FIG. 28 shows provisional femoral cutting guide 131 and pins 130a and 130b now having been removed and femoral anterior-posterior cutting guide 134 is now removably attached to distal femur 118. Saw blade 132 is shown and the anterior and posterior bone cuts are performed on distal femur 118. FIG. 29 shows now the "extension gap" with the proximal tibial cut having been made and a provisional distal femoral cut having been made. The posterior femoral cut has also been made but hidden from view in FIG. 29. The anterior cut has also been made on distal femur 118.

Figure 30:
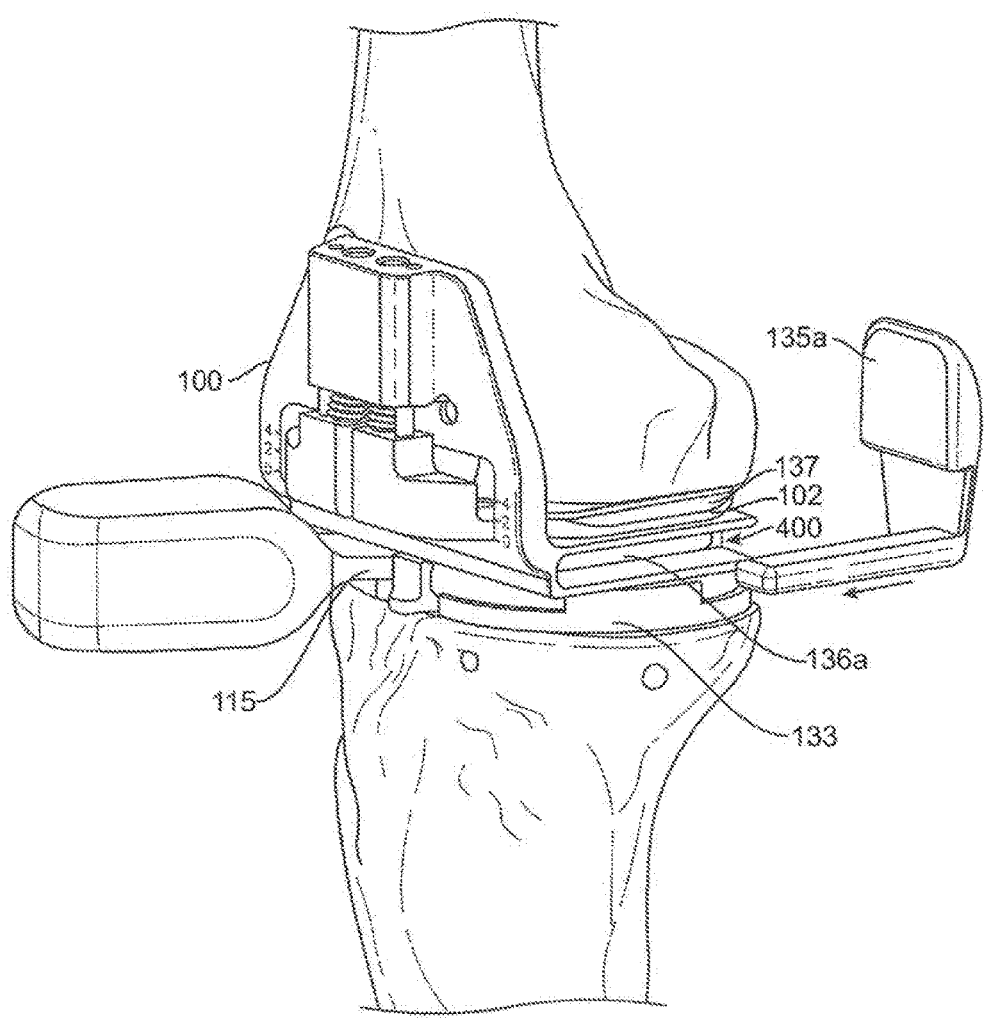
Figure 31:
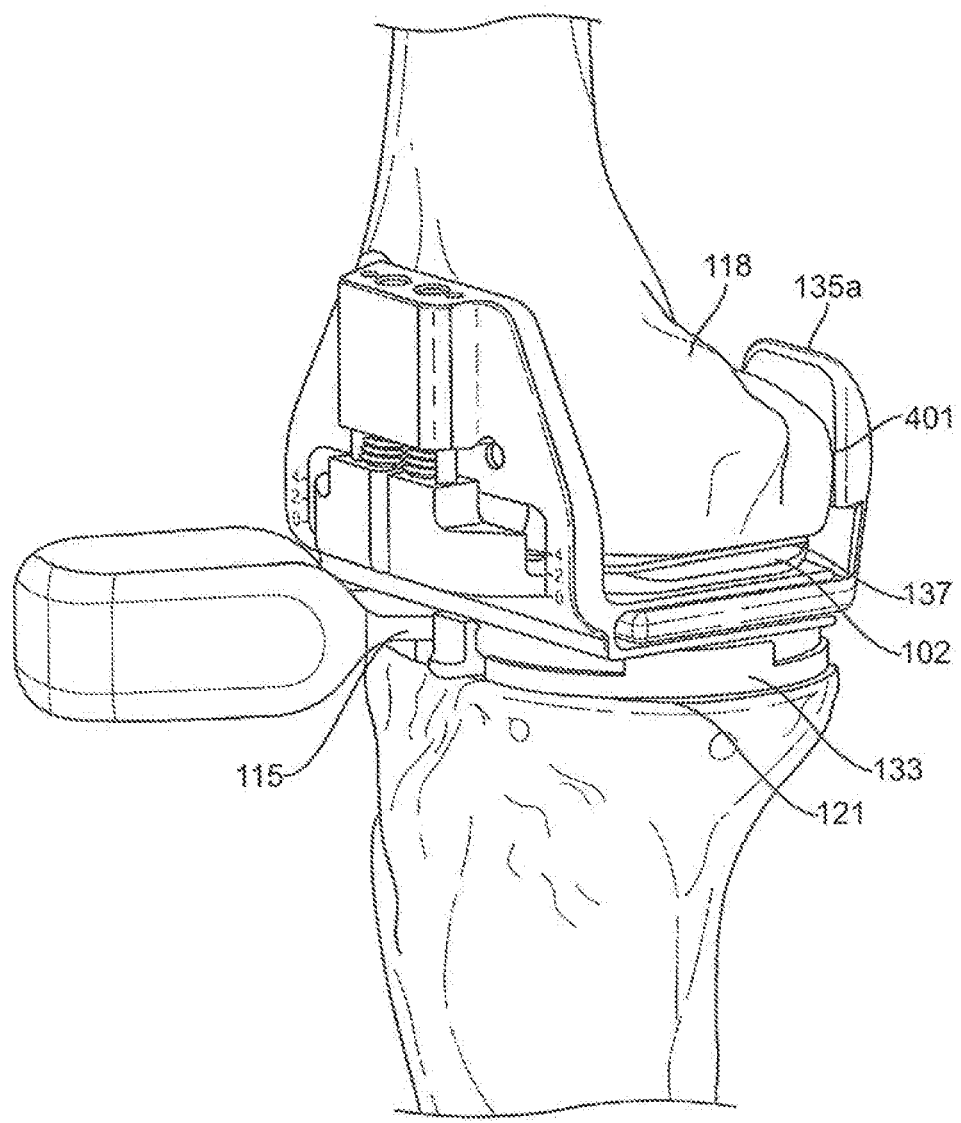
Figure 32:
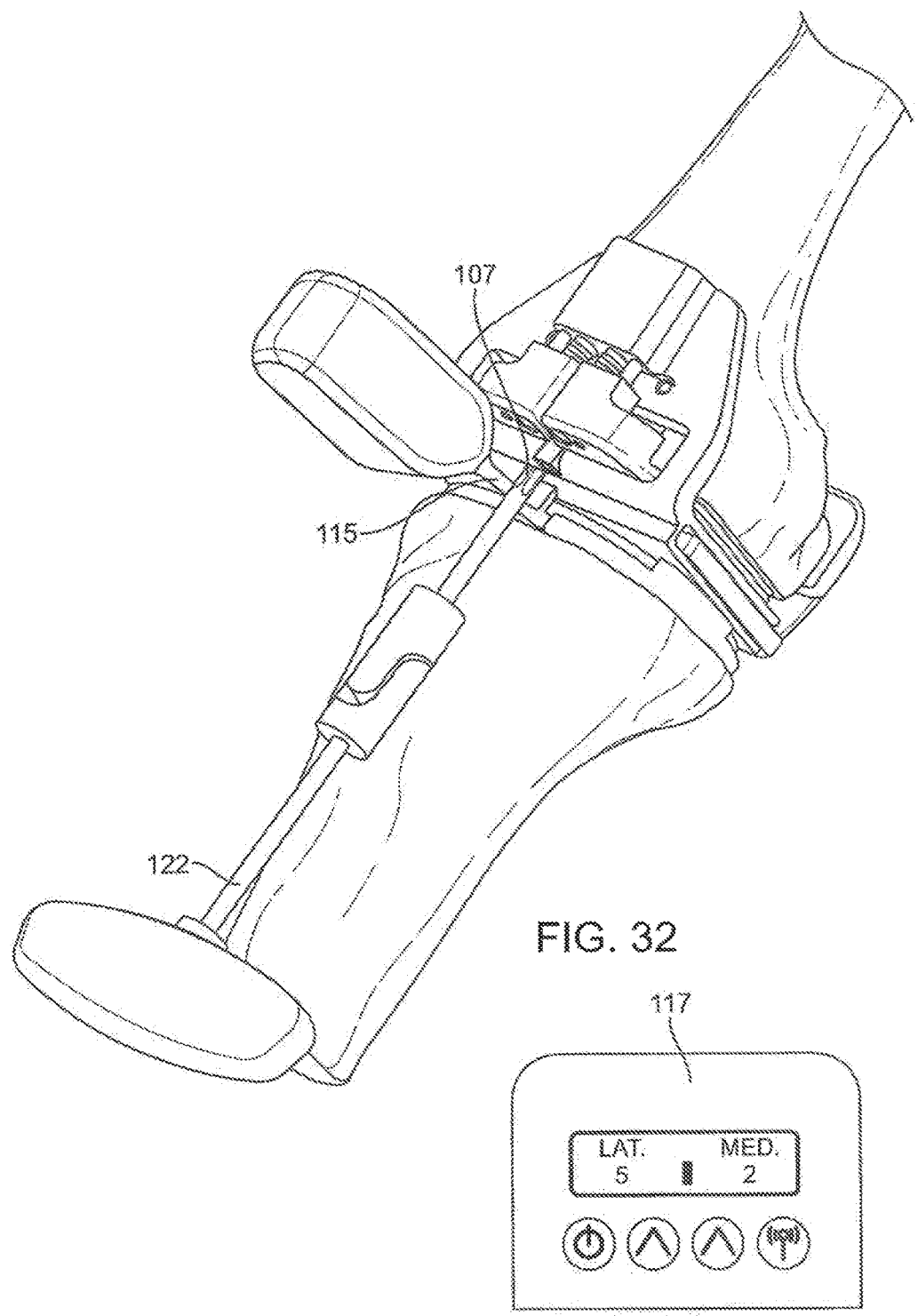
Figure 33:
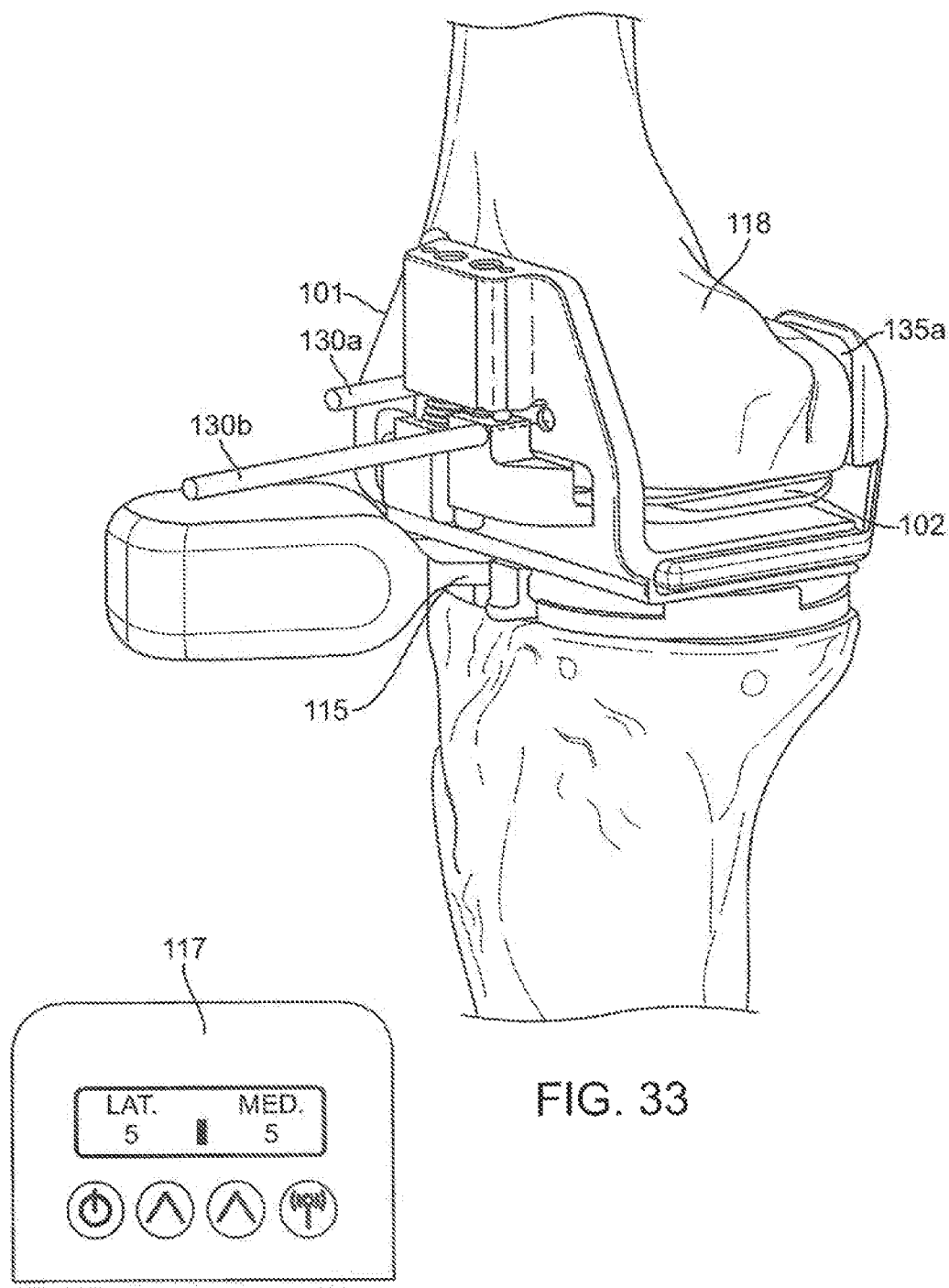
Figure 35:
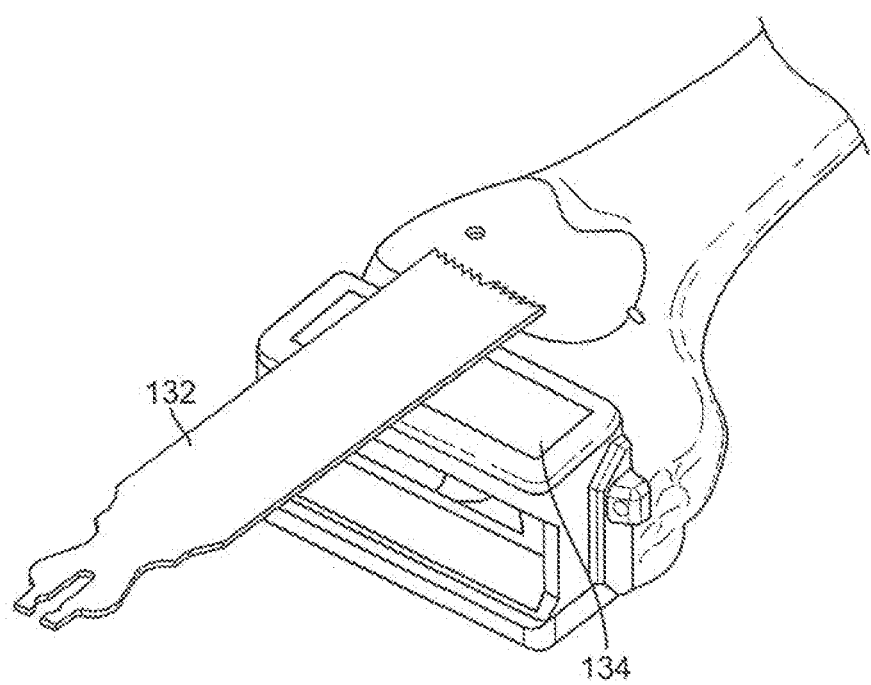
Figure 36:
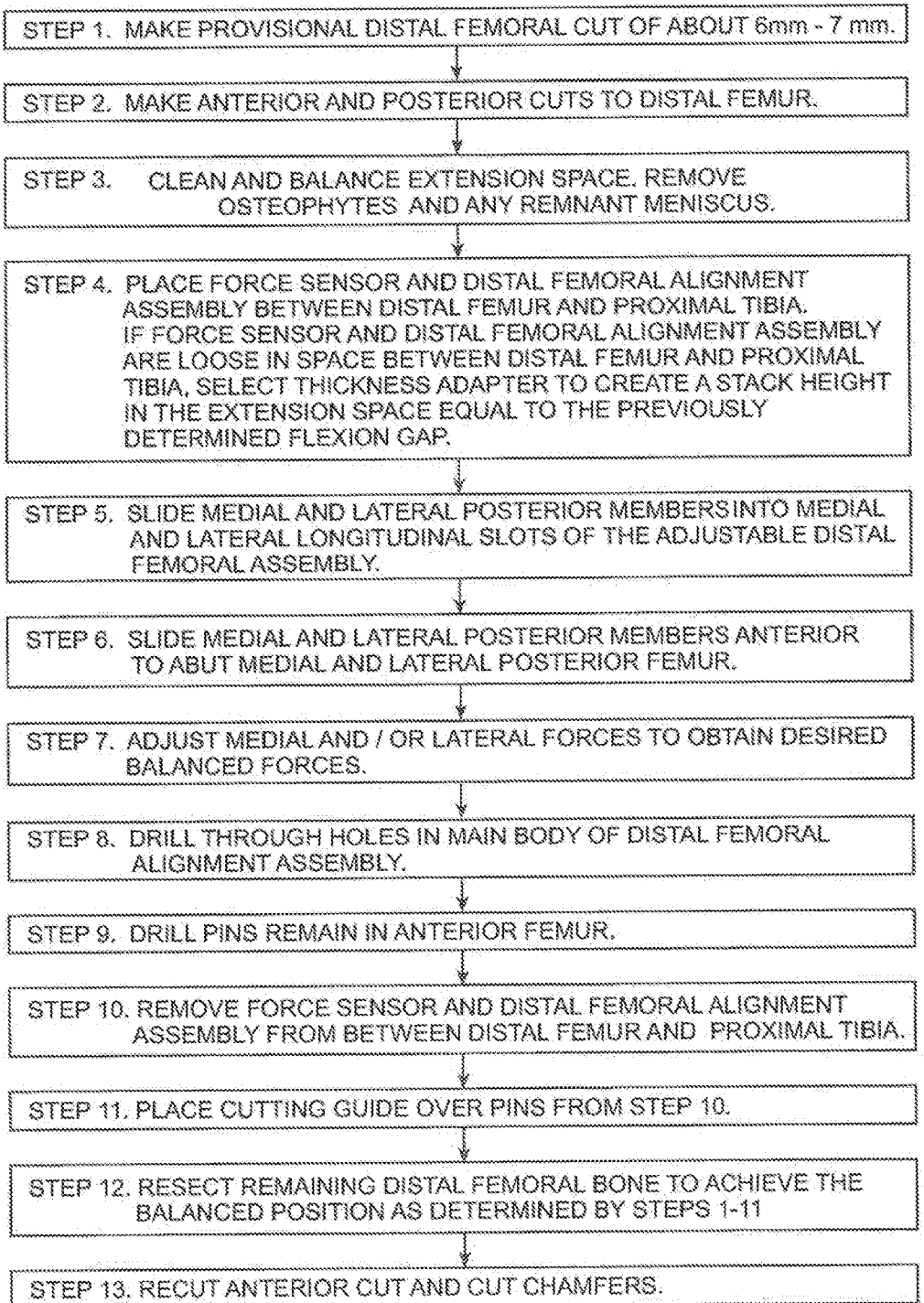
FIG. 36 is a flow chart schematically illustrating a method for aligning and balancing a knee during knee surgery according to embodiments of the invention.

Moving now to FIG. 30, the distal femoral alignment assembly 100 and other components of the distal femoral alignment system 99b are shown between the proximal tibia 119 and the distal femur 118, with the leg in full extension. Thickness adapter 133 is shown moveably coupled to force sensor 115, and force sensor 115 is moveable coupled to distal femoral assembly 100. Adjustable posterior member 135a is shown adjacent to a longitudinal slot 400 open on the posterior side of distal femoral assembly 100, with the slot closed on the anterior side of the distal femoral assembly 100. FIG. 31 shows adjustable posterior member 135a having now been moveably coupled within the longitudinal slot 400 along the medial side of distal femoral assembly 100. Moveable coupling means 136a, 136b can include magnets or other common coupling means such as screws or spring clips. Longitudinal slots are also provided on the opposite side of the distal femoral assembly 100. Longitudinal slots along the sides of distal femoral assembly 100 are of adequate length to allow for anterior-posterior adjustment of adjustable posterior member to abut the previously made posterior cut 401 of the distal femur 118. The adjustable posterior members further balance extension filling the posterior space with a condylar thickness similar to the posterior condylar thickness of the femoral component to be implanted thus taking into account soft-tissue tendencies, or bias. FIG. 32 shows components and assemblies of the distal femoral alignment system 99b now completely in place between the proximal tibia and the distal femur and force readings coupled from force sensor 115 are being displayed on display 117, It is understood that display 117 may be integral to force sensor 115. The display 117 can also be separable from the sensor. The display 117 is showing force readings of 5 and 2 lateral and medial respectively, indicating lower force between the medial side of the distal femur and the medial side of the proximal tibia, in this example. Adjustment wrench 122 is shown in line with the medial distraction screw 107. FIG. 33 shows the medial distraction paddle 102 having now been adjusted to a point wherein the forces being measured by sensor 115 and displayed by display 117 read 5 on both the lateral and the medial side. Pin 130a is shown being driven through a lateral side cutting guide locating aperture and pin 130b has yet to be driven through the medial side cutting guide locating aperture. FIG. 34A shows both pins having now been driven through cutting guide locating apertures of distal femoral assembly 100, and distal femoral assembly 100 now having been removed from the distal femur 118. Cutting guide 131b is positioned over pins 130a and 130b. FIG. 34B shows cutting guide 131b now positioned over pins 130a and 130b and saw blade 132 will be used to make the final distal femoral cut at an angle "A" which is the plane of balanced resection as determined by the force sensor. FIG. 35 shows femoral anterior-posterior cutting guide 134 now removably coupled to distal femur 118 and saw blade 132 is shown making a final cut on the anterior distal femur. Anterior and posterior chamfer cuts will also be made on the distal femur 118 at this point.

Figure 37:
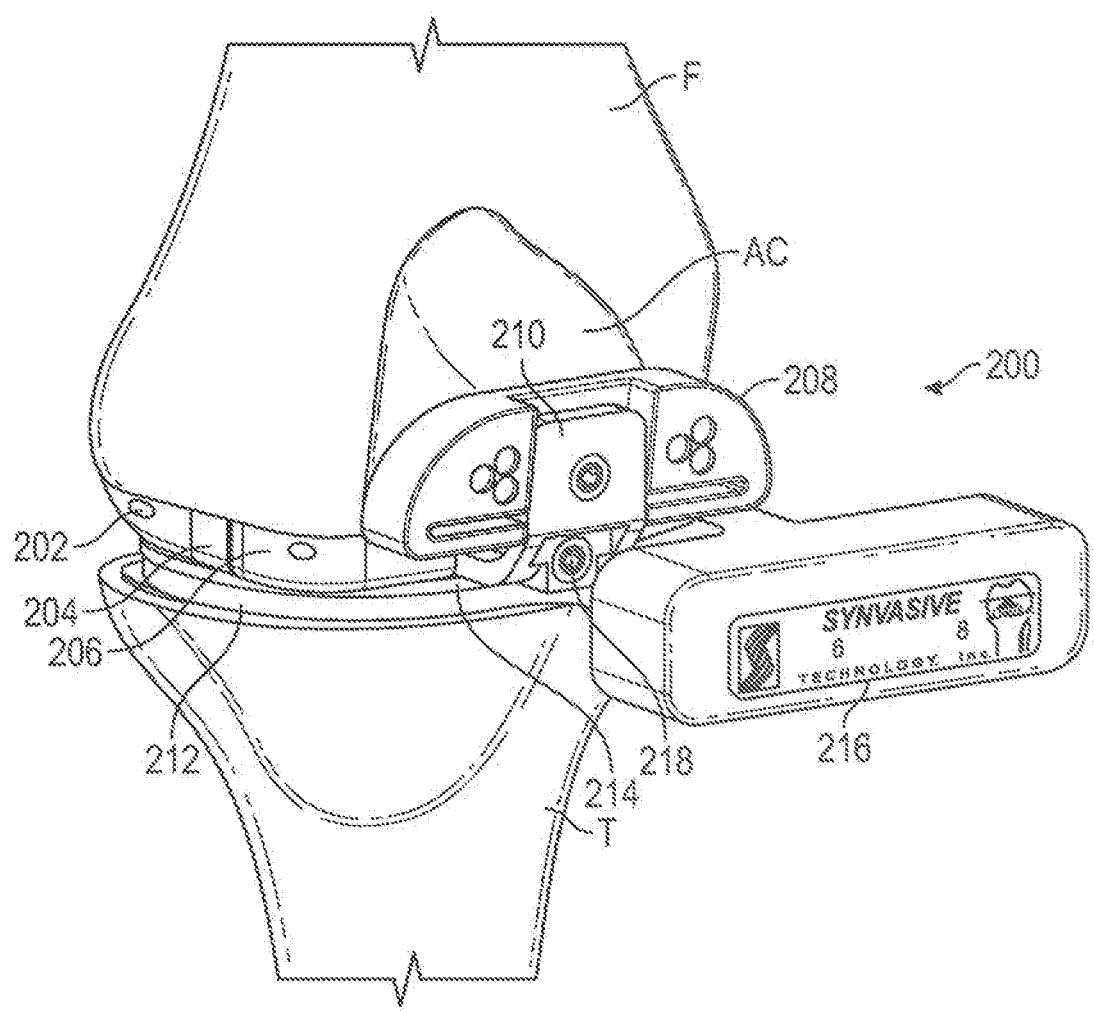
FIG. 37 is a perspective view of a system for positioning a bone cutting device on a femur, according to one embodiment of the present invention.

Referring now to FIG. 37, in another embodiment of the invention, a system 200 for positioning a bone cutting guide on a femur during knee surgery is shown. System 200 may generally include an adjustable femoral attachment member 202, a cutting guide 208, and a force sensor 212 coupled with a display 216. Femoral attachment member 202, which is described in further detail below, may include a stationary portion 204, which attaches in a fixed way to the femur F, and an adjustable portion 206, which moves relative to stationary portion 204 to create a space between the two portions on the lateral, medial or both sides of the knee joint. Attachment member 202 may include a single adjustment member 218 for adjusting adjustable portion 204 and medial and lateral elevators (also not visible in FIG. 37) for creating a medial space and/or a lateral space in the joint. System 200 may also include a slide member 210 for attaching to cutting guide 208 to facilitate its attachment to adjustable femoral attachment member 202. Finally, system 200 may further include an insert 214 (or multiple inserts) to be positioned between femoral attachment member 202 and sensor 212. Inserts 214 of various thicknesses may be provided, so that a physician can select a desired amount of initial tension within the knee. In various embodiments, inserts 214 may be removably attachable to sensor 212.

In FIG. 37, system 200 is shown in position within a knee joint, between a cut distal end of a femur F and a cut proximal end of a tibia T, where an anterior cut AC has also been made to the femur F. (A posterior cut is also typically made prior to inserting system 200 in the knee, but the posterior aspect of the femur F is not visible in FIG. 37.) In this embodiment, system 200 will be described for use in a knee where initial distal, anterior and posterior bone cuts have been made on the femur F and where at least an initial bone cut has been made on the proximal end of the tibia T. In alternative embodiments, however, it may be possible to use system 200 in a knee surgery procedure in which fewer (or no) initial bone cuts have been made.

In brief summary, system 200 may be used in a knee surgery procedure to facilitate and/or improve upon positioning of bone cutting guide 208 on the femur F in order to make a bone cut on a distal end of the femur F. As will be described in greater detail below, system 200 may be placed within the knee joint, and femoral attachment member 202 may be adjusted to create a space, and thus increase tension, on either the medial side of the knee or the lateral side of the knee, to balance forces within the joint. Forces may be sensed by sensor 212 and displayed on display 216. As femoral attachment member 202 is adjusted, cutting guide 208 moves along with attachment member 202 and changes its angle of orientation relative to the distal femur F. When sensed forces within the knee are balanced, cutting guide 208 may be fixed to the femur F, and the femoral bone cut may be made.

One improvement of system 200 is that it can remain in place within the knee joint while the knee moves through a range of motion between flexion and extension. Another improvement is that both the medial side and the lateral side of femoral attachment member 202 may be adjusted using the same adjustment member 218. Furthermore, system 200 is low profile, so is easier to insert into the joint space than at least some prior art systems. Also, system 200 may be used on a femur F after initial bone cuts have been made, unlike some systems designed for use with an uncut femur.

Referring now to FIGS. 38A-38H, a number of different views of adjustable femoral attachment member 202 are shown. As previously mentioned, femoral attachment member 202 generally includes stationary portion 204, which attaches in a fixed manner to the cut distal end of a femur, and adjustable portion 206, which moves relative to stationary portion 204 to increase the space between the distal femur and proximal tibia on the medial or lateral side of the knee. Stationary portion 204 includes a platform 220, for contacting the cut distal end of the femur, and screw holes 236, through which screws are advanced to attach stationary portion 204 to the femur. Stationary portion 204 is removed from FIGS. 38C, 38D, 38F and 38G so that other parts of femoral attachment member 202 may be more easily visualized.

Figure 38A:
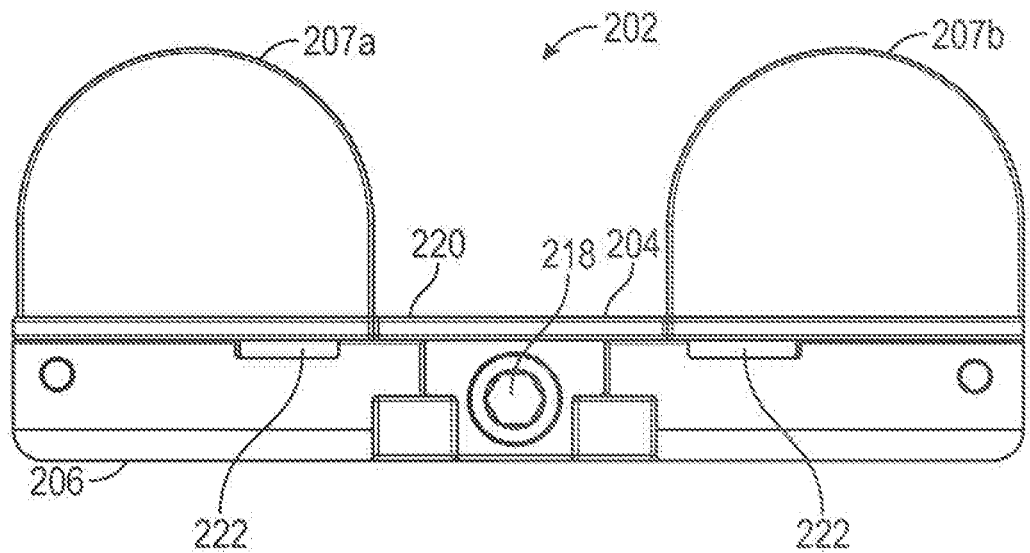
FIGS. 38A-38H are various views of an adjustable femoral attachment portion of the system of FIG. 37.
Figure 38B:
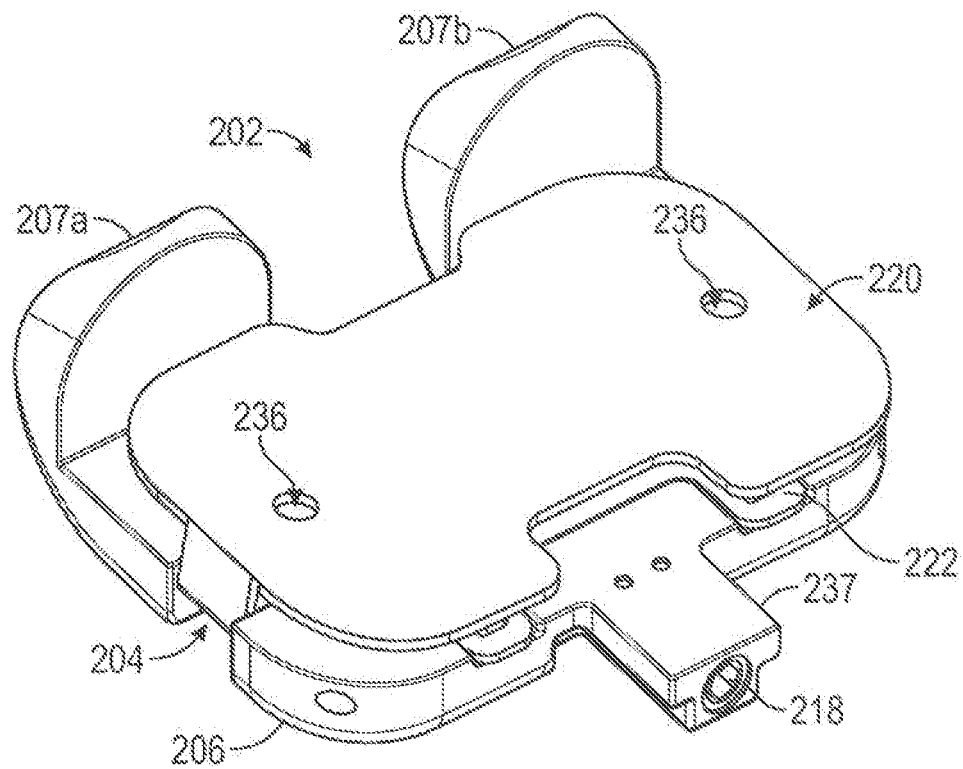
Figure 38C:
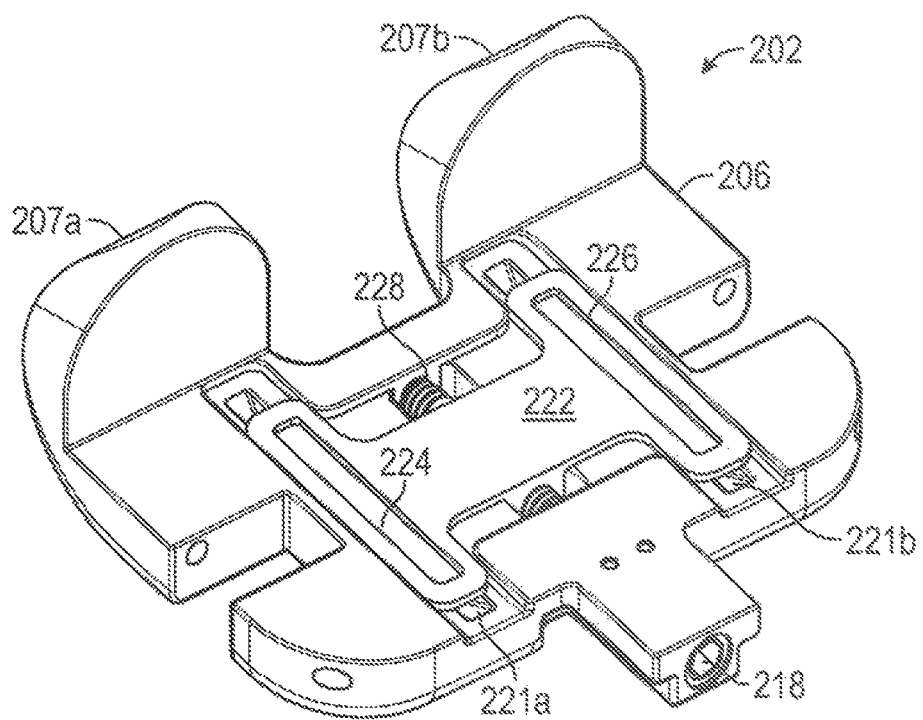
Figure 38D:
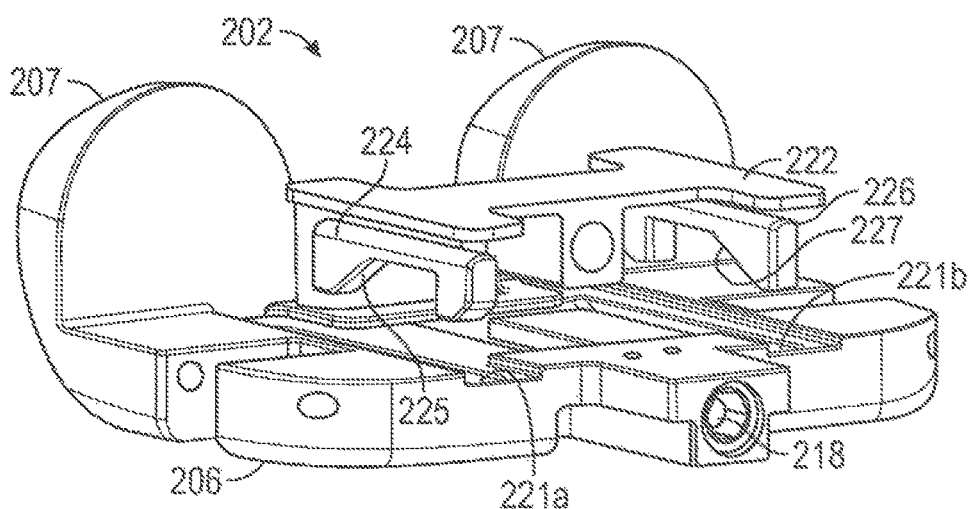

FIGS. 38A-38D provide various views of adjustable femoral attachment member 202 in an unadjusted configuration. Adjustable portion 206 of adjustable femoral attachment member 202 may include left and right (or "lateral" and "medial") condylar members 207a, 207b, an elevator adjuster 222, a cutting guide attachment post 237 along which cutting guide 208 slides to contact a femur, and adjustment member 218. Stationary portion 202 may include platform 220, as already mentioned. In FIGS. 38C and 38D, platform 220 is removed to better show elevator adjuster 222, a lateral (or "left") elevator 224 and a medial (or "right") elevator 226 of adjustable portion 206.

As shown in FIGS. 38C and 38D, each elevator 224, 226 has a sloped bottom surface 225, 227 on one end of its bottom side, and each elevator 224, 226 fits into a slot 221a, 221b on adjustable portion 206. As is visible in FIG. 38C, each slot 221a, 221b includes a sloped surface at one end, over which the sloped surface 225, 227 of its corresponding elevator 224, 226 rides. Elevator adjustor 222 sits over elevators 224, 226 and is moved back and forth along slots 221a, 221b by adjusting adjustment member 218. When moved in one direction, elevator adjustor 222 pushes one of elevators 224 up a slope of its corresponding slot 221a. When moved in the opposite direction elevator adjustor 222 pushes the other elevator 226 up a slope of its corresponding slot 221b. Elevators 224, 226, when elevated, push against platform 220, causing it to rise on one side or the other, thus creating space between adjustable portion 206 and stationary portion 204, and thus increasing tension (and thus sensed force) on that side of the joint. By this mechanism, system 200 is able to make medial and/or lateral tension adjustments using only one adjustment member 218.

Figure 38E:
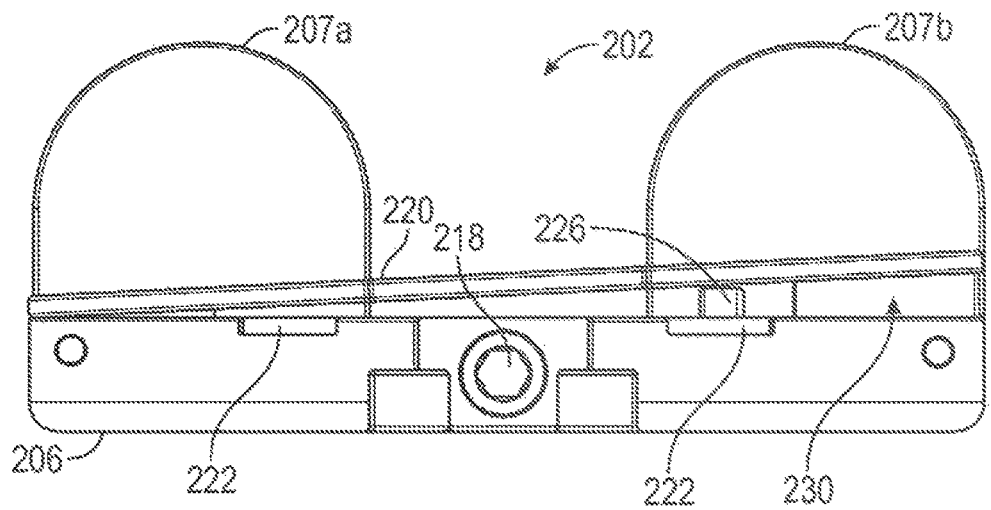
Figure 38F:
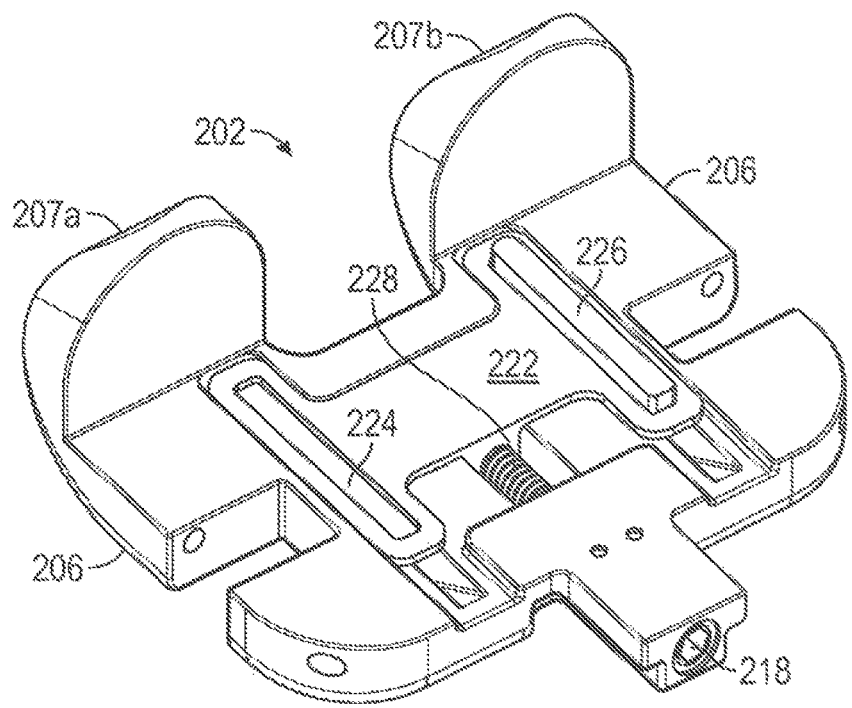

Referring now to FIGS. 38E and 38F, femoral attachment member 202 is shown after elevator 226 has been elevated to raise platform 220 and thus create a space 230. Space 230 will thus increase a distance between a femur and a tibia on one side of the knee (either the lateral or medial side, depending on what knee system 200 is being used on). FIG. 38F shows attachment member 202 with platform 220 removed, so that the raised elevator 226 is visible. Elevator 226 may be raised, for example, by turning adjustment member 218 in a first direction (clockwise or counter-clockwise in alternative embodiments).

Figure 38G:
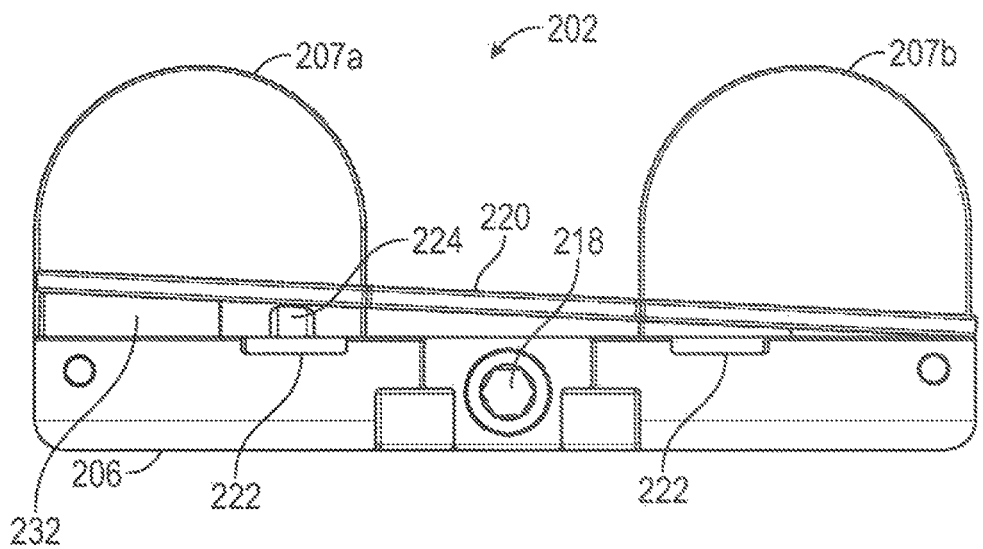
Figure 38H:
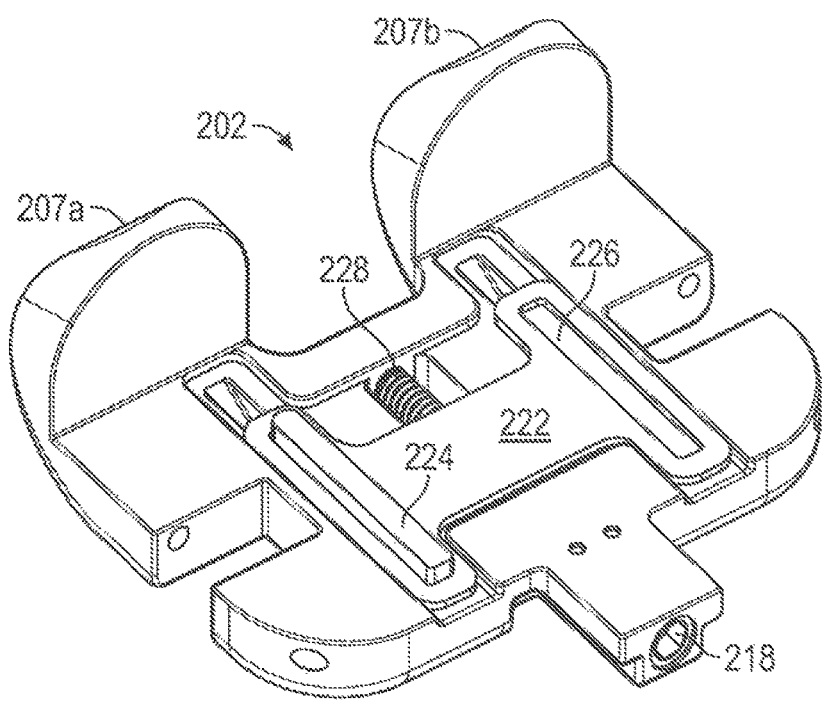

FIGS. 38G and 38H show femoral attachment member 202 after elevator 224 has been elevated to raise platform 220 and thus create a space 232 on the opposite side of attachment member 202. Space 232 will increase a distance between the femur and the tibia on the opposite side of the knee as that previously discusses (either the lateral or medial side, depending on what knee system 200 is being used on). FIG. 38H shows attachment member 202 with platform 220 removed, so that the raised elevator 224 is visible. Elevator 224 may be raised by turning adjustment member 218 in the opposite direction of that used to raise elevator 226.

Figure 39A:
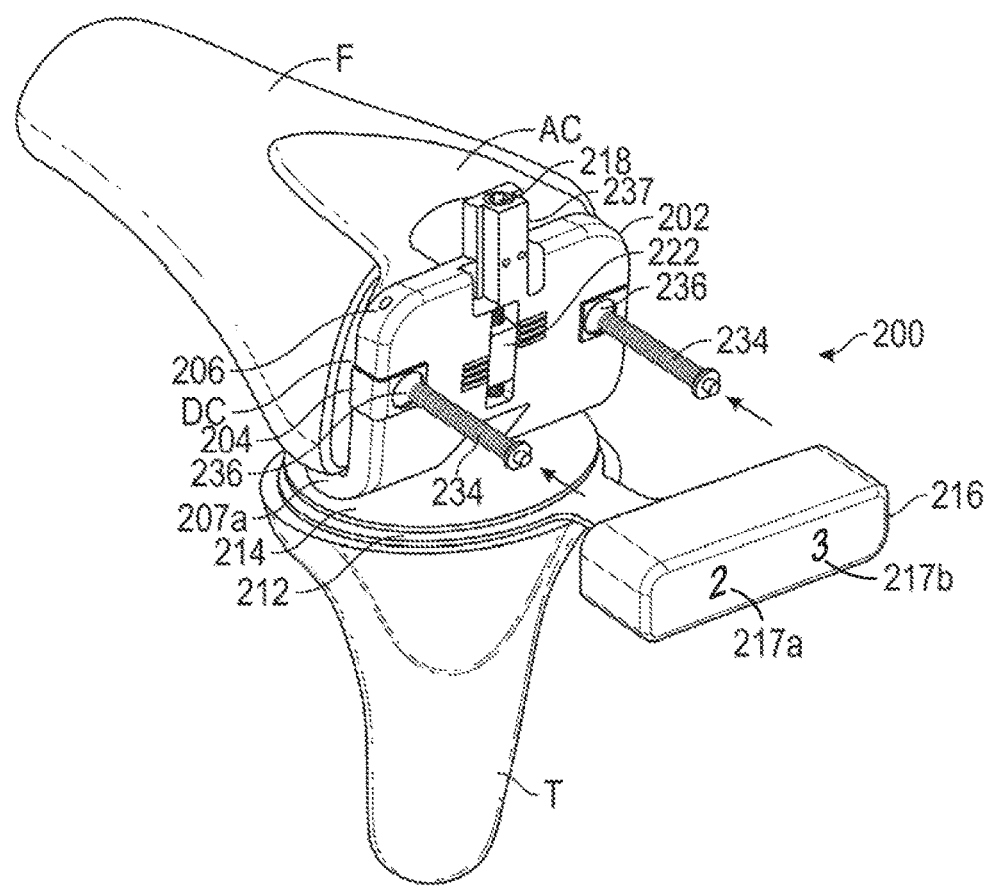
FIGS. 39A-39N are various views of the system of FIG. 37, illustrating a method of using the system, according to one embodiment of the present invention.
Figure 39B:
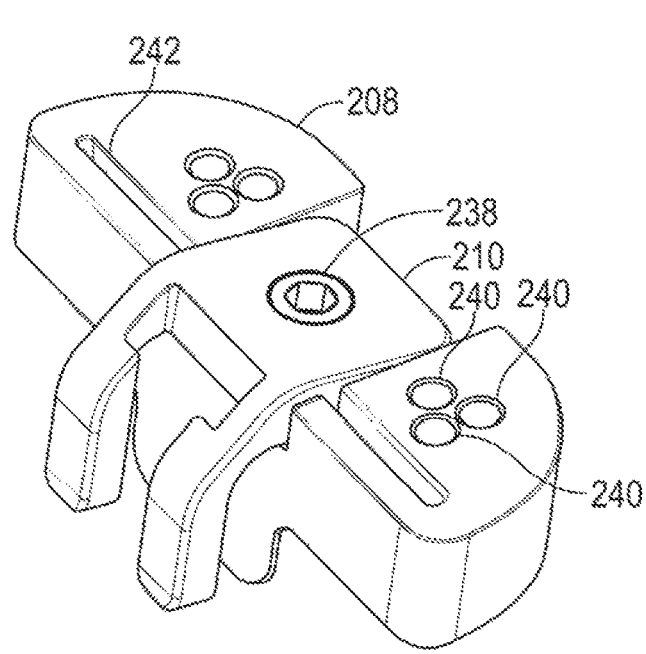
Figure 39C:
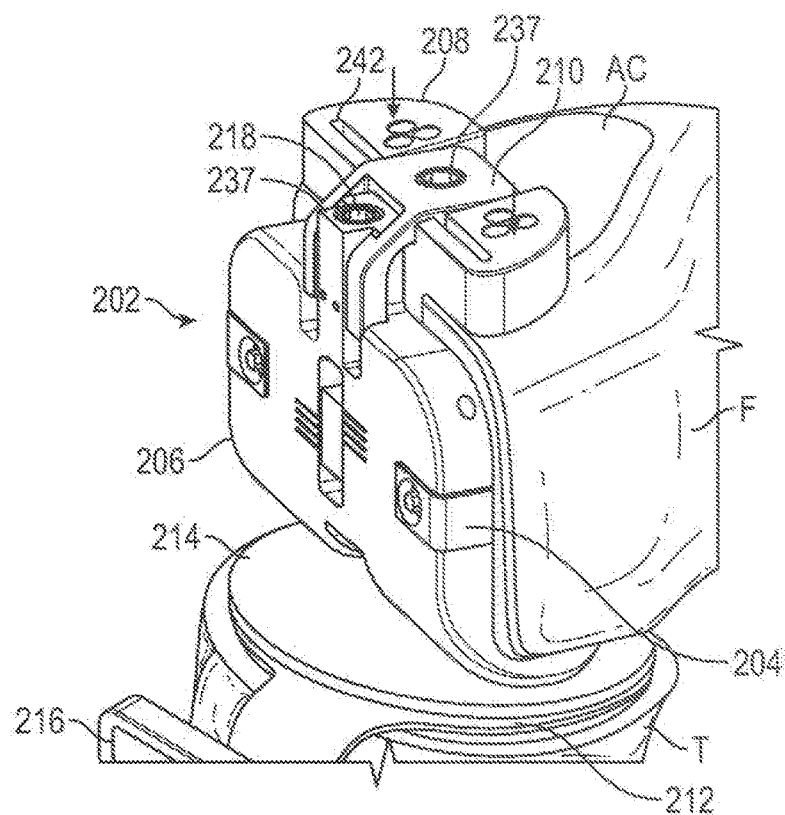
Figure 39D:
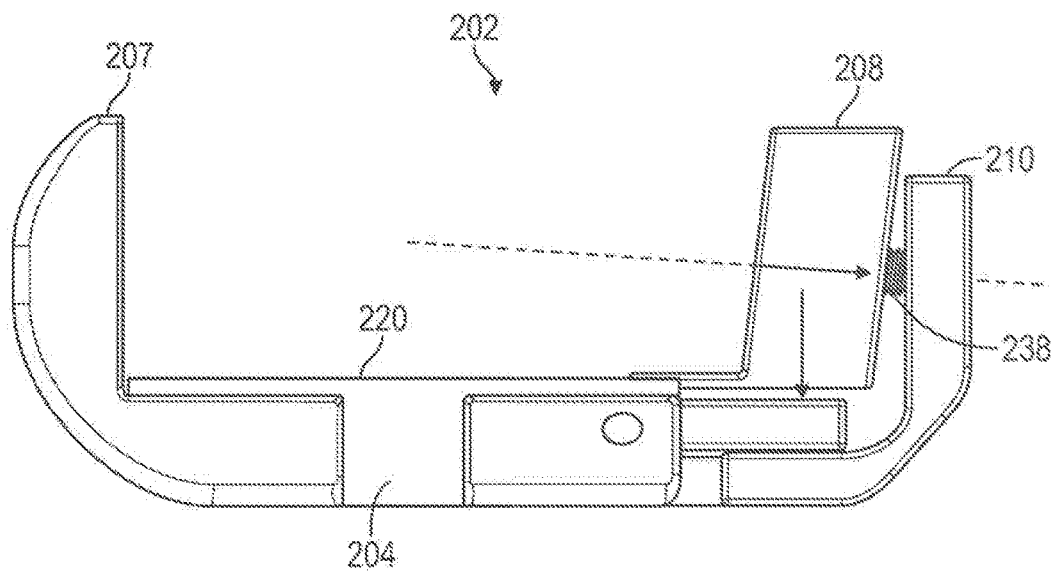
Figure 39E:
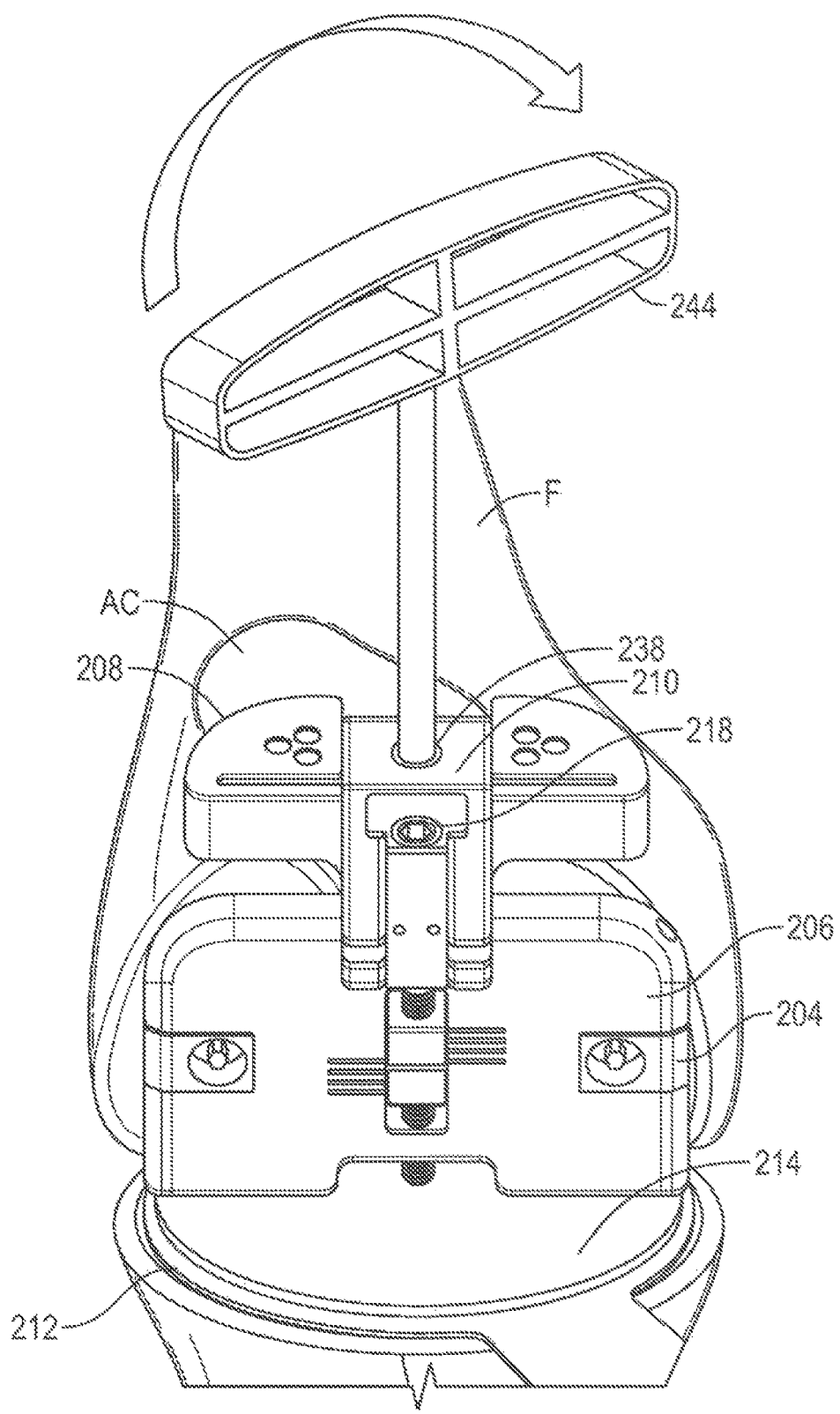
Figure 39F:
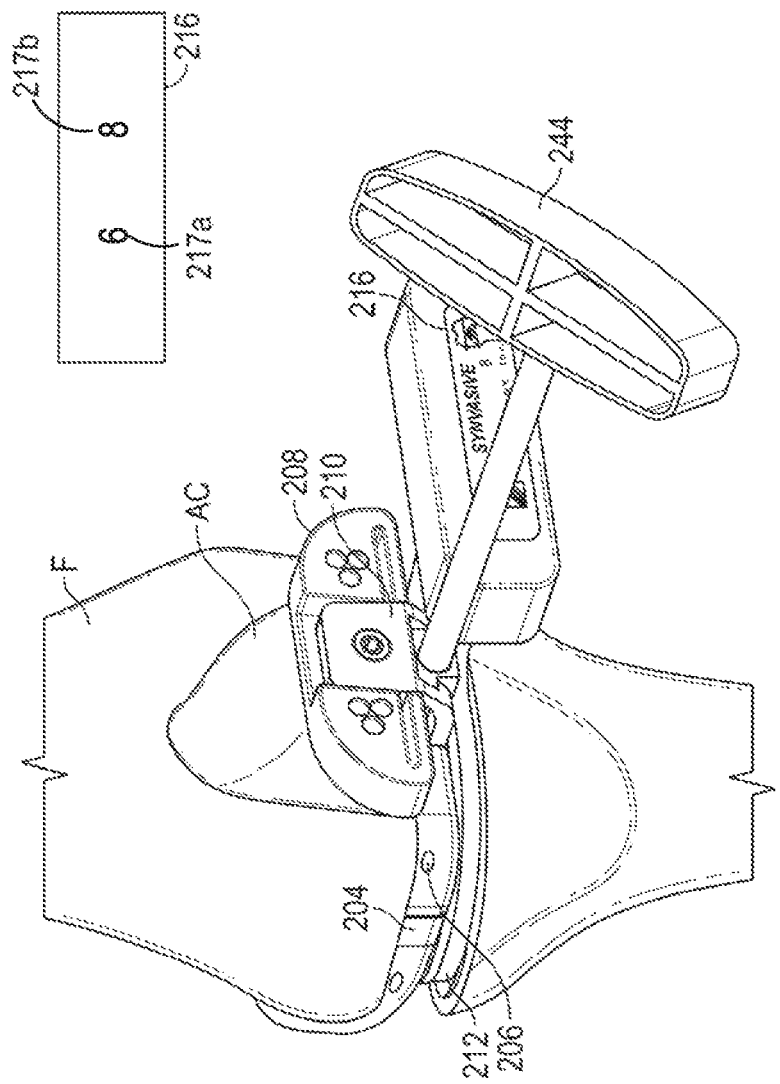
Figure 39H:
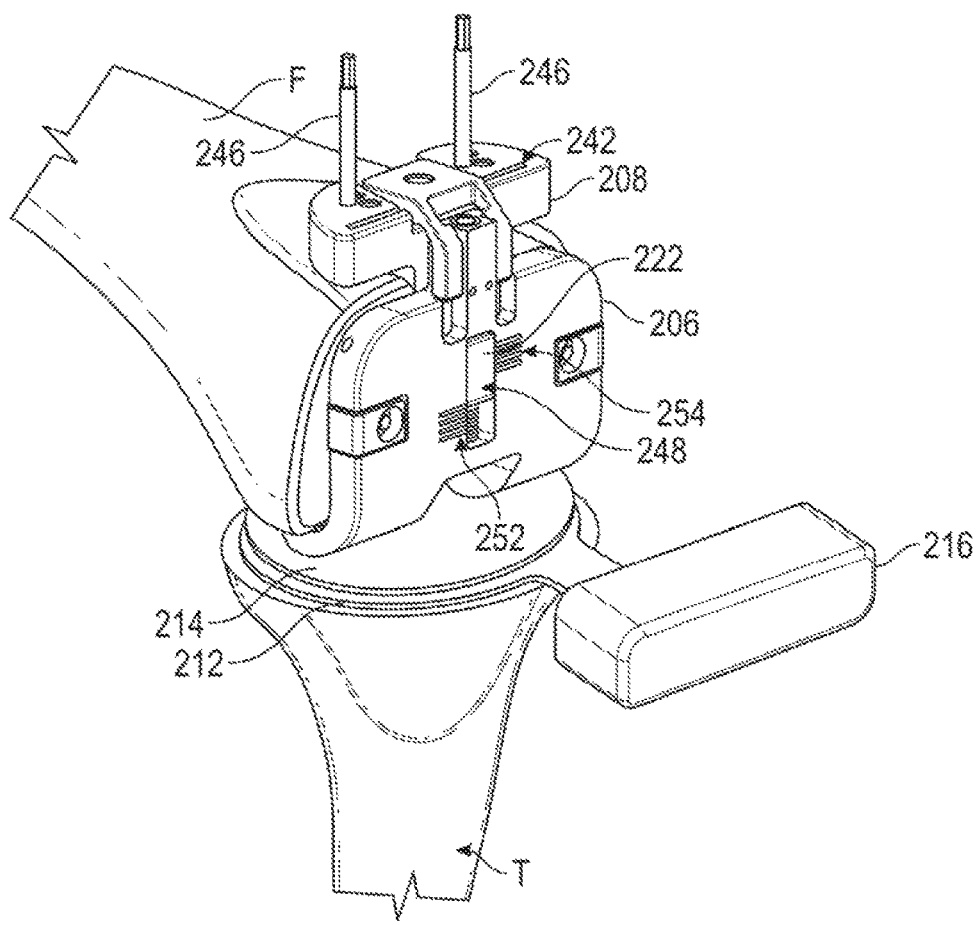
Figure 39I:
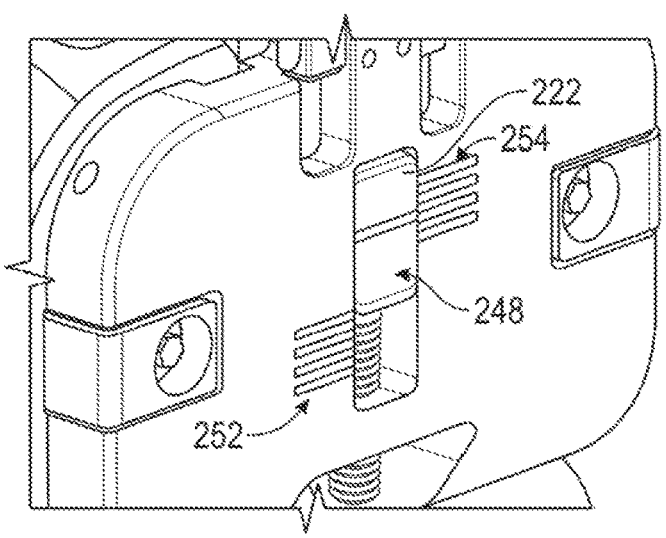
Figure 39J:
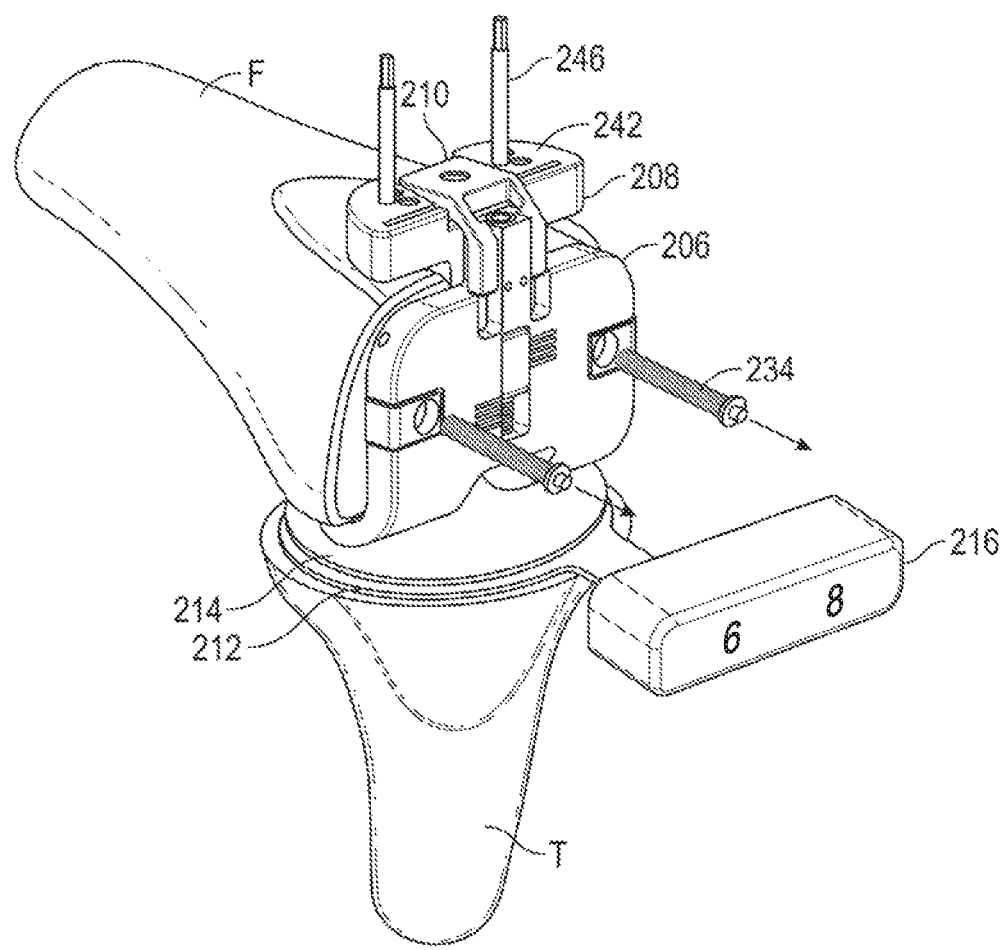
Figure 39K:
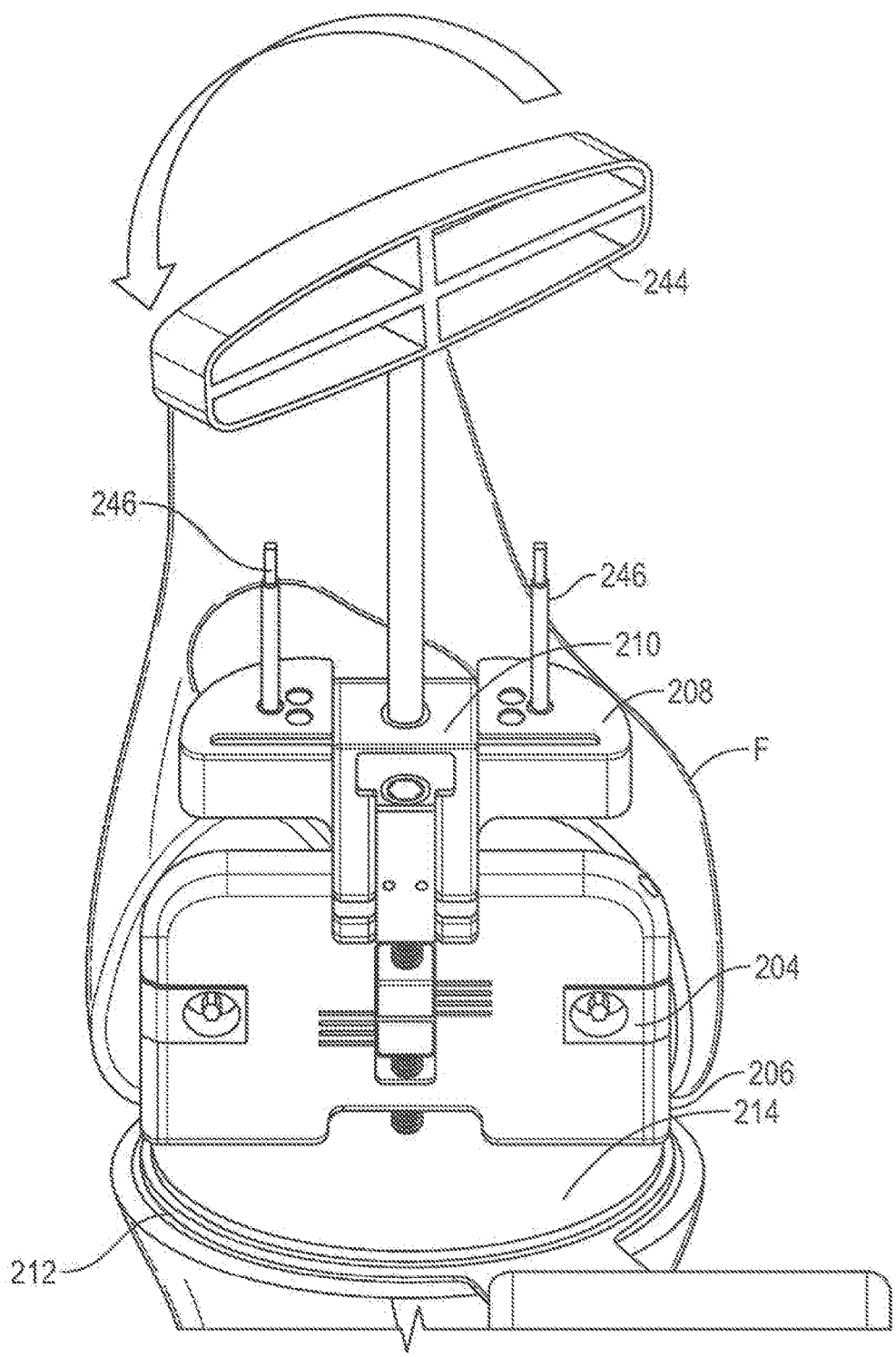
Figure 39L:
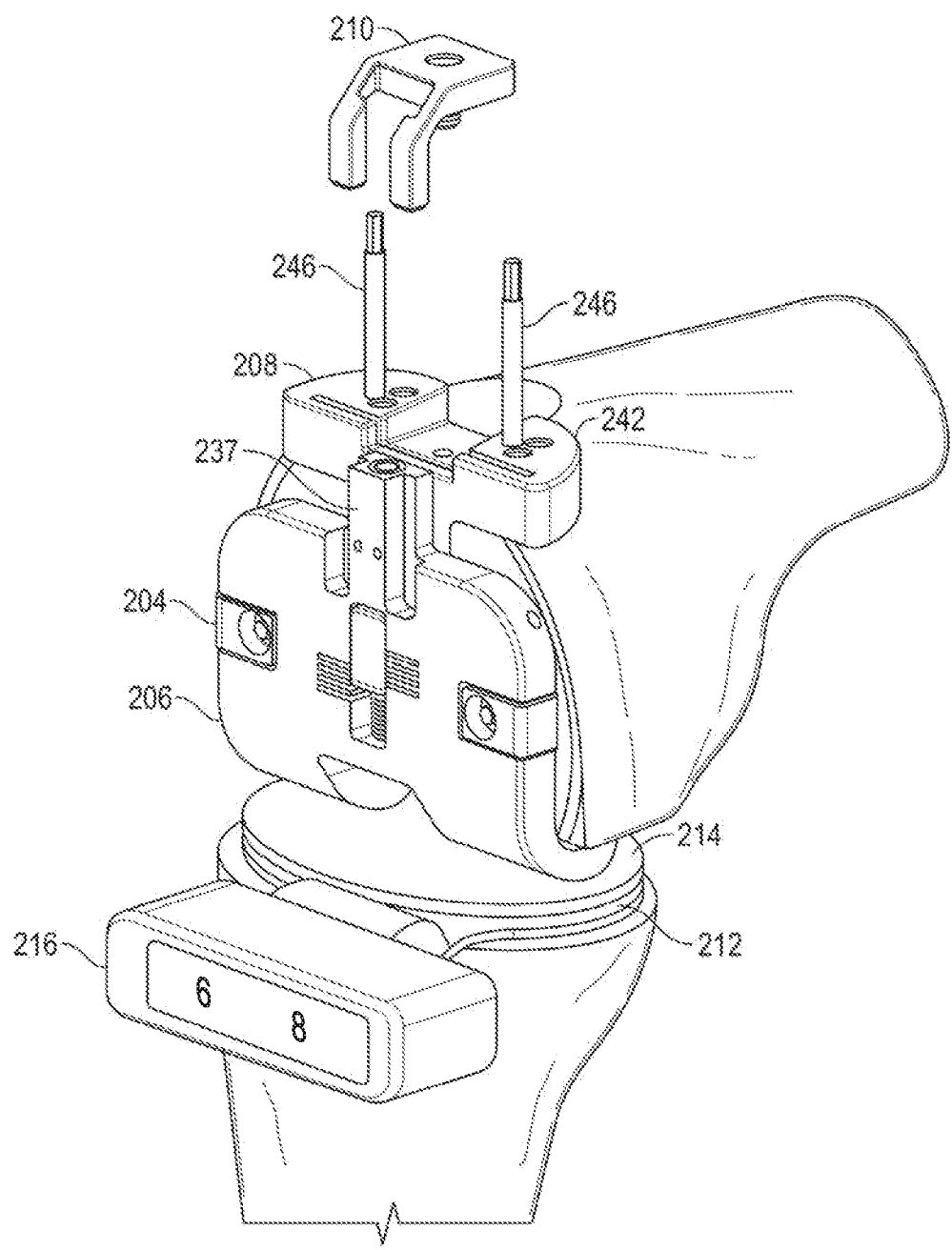
Figure 39N:
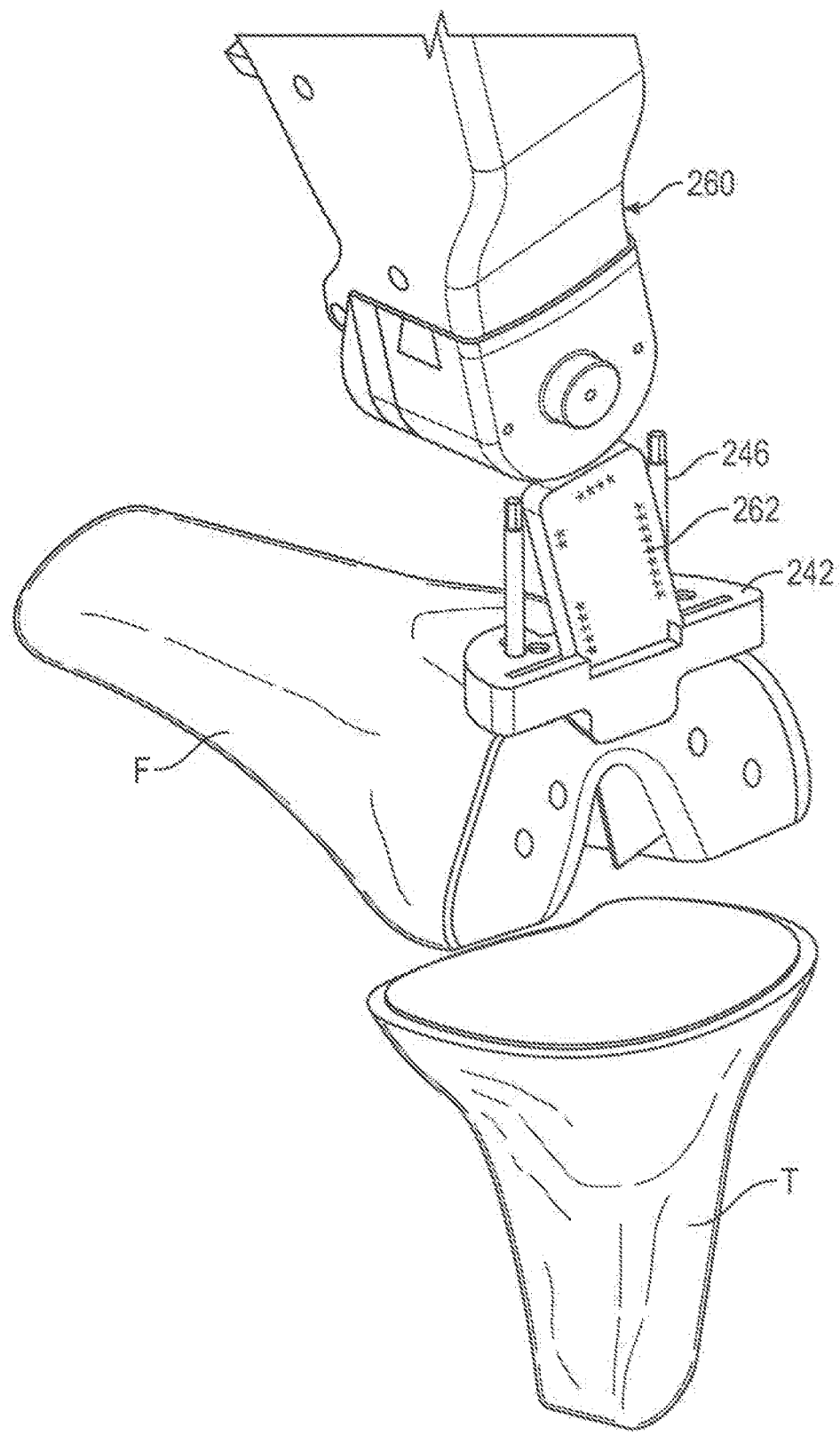

Turning now to FIGS. 39A-39N, a method for using system 200 to make a bone cut on a distal femur F will be described. Prior to the step shown in FIG. 39A, a proximal cut is made to the tibia T, and an initial distal cut DC, anterior cut AC and posterior cut (not visible) are made to the femur F. Force sensor 212 and insert 214 may then be positioned on the cut proximal end of the tibia T, and femoral attachment member 202 may be attached to the cut distal end of the femur F via screws 234 advanced through screw holes 236 of stationary portion 204. Stationary portion 204 of femoral attachment member 202 is thus fixedly attached to the femur F, and adjustable portion 206 is adjustable relative to stationary portion 204 to adjust medial and/or lateral tension in the knee. Femoral attachment member 202 is typically attached in such a way that condylar portions 207a, 207b (barely visible in FIG. 39A) abut the cut posterior surfaces of the femur F. The order in which force sensor 212, insert 214 and attachment member 202 are positioned in the knee joint is not critical to any given embodiment, and the method is not limited to positioning in any particular order. As illustrated in FIG. 39A, the various components of system 200 may be inserted into the knee joint while the knee is in flexion. This is an improvement over some systems which must be inserted with the knee in extension.

Visible in FIG. 39A are cutting guide attachment post 237 and a bottom surface of elevator adjustor 222, both of which are parts of adjustable femoral attachment member 202. Cutting guide attachment post 237 provides structure for attachment of cutting guide 208 to femoral attachment member 202. The bottom surface of elevator adjustor 222, at least in one embodiment, may be used to display to a user an amount of angular adjustment that has been made to attachment member 202. These functions will be described in greater detail below. Also illustrated is display 216, which includes a lateral force indicator 217a (or "left force indicator") and a medial force indicator 217b (or "medial force indicator"). Indicators 217a, 217b may have any suitable numerical or letter scheme, such as numbers between 0 and 20, letters from A through M, or the like. In some embodiments, the numbers may relate to Newtons of force measured by sensor 212.

FIG. 39B illustrates cutting guide 208 and slide member 210 in greater detail. Cutting guide 208 may include multiple pin apertures 240, through which pins may be advanced to attach cutting guide 208 to the femur F, a saw blade slot 242, through which a surgical saw blade is advanced to make a bone cut. Cutting guide 208 and slide member 210 are attached to one another via a screw 238 or via other means in alternative embodiments.

As shown in FIG. 39C, cutting guide 208 and slide member 210 may be advanced over guide attachment post 237 until cutting guide 208 contacts the anterior cut portion AC of the femur F.

As illustrated in FIGS. 39D and 39E, after desired advancement is achieved, screw 238 may be turned, using an adjustment device 244, to affix slide member 210 to guide attachment post 237 of femoral attachment member 202. This tightening will also secure cutting guide 208 to the anterior cut bone surface AC. In one embodiment, adjustment device 244 may be used to adjust both screw 238 and adjustment member 218. In alternative embodiments, two different adjustment devices 244 may be provided.

Referring to FIG. 39F, the knee may next be moved into extension, with system 200 in place in the joint. At this point, medial and lateral forces are sensed and displayed on display 216 as lateral indicator 217a and medial indicator 217b. As seen here, the medial and lateral forces are often out of balance (here represented by the numbers "6" and "8" on indicators 217a, 217b. Adjustment device 244 may then be used to adjust adjustment member 218 to raise either lateral elevator 214 or medial elevator 216 to at least approximately balance the medial and lateral forces. In various embodiments, adjustment device 244 may be a wrench, as shown, or any other suitable device, such as a screw driver or the like. Generally, a physician will raise one of elevators 214, 216 sufficiently to balance the measured forces in the knee, which are displayed on display 216.

Now referring to FIG. 39G, once medial and lateral forces are balanced as desired (see indicators 217a, 217b each reading "8"), pins 246 may be advanced through pin apertures 240 to attach cutting guide 208 to the femur F. As shown in FIG. 39H, the knee may then be moved back into flexion. As shown in FIGS. 39H and 39I, at this point, a reference mark 248 on the bottom surface of elevator adjustor 222 may be used in conjunction with indicator marks 252, 254, to approximate an amount of angular adjustment that has been made to femoral attachment member 202 and thus to cutting guide 208, in other words, reference mark 248 and indicator marks 252, 254 may allow a physician to approximate an angle of resection that cutting guide 208 will make on the distal end of the femur F when the cut is made. Each indicator mark 252, 254, for example, may indicate a degree of resection angle. For example, indicator marks 252 may indicate a lateral resection angle, and indicator marks 254 may indicate a medial resection angle. If reference mark 248 is located at the midpoint between the two end indicator marks 252, 254, this could designate a resection angle of approximately 0 degrees. The example shown in FIGS. 39H and 39I may designate a medial resection angle of about 2.5 degrees. Of course, in alternative embodiments, different numbers, gradations and/or configurations of reference mark 248 and indicator marks 252, 254 may be used. In other alternative embodiments, this step may be skipped, and system 200 may not include any reference mark 248 or indicator marks 252, 254.

With reference now to FIGS. 39J-39M, femoral attachment member 202 and slide member 210 may now be removed from the knee, leaving cutting guide 208 attached to the femur F. As shown in FIG. 39J, screws 234 may be removed from stationary portion 204. Next, as in FIG. 39K, adjustment device 244 may be turned to loosen slide member 210, which then may be removed from cutting guide 208 and post 237, as illustrated in FIG. 39L. Finally, as illustrated in FIG. 39M, adjustable femoral attachment member 202, sensor 212 and insert 214 may all be removed from the knee, leaving only cutting guide 208 and pins 246 attached to the femur F.

As illustrated in FIG. 39N, with cutting guide 208 in a desired position for guiding: a distal femoral bone cut, a bone saw handpiece 260 with saw blade assembly 262 may be used to make the bone cut. In some embodiments, saw blade assembly 262 will be guided by passing through slot 242, which will be oriented in a desired position based on the adjustments described above.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A method for positioning a cutting guide on a distal end of a femur, the method comprising:
    attaching an adjustable femoral attachment member to a cut distal end of the femur;
    positioning a force sensor on a cut proximal end of a tibia of the knee;
    attaching the cutting guide to the femoral attachment member;
    adjusting the femoral attachment member, using a single adjustment member of the femoral attachment member, the single adjustment member controlling translation of a portion of the single adjustment member in a first axis to elevate, along a second axis, at least one of a medial side and a lateral side of the femoral attachment member relative to the cut distal end of the femur, wherein adjusting the femoral attachment member operates to approximately balance medial and lateral forces displayed on a display coupled with the force sensor, wherein adjusting the femoral attachment member changes a position of the cutting guide relative to the femur; and
    attaching the cutting guide to the femur.

2. A method as in claim 1, wherein attaching the femoral attachment member comprises advancing two screws through holes in the femoral attachment member and into the cut distal end of the femur while the knee is in flexion.

3. A method as in claim 2, further comprising positioning an insert between the force sensor and the femoral attachment member.

4. A method as in claim 2, further comprising moving the knee into extension while the femoral attachment member remains attached to the femur and before adjusting the femoral attachment member.

5. A method as in claim 4, wherein the cutting guide is attached to the femur while the knee is in extension.

6. A method as in claim 5, wherein attaching the cutting guide comprises pinning the cutting guide to the femur using multiple pins.

7. A method as in claim 5, further comprising moving the knee back into flexion after the cutting guide is attached.

8. A method as in claim 7, further comprising viewing a resection angle indicator on a distal surface of the femoral attachment member while the knee is in flexion, wherein the resection angle indicator indicates approximately an angle of resection of the distal femur based on a position of the cutting guide.

9. A method as in claim 1, wherein attaching the cutting guide to the femoral attachment member comprises sliding the cutting guide, attached to a slide member, onto the femoral attachment member until the cutting guide contacts a cut anterior surface of the femur.

10. A method as in claim 9, further comprising, before attaching the cutting guide to the femoral attachment member, attaching the slide member to the cutting guide.

11. A method as in claim 10, wherein attaching the slide member to the cutting guide comprises tightening a first screw using an adjustment device, and wherein adjusting the femoral adjustment member comprises turning a second screw using the same adjustment device.

12. A method as in claim 1, further comprising, before attaching the femoral adjustment member, making initial cuts on the distal end of the femur, an anterior side of the femur and a posterior side of the femur.

13. A method as in claim 1, wherein the single adjustment member comprises a screw, and wherein adjusting the femoral adjustment member comprises using an adjustment device to turn the screw in a first direction to adjust the medial side of the adjustment member and in a second direction to adjust the lateral side of the adjustment member.

14. A method as in claim 1, further comprising:
    removing the femoral attachment member from the femur and the sensor from the tibia; and
    cutting the distal end of the femur, using the attached cutting guide.

15. A method as in claim 14, further comprising removing a slide member attached to the cutting guide before cutting the distal end of the femur.

16. A method comprising:
    coupling an adjustable femoral attachment member to a distal end of a femur;
    positioning a force sensor between a distal surface of the femoral attachment member and a proximal surface of a tibia;
    sliding a cutting guide onto the femoral attachment member;
    balancing ligament tension using a single adjustment member of the femoral attachment member in coordination with medial-lateral force readings from the force sensor, wherein the single adjustment member is adjusted to balance the medial-lateral force readings, and wherein adjusting the single adjustment member changes a position of the cutting guide relative to the femur.

17. A method as in claim 16, wherein adjusting the femoral attachment member comprises turning the single adjustment member using an adjustment device in at least one of a first direction, to adjust the medial force, and a second direction, to adjust the lateral force.

18. A method as in claim 17, wherein turning the single adjustment member in the first direction translates a portion of the single adjustment member along a first axis and moves a medial elevator along a second axis.

19. A method as in claim 17, wherein turning the single adjustment member in the second direction translate a portion of the single adjustment member along a first axis and moves a lateral elevator along a second axis.

20. A method comprising:
  coupling an adjustable femoral attachment member to a distal end of a femur, the adjustable femoral attachment member including:
  a stationary femoral member that couples to the distal end of the femur,
  an adjustable femoral member moveably attached to the stationary femoral member,
  a medial elevator for adjusting a distance between the stationary and adjustable femoral members along a medial edge of the adjustable femoral attachment member,
  a lateral elevator for adjusting a distance between the stationary and adjustable femoral members along a lateral edge of the adjustable femoral attachment member, and
  a single adjustment member to move at least one of the medial and lateral elevators along a first axis and translate a portion of the single adjustment member along a second axis in response to manipulation of an input to the single adjustment member;

positioning a force sensor adjacent a distal surface of the adjustable femoral attachment member, the force sensor configured to provide a medial force reading and a lateral force reading;

adjusting ligament tension between the femur and a tibia at least in part through input to the single adjustment member to manipulate the medial force reading and the lateral force reading.

* * * * *